US011633382B2

(12) United States Patent
Eriksson et al.

(10) Patent No.: US 11,633,382 B2
(45) Date of Patent: Apr. 25, 2023

(54) TREATMENT OF ER-NEGATIVE BREAST CANCER WITH AN PDGF-CC INHIBITOR AND ANTI-ESTROGEN

(71) Applicant: Paracrine Therapeutics AB, Bålsta (SE)

(72) Inventors: Ulf Eriksson, Bålsta (SE); Kristian Pietras, Vellinge (SE); Pernilla Roswall, Enköping (SE)

(73) Assignee: Paracrine Therapeutics AB, Balsta (SE)

( * ) Notice: Subject to any disclaimer, the term of this patent is extended or adjusted under 35 U.S.C. 154(b) by 639 days.

(21) Appl. No.: 15/774,341

(22) PCT Filed: Nov. 10, 2016

(86) PCT No.: PCT/EP2016/077295
§ 371 (c)(1),
(2) Date: May 8, 2018

(87) PCT Pub. No.: WO2017/081171
PCT Pub. Date: May 18, 2017

(65) Prior Publication Data
US 2021/0186932 A1 Jun. 24, 2021

(30) Foreign Application Priority Data

Nov. 10, 2015 (SE) .................................. 1551455-7
Jul. 4, 2016 (SE) .................................. 1650974-7

(51) Int. Cl.
| | |
|---|---|
| *A61K 31/4196* | (2006.01) |
| *A61P 35/00* | (2006.01) |
| *A61K 31/138* | (2006.01) |
| *A61K 39/395* | (2006.01) |
| *A61K 39/00* | (2006.01) |
| *A61K 31/40* | (2006.01) |
| *A61K 31/4025* | (2006.01) |
| *A61K 31/437* | (2006.01) |
| *A61K 31/451* | (2006.01) |
| *A61K 31/452* | (2006.01) |
| *A61K 31/4535* | (2006.01) |
| *A61K 31/506* | (2006.01) |
| *A61K 31/565* | (2006.01) |
| *A61K 31/566* | (2006.01) |

(52) U.S. Cl.
CPC ........ *A61K 31/4196* (2013.01); *A61K 31/138* (2013.01); *A61K 31/40* (2013.01); *A61K 31/4025* (2013.01); *A61K 31/437* (2013.01); *A61K 31/451* (2013.01); *A61K 31/452* (2013.01); *A61K 31/4535* (2013.01); *A61K 31/506* (2013.01); *A61K 31/565* (2013.01); *A61K 31/566* (2013.01); *A61K 39/3955* (2013.01); *A61P 35/00* (2018.01); *A61K 2039/505* (2013.01); *A61K 2039/545* (2013.01)

(58) Field of Classification Search
CPC .. A61K 31/4196; A61K 31/138; A61K 31/40; A61K 31/4025; A61K 31/437; A61K 31/451; A61K 31/452; A61K 31/4535; A61K 31/506; A61K 31/565; A61K 31/566; A61K 39/3955; A61K 2039/505; A61K 2039/545; A61K 45/06; A61K 39/39; A61P 35/00; A61P 43/00; C07K 2317/75; C07K 16/22
See application file for complete search history.

(56) References Cited

FOREIGN PATENT DOCUMENTS

| WO | 2005087812 A1 | 9/2005 | |
|---|---|---|---|
| WO | 2011128434 A2 | 10/2011 | |
| WO | 2013160359 A1 | 10/2013 | |
| WO | WO-2013160359 A1 * | 10/2013 | ................ A61P 9/00 |

OTHER PUBLICATIONS

Padlan (Advances in Protein Chemistry, 1996, 49:57-133) (Year: 1996).*
Gruvberger-Saal SK, Bendahl PO, Saal LH, Laakso M, HegardtC, Edén P, Peterson C, Malmström P, Isola J, Borg A, Fernö M. Estrogen receptor beta expression is associated with tamoxifen response in ERalpha-negative breast carcinoma. Clin Cancer Res. Apr. 1, 2007;13(7):1987-94. (Year: 2007).*
Berglund (Protein Science, 2008, 17:606-613) (Year: 2008).*
Ma G, He J, Yu Y, Xu Y, Yu X, Martinez J, Lonard DM, Xu J. Tamoxifen inhibits ER-negative breast cancer cell invasion and metastasis by accelerating Twist1 degradation. Int J Biol Sci. Apr. 11, 2015;11(5):618-28. (Year: 2015).*
R&D Systems, Human PDGF-C Antibody, MAB1560, Jul. 5, 2015 (Year: 2015).*
Rana Kanaan, Charlie Strange, European Respiratory Review Dec. 2017, 26 (146) 170061 (Year: 2017).*
Chen (Sci Adv. Apr. 1, 2020;6(14):eaaz7825) (Year: 2020).*
Yin, L., Duan, JJ., Bian, XW et al. Triple-negative breast cancer molecular subtyping and treatment progress. Breast Cancer Res 22, 61 (2020). (Year: 2020).*

(Continued)

*Primary Examiner* — Julie Wu
*Assistant Examiner* — Sung Min Yoon
(74) *Attorney, Agent, or Firm* — Dinsmore & Shohl LLP; Weston R. Gould

(57) ABSTRACT

The invention discloses that ER-negative breast cancers can be converted into ER positive breast cancers, such as to a breast cancer of luminal-like phenotype by treatment with anti-PDGF-CC antibodies. ER-positive breast cancers, including luminal-like breast cancers can be treated with anti-estrogen treatment. On this basis the invention discloses that surprisingly, ER-negative breast cancers can be treated with anti-estrogen treatment, if the treatment is combined with treatment with anti-PDGF-CC antibodies. Said treatment may for example be an adjuvant treatment, for example a treatment aiming at reducing the risk of relapse of a breast cancer after removal of the primary tumor by surgery.

6 Claims, 30 Drawing Sheets
Specification includes a Sequence Listing.

(56) References Cited

OTHER PUBLICATIONS

Austin D, Hamilton N, Elshimali Y, Pietras R, Wu Y, Vadgama J. Estrogen receptor-beta is a potential target for triple negative breast cancer treatment. Oncotarget. 2018;9(74):33912-33930. Published Sep. 21, 2018. doi:10.18632/oncotarget.26089 (Year: 2018).*

NCT01234532 (clinical trial, Oct. 7, 2013 (v9)) (Year: 2013).*

Dowsett M, Houghton J, Iden C, Salter J, Farndon J, A'Hern R, Sainsbury R, Baum M. Benefit from adjuvant tamoxifen therapy in primary breast cancer patients according oestrogen receptor, progesterone receptor, EGF receptor and HER2 status. Ann Oncol. May 2006;17(5):818-26. (Year: 2006).*

Jose Balsega et al., "Randomized Phase II Study of the Anti-Epidermal Growth Factor Receptor Monoclonal Antibody Cetuximab With Cisplatin Versus Cisplatin Alone in Patients With Metastatic Triple-Negative Breast Cancer", J Clin Oncol, 31:2586-2592, 2013.

Kimberly Blackwell et al. "Tamoxifen Inhibits Angiogenesis in Estrogen Receptor-negative Animal Models1", Clinical Cancer Research, vol. 6, 4359-4364, Nov. 2000.

Bottrell, Alyssa. "The Role of Platelet-Derived Growth Factor C and Its Splice Variant in Breast Cancer", U.S. Army Medical Research and Materiel Command, Fort Detrick, Maryland 21702-5012, 2014.

D. A. Bronzert et al. "Synthesis and secretion of platelet-derived growth factor by human breast cancer cell lines", Proc. Natl. Acad. Sci. USA, vol. 84, pp. 5763-5767, Aug. 1987.

Maggie C.U. Cheang et al. "Basal-LikeBreastCancerDefinedby Five Biomarkers Has Superior PrognosticValue thanTriple-Negative Phenotype", Clin Cancer Res 2008;14(5); Mar. 1, 2008.

Yongping Crawford et al., "PDGF-C Mediates the Angiogenic and Tumorigenic Properties of Fibroblasts Associated with Tumors Refractory to Anti-VEGF Treatment", Cancer Cell 15, 21-34, Jan. 6, 2009.

Carmen Criscitiello et al. "Investigational platelet-derived growth factor receptor kinase inhibitors in breast cancer therapy", Expert Opin. Investig. Drugs, 23(5):599-610, 2014.

Early Breast Cancer Trialists' Collaborative Group (EBCTCG). "Relevance of breast cancer hormone receptors and other factors to the effi cacy of adjuvant tamoxifen: patient-level meta-analysis of randomised trials", Lancet; 378: 771-84, 2011.

William D. Foulkes et al. "Triple-Negative Breast Cancer", N Engl J Med;363:1938-48, 2010.

Clifford A. Hudis and Luca Gianni, "Triple-Negative Breast Cancer: An Unmet Medical Need", The Oncologist;16 (suppl 1):1-11, 2011.

Martin Jechlinger et al. "Autocrine PDGFR signaling promotes mammary cancer metastasis", The Journal of Clinical Investigation, vol. 116, No. 6, Jun. 2006.

H. Joensuu & J. Gligorov, "Adjuvant treatments for triple-negative breast cancers", Annals of Oncology 23 (Supplement 6): vi40-vi45, 2012.

IA Laba J De et al. "P2-05-07: Combined Antiangiogenic and Anti-Estrogen Therapy in Breast Cancer. Molecular Mechanisms Involved.", Cancer Res;71(24 Suppl): Abstract nr P2-05-07, 2011.

Cornelia Liedtke et al. "Response to Neoadjuvant Therapy and Long-Term Survival in Patients With Triple-Negative Breast Cancer", Journal of Clinical Oncology, vol. 26, No. 8, Mar. 10, 2008.

Nian-An Luo et al. "Post-Transcriptional Up-Regulation of PDGF-C by HuR in Advanced and Stressed Breast Cancer", Int. J. Mol. Sci., 15, 20306-20320, 2014.

Suleiman Massarweh et al. "Tamoxifen Resistance in Breast Tumors Is Driven by Growth Factor Receptor Signaling with Repression of Classic Estrogen Receptor Genomic Function", Cancer Res 2008; 68: (3). Feb. 1, 2008.

C. Mindhenke et al. "Effects of tamoxifen and imatinib on the radiosensitivity of breast carcinoma cells". J Clin Oncol, vol. 26, May 20, 2008.

Astrid M. Pedersen et al. "Sorafenib and nilotinib resensitize tamoxifen resistant breast cancer cells to tamoxifen treatment via estrogen receptor [alpha]". International Journal of Oncology vol. 45, Aug. 22, 2014, 2167-2175.

Mauricio P. Pinto et al. "Malignant stroma increases luminal breast cancer cell proliferation and angiogenesis through platelet-derived growth factor signaling", BMC Cancer, 14:735, 2014.

Leanne Stalker et al. "Inhibition of proliferation and migration of luminal and claudin-low breast cancer cells by PDGFR inhibitors", Cancer Cell International, 14:89, 2014.

Dong-Yu WANG et al. "Identification of Estrogen-Responsive Genes by Complementary Deoxyribonucleic Acid Microarray and Characterization of a Novel Early Estrogen-Induced Gene: EEIG1", Molecular Endocrinology 18(2):402-411, 2004.

Marion T. Weigel et al. "Enhanced expression of the PDGFR/Abl signaling pathway in aromatase inhibitor-resistant breast cancer", Annals of Oncology 24: 126-133, 2013.

Marion T. Weigel et al. "P4-01-01: Preclinical and Clinical Studies of Estrogen Deprivation Support the PDGF/AblPathway as a Novel Therapeutic Target for Overcoming Resistance.", Cancer Res 71; P4-01-01, Dec. 15, 2011.

Marion T. Weigel et al. "Preclinical and clinical studies of estrogen deprivation support the PDGF/Abl pathway as a novel therapeutic target for overcoming endocrine resistance in breast cancer", Breast Cancer Research, 14:R78, 2012.

Shu-Chuan Weng, et al. "Sensitizing estrogen receptor-negative breast cancer cells to tamoxifen with OSU-03012, a novel celecoxib-derived phosphoinositide-dependent inhibitor". Molecular Cancer Therapeutics, vol. 7, No. 4, Apr. 1, 2008, 800-808.

A Laba J De et al. "P2-05-07: Combined Antiangiogenic and Anti-Estrogen Therapy in Breast Cancer. Molecular Mechanisms Involved.", Cancer Res;71 (24 Suppl): Abstract nr P2-05-07, 2011.

Kaygusuz-Atagunduz, et al.: Journal of Cancer Research and Therapeutics, 2014; vol. 10, No. 4, pp. 1107-1108.

Krause, et al.: The New England Journal of Medicine, 2005; vol. 353, No. 2, pp. 172-187.

Scandlyn, et al.: British Journal of Cancer, 2008; vol. 99, No. 7, pp. 1056-1063.

IA Haba J. De et al. "P2-05-07: Combined Antiangiogenic and Anti-Estrogen Therapy in Breast Cancer. Molecular Mechanisms Involved"; Cancer Res, 71 (24 Suppl); Abstract, P2-05-07, 2011.

C. Mundhenke et al, "Effects of tamoxifen and imatinib on the radiosensitivity of breast carcinoma cells." J Clin Oncol., vol. 26, May 20, 2008, Abstr. 14639.

Liang et al., Suppression of Extracellular Signals and Cell Proliferation Through EGF Receptor Binding by (−)-Epigallocatechin Gallate in Human A431 Epiderrnoid Carcinoma Cells, J. Cell. Biochem, 67(1): 55-65; 1997.

Andersson, S. et al., Insufficient antibody validation challenges oestrogen receptor beta research, Nature Communications, 8:15840, Jun. 15, 2017.

Honma, N. et al., Clinical Importance of Estrogen Receptor-Evaluation in Breast Cancer Patients Treated With Adjuvant Tamoxifen Therapy, Journal of Clinical Oncology, 26(22): 3727-3734, Aug. 1, 2008.

Miller, W. et al., Oestrogen receptor ß and neoadjuvant therapy with tamoxifen: prediction of response and effects of treatment, British Journal of Cancer, 94: 1333-1338, 2006.

Novelli, F. et al., A divergent role for estrogen receptor-beta in node-positive and node-negative breast cancer classified according to molecular subtypes: an observational prospective study, Breast Cancer Research, 10:R74, 2008.

* cited by examiner

H
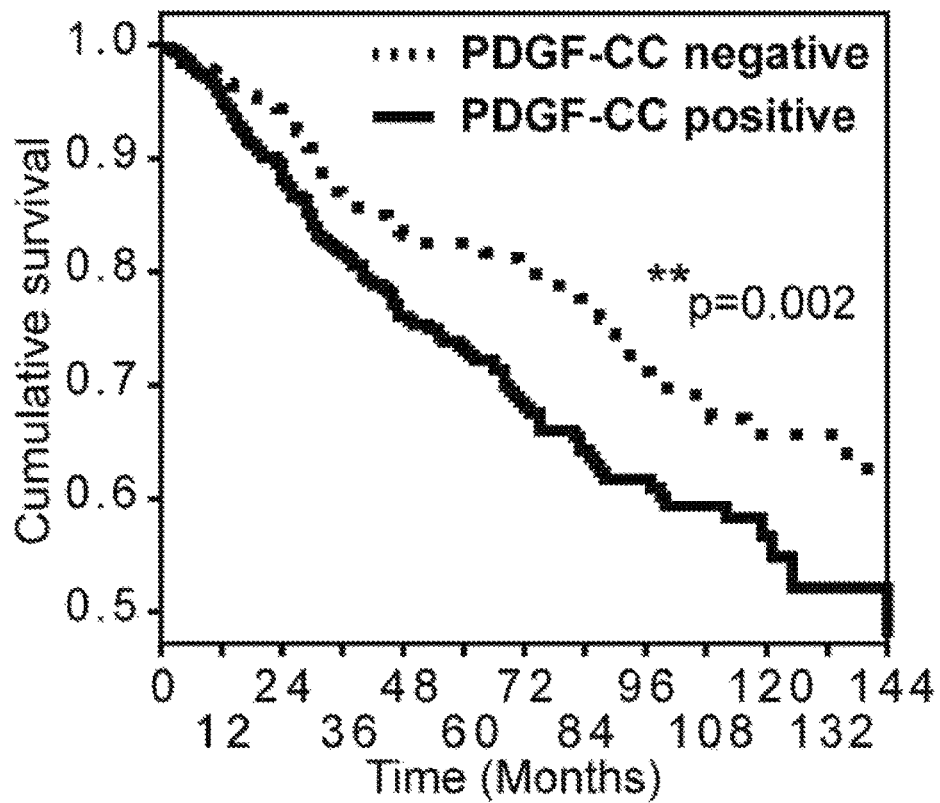
I
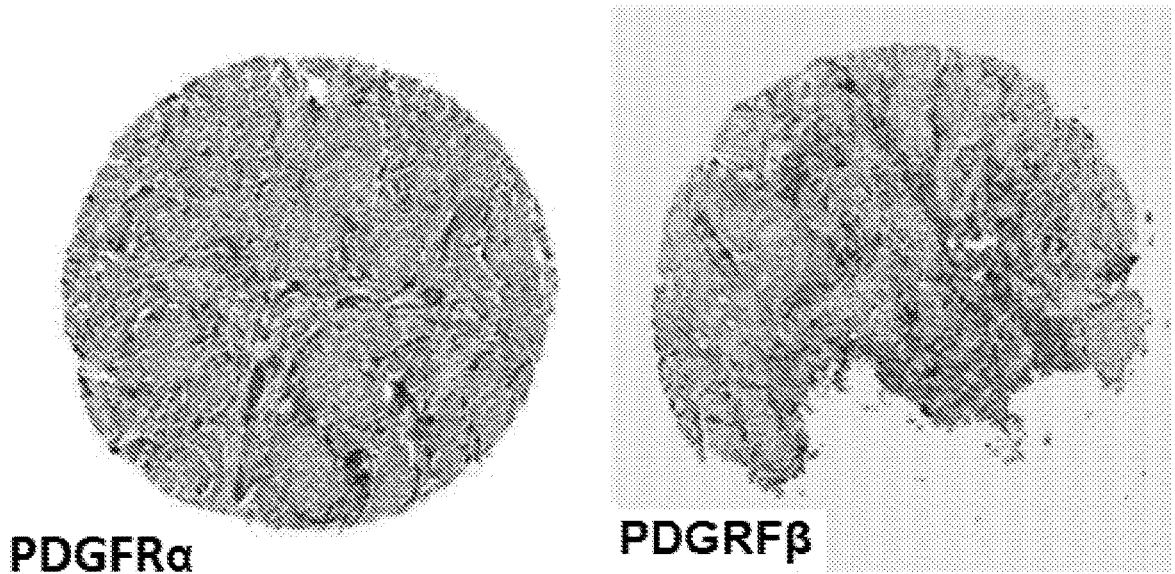
Fig. 1 cont'

A

PDGF-CC

PDGRFα
PDGRFβ

B

C
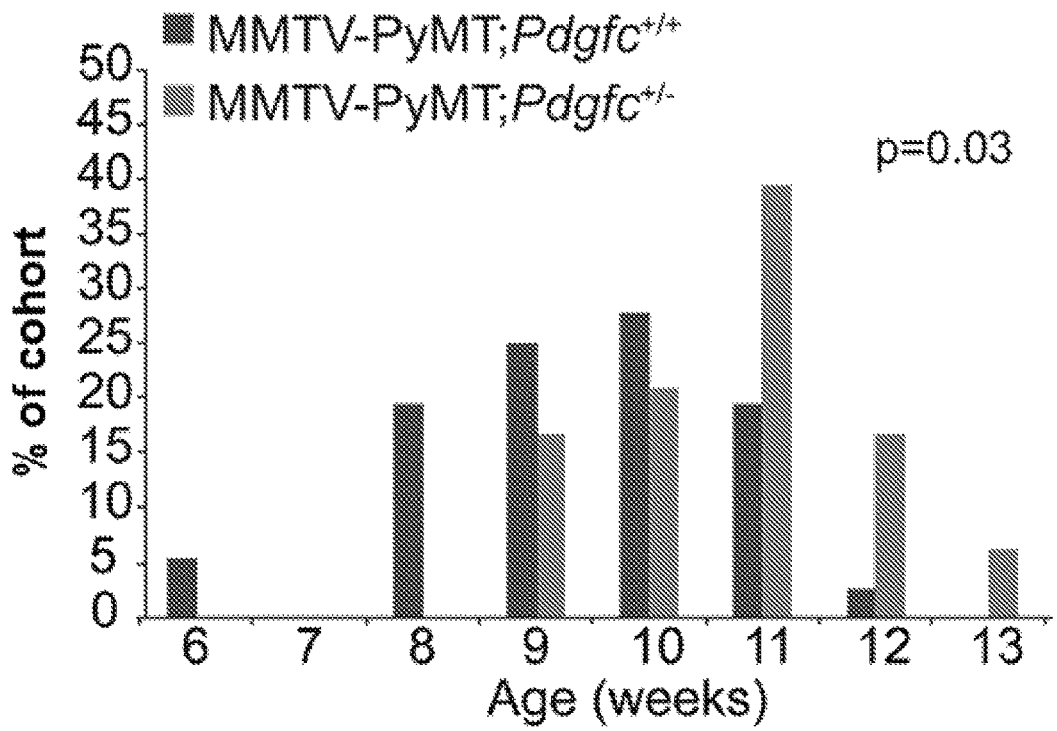
D
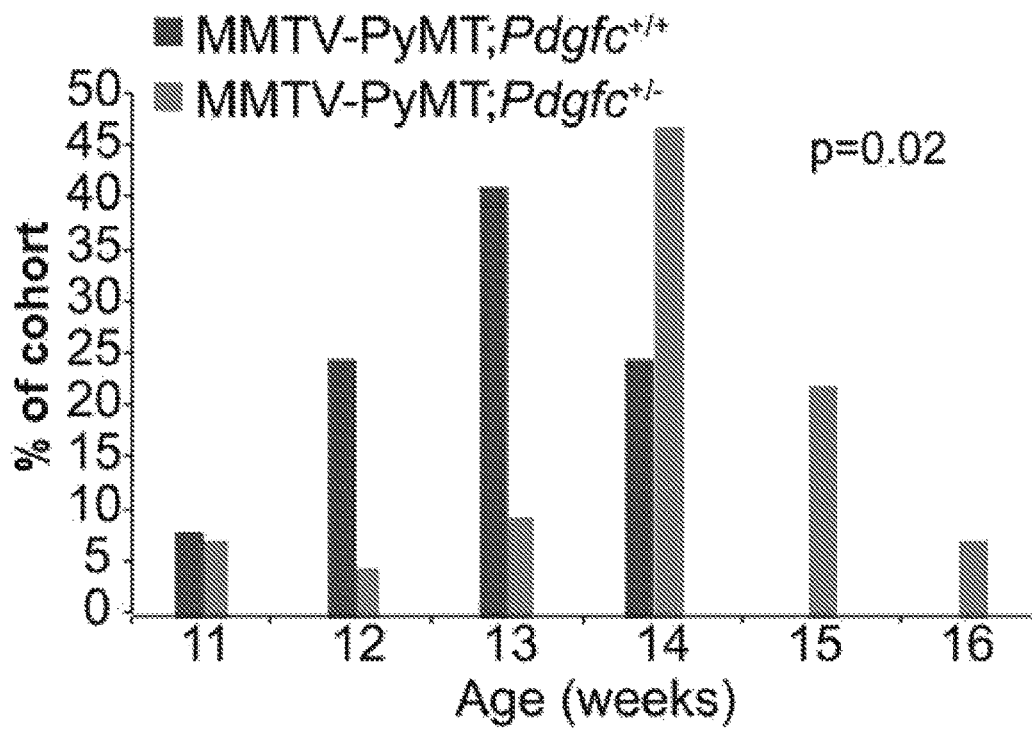
Fig. 2 cont'

E
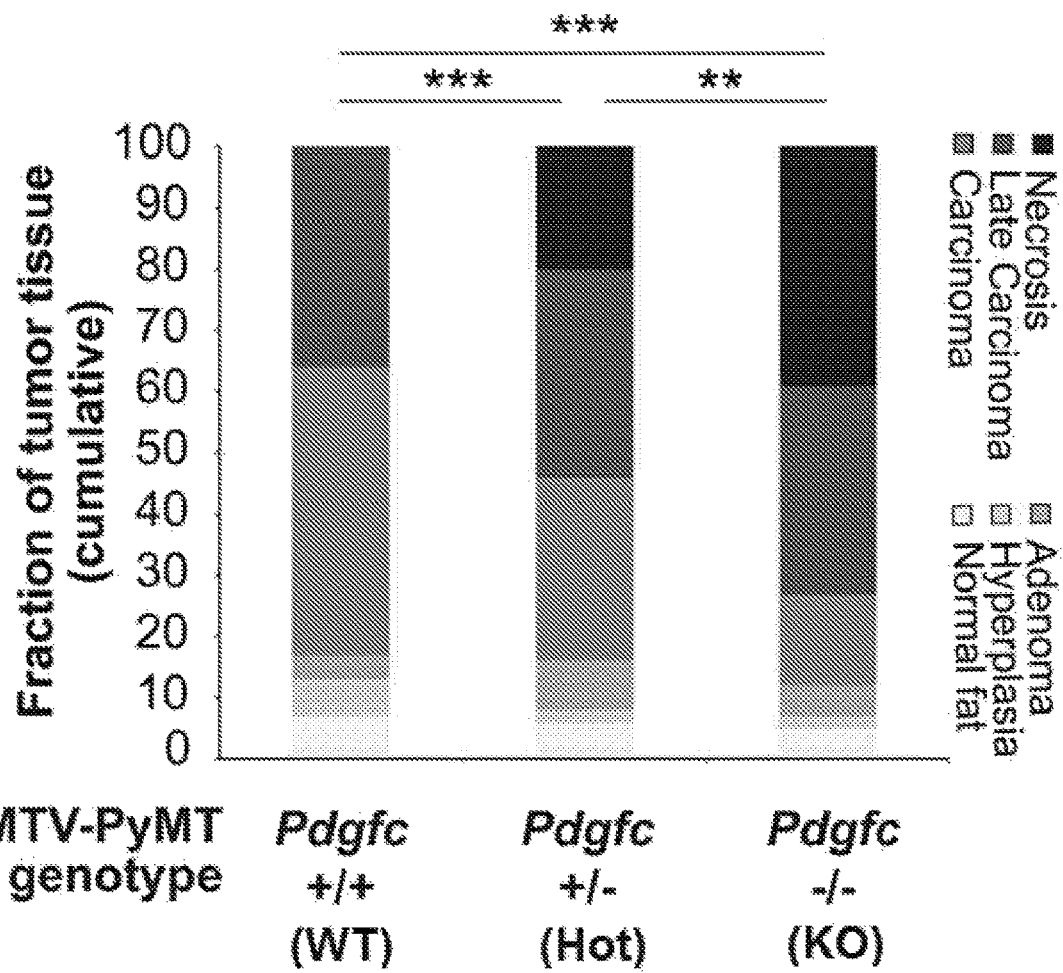
Fig. 2 cont'

F
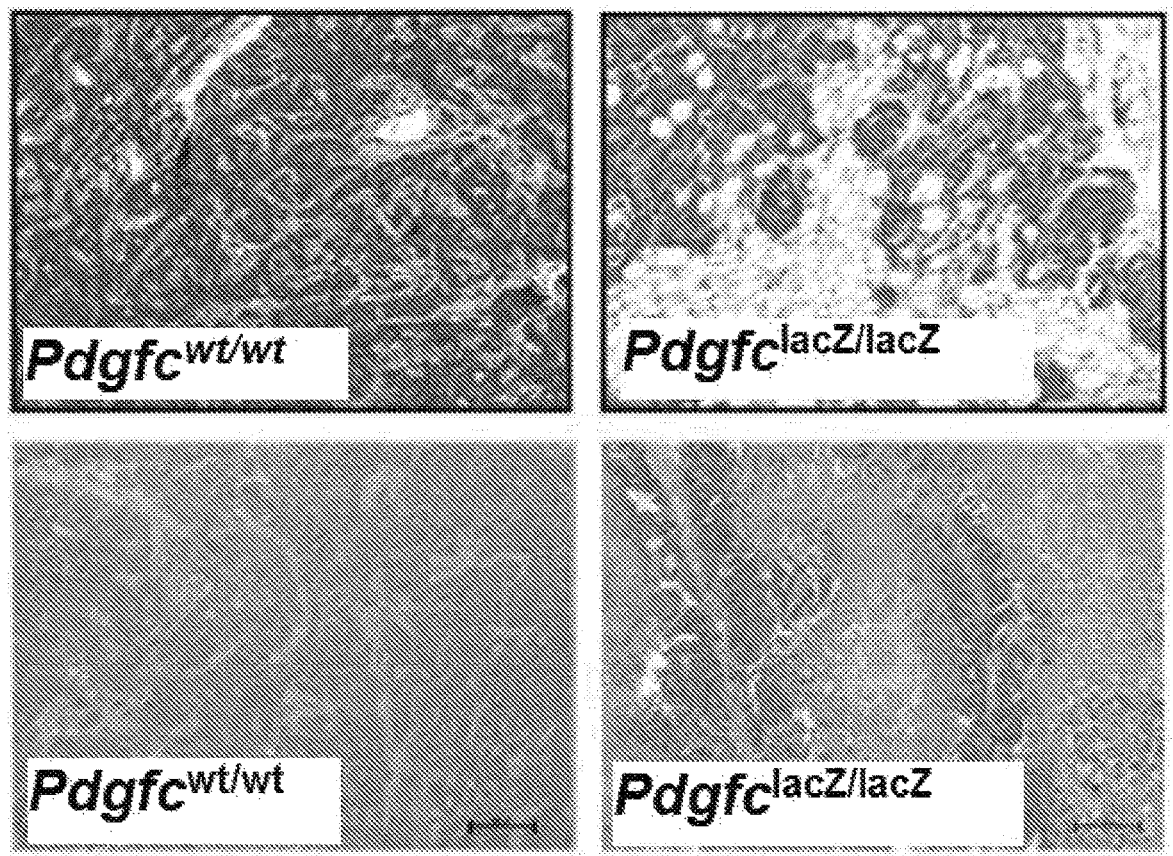
Fig. 2 cont'

G
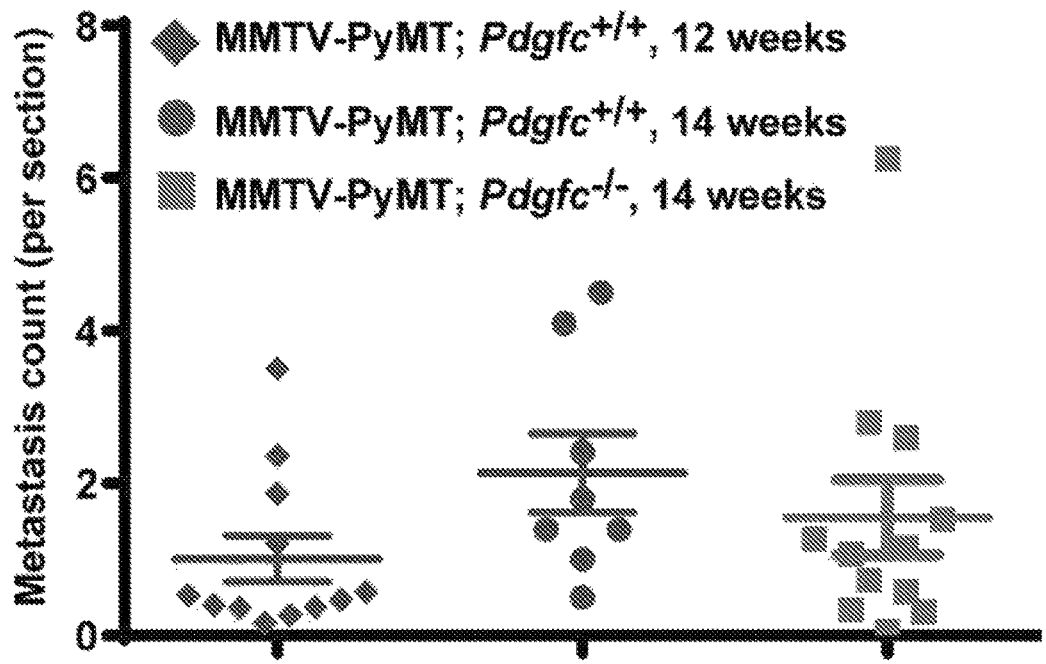
H
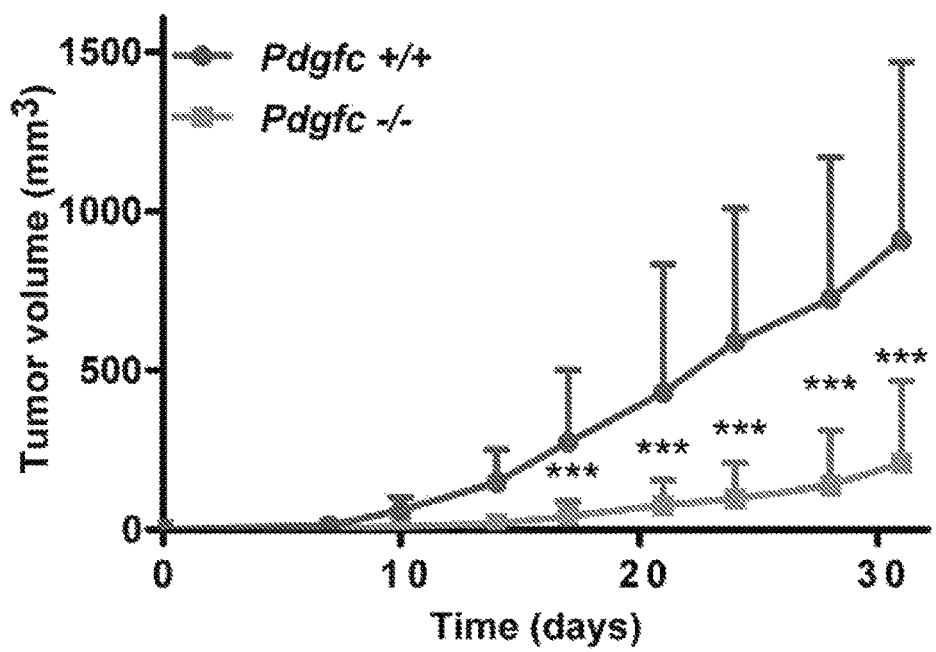
Fig. 2 cont'

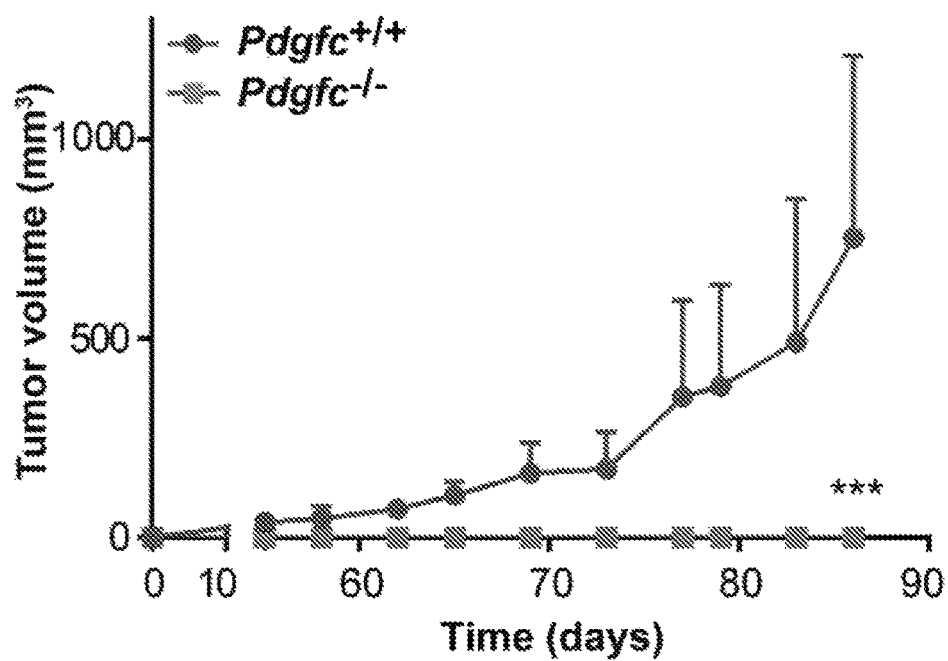
Fig. 2 cont'

A

B

C
HIF1α
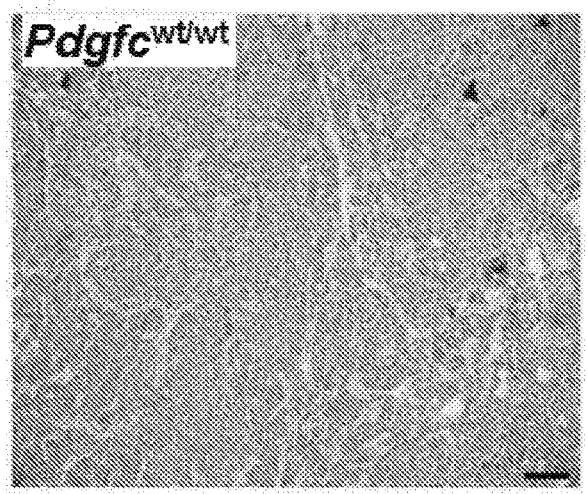 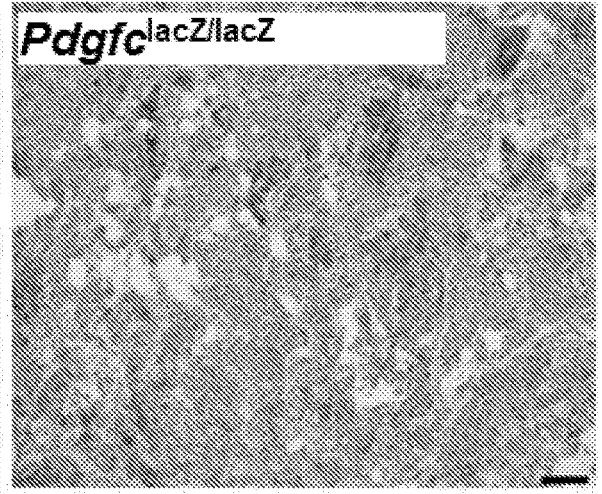
D
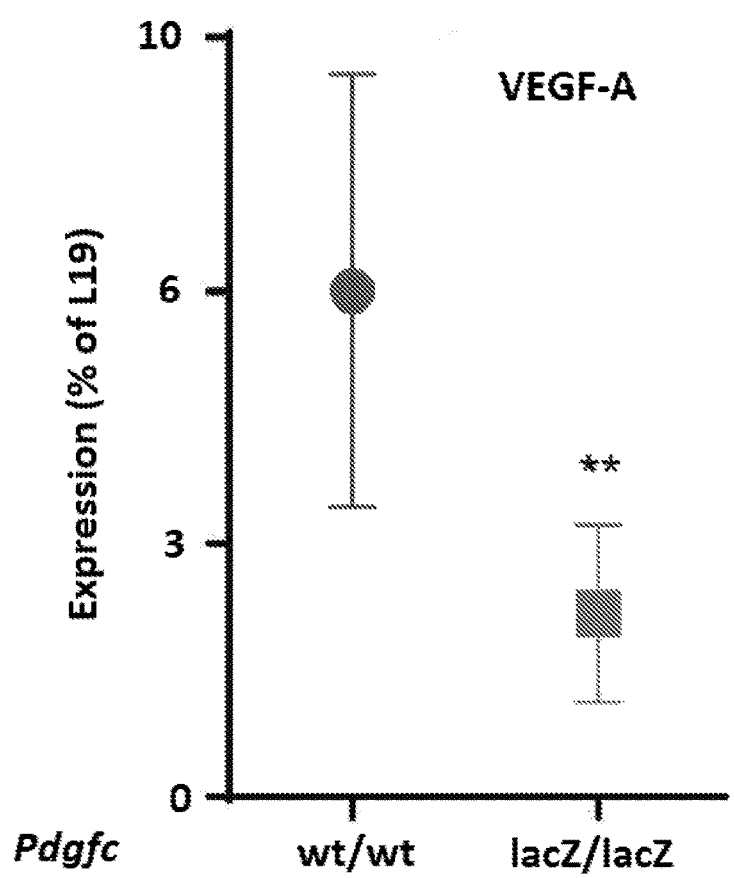
Fig. 3 cont'

E
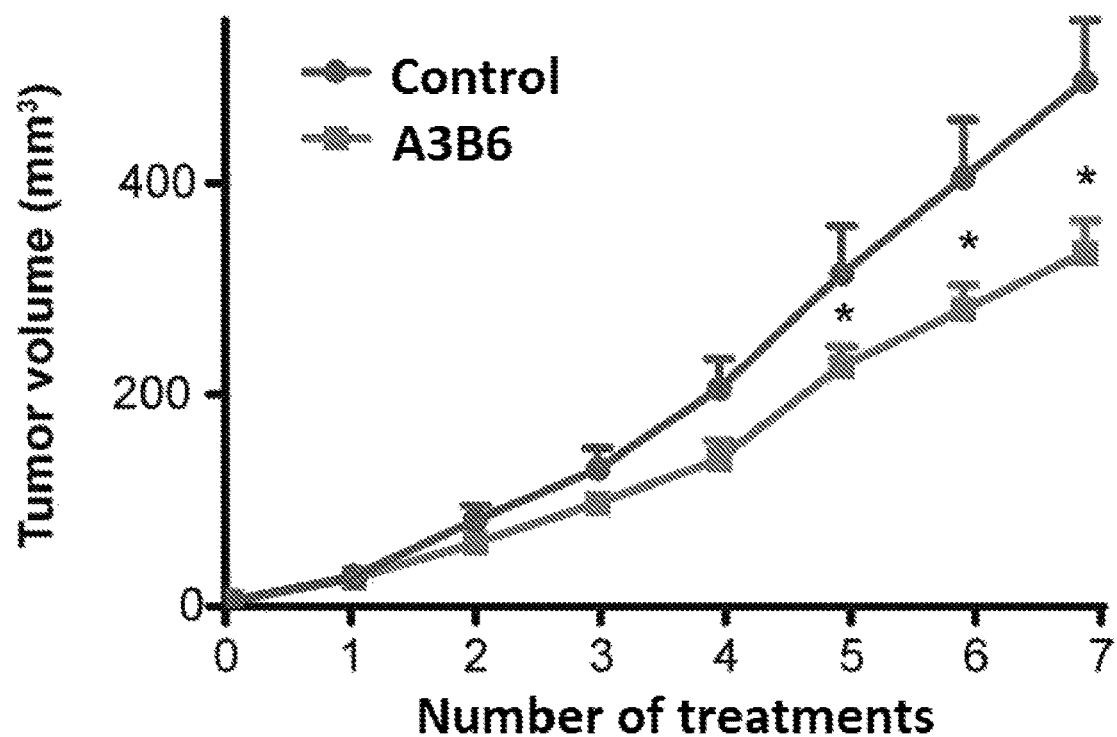
Fig. 3 cont'

F
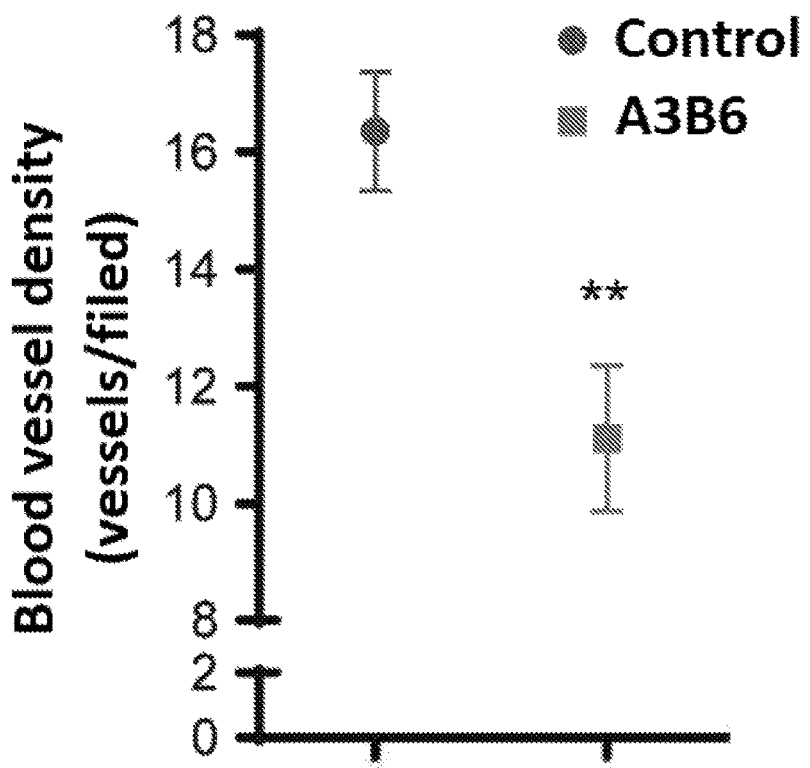
Podocalyxin
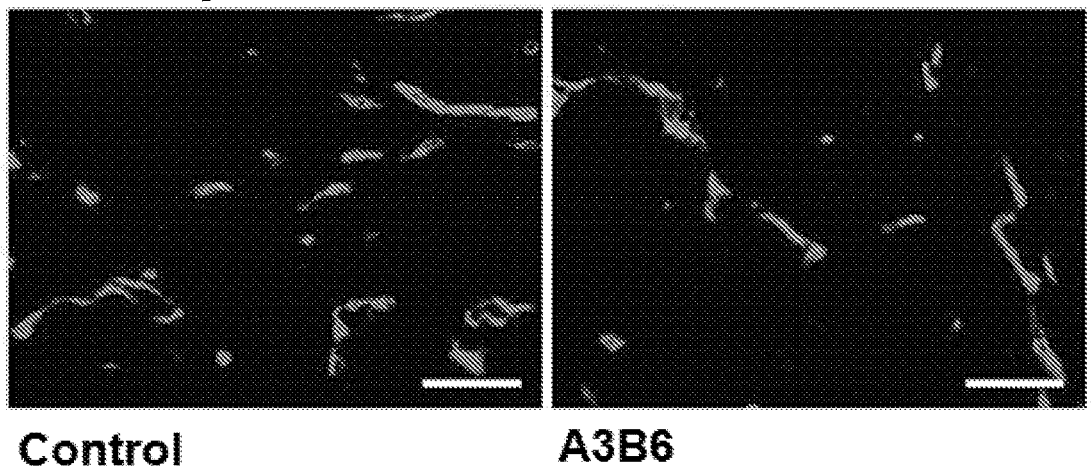
Control      A3B6
Fig. 3 cont'

A

B

C
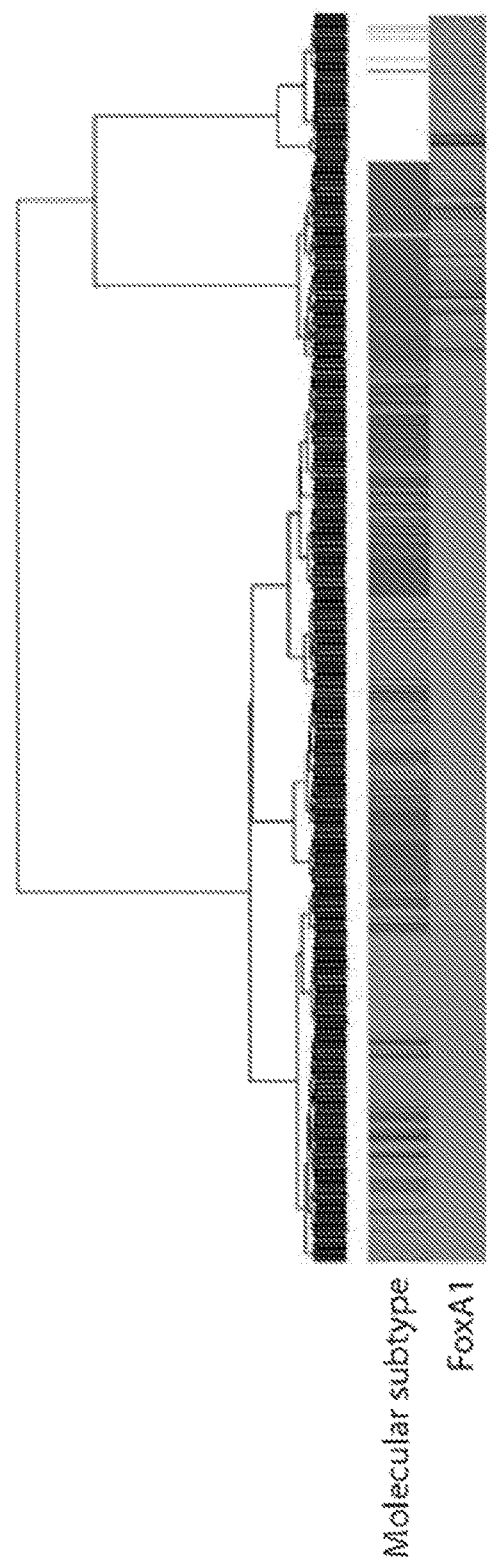
Fig. 4 cont'

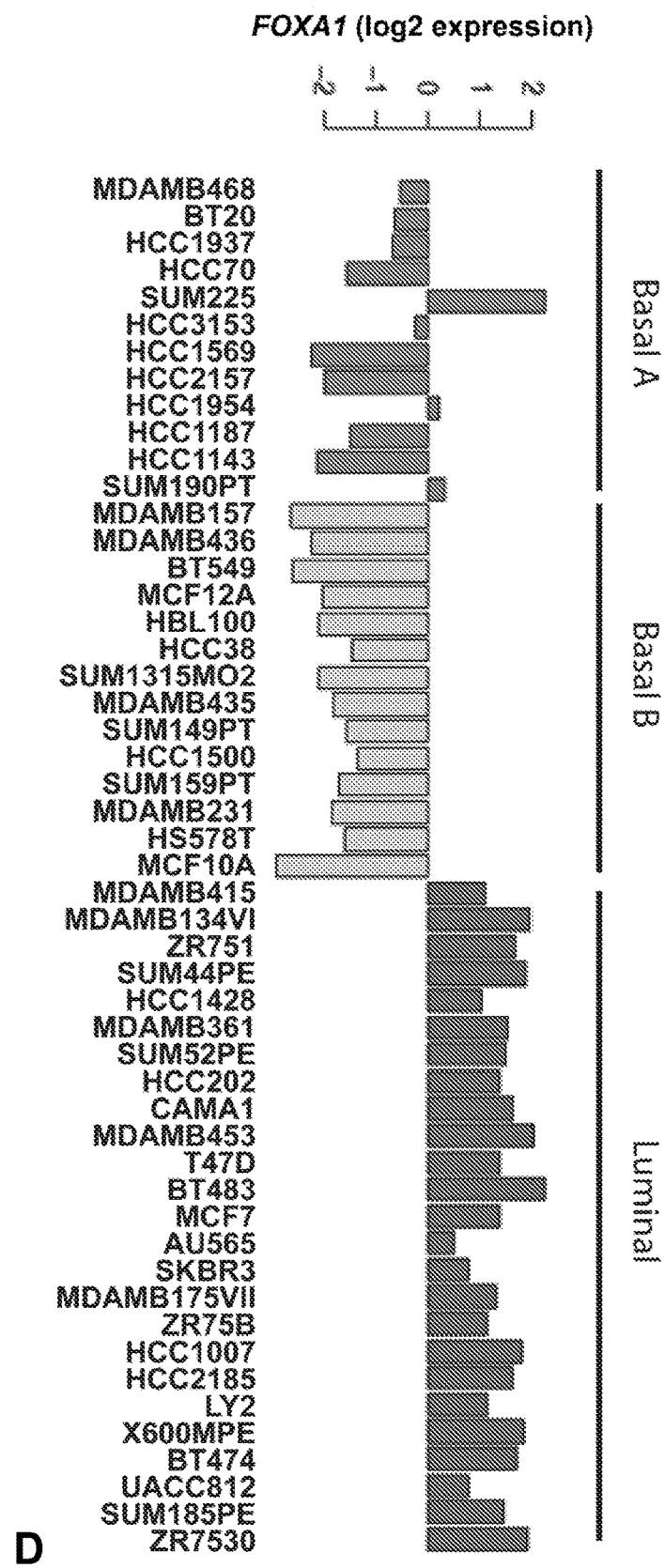
Fig. 4 cont'

E
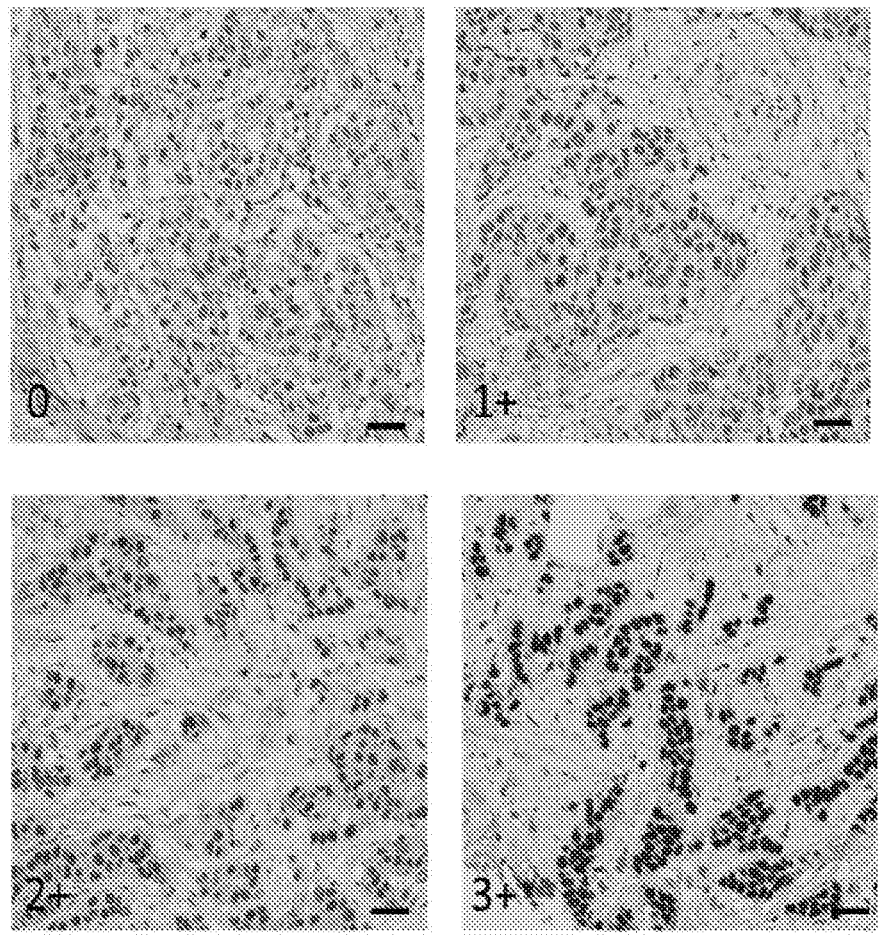
Fig. 4 cont'

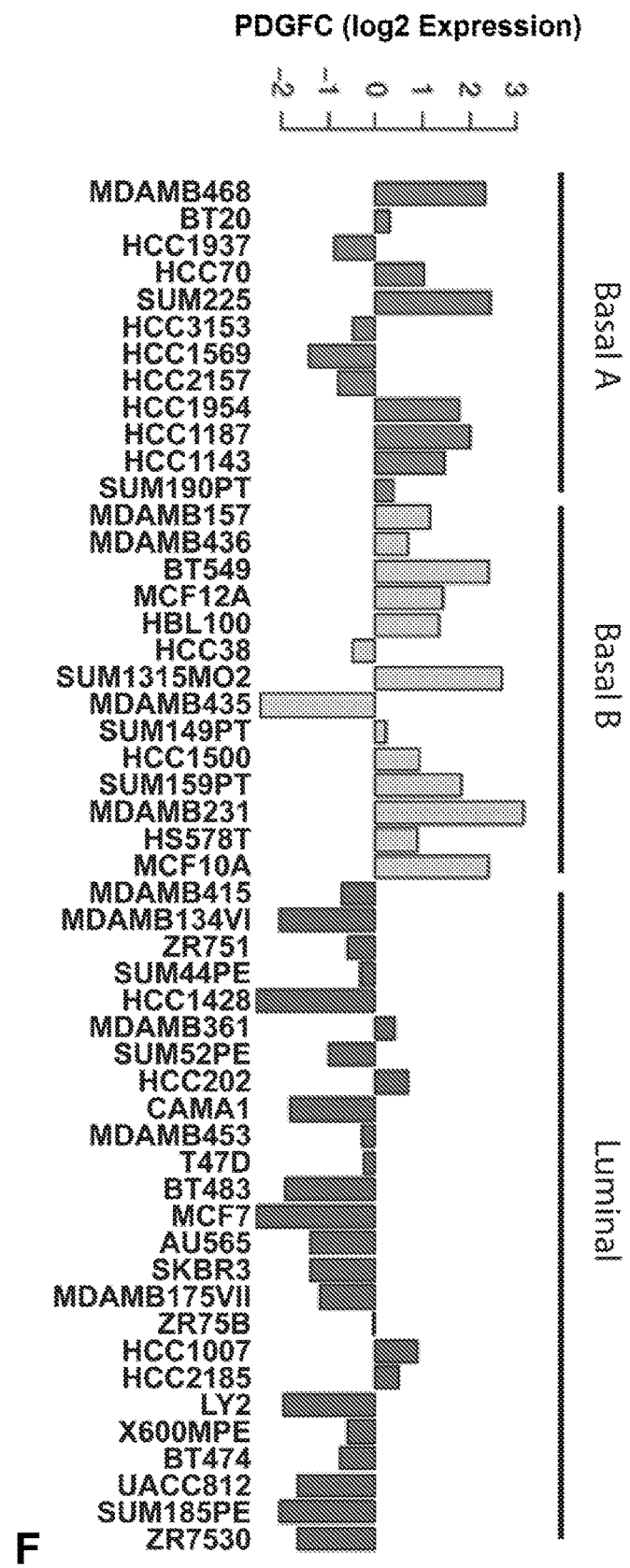
Fig. 4 cont'

G
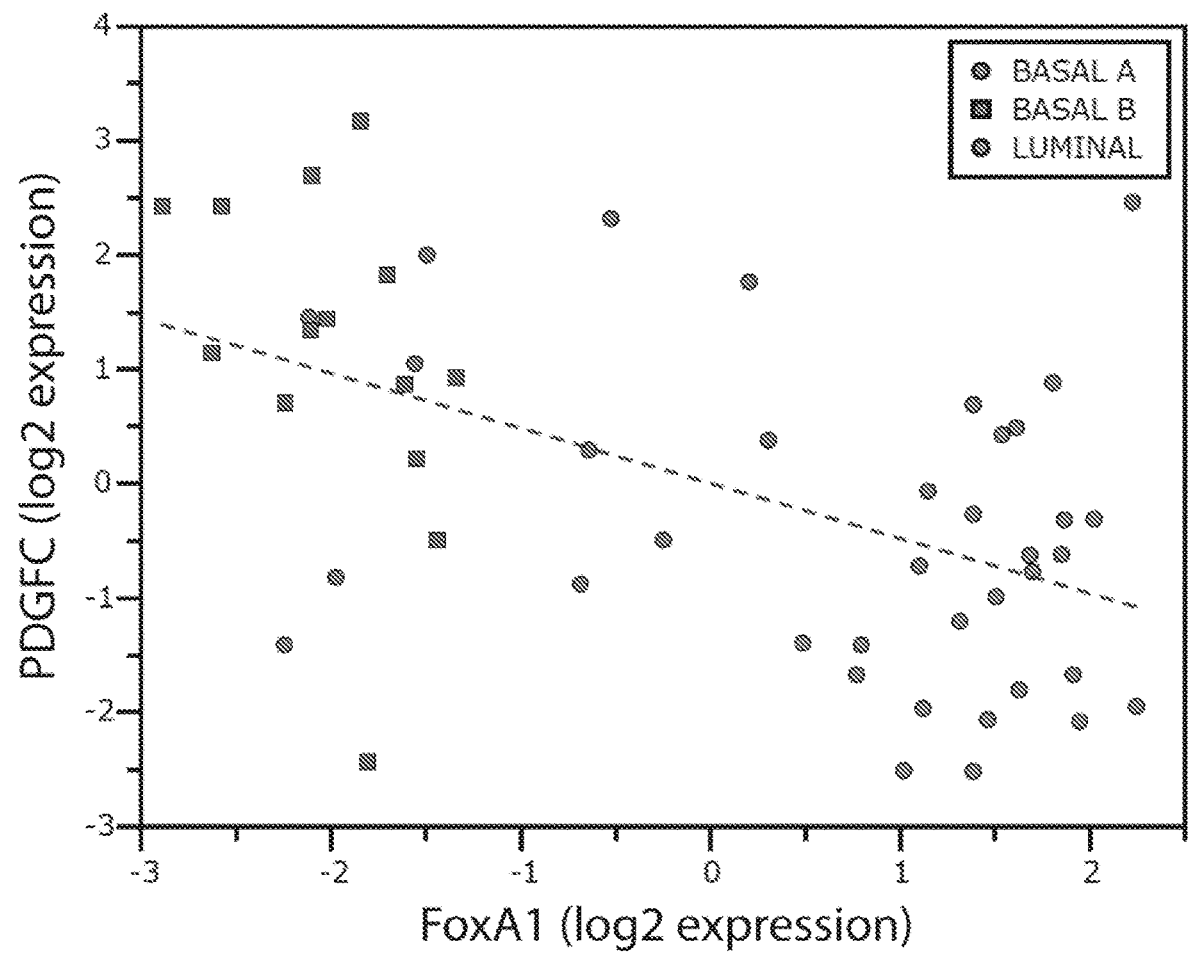
Fig. 4 cont'

A

B

C
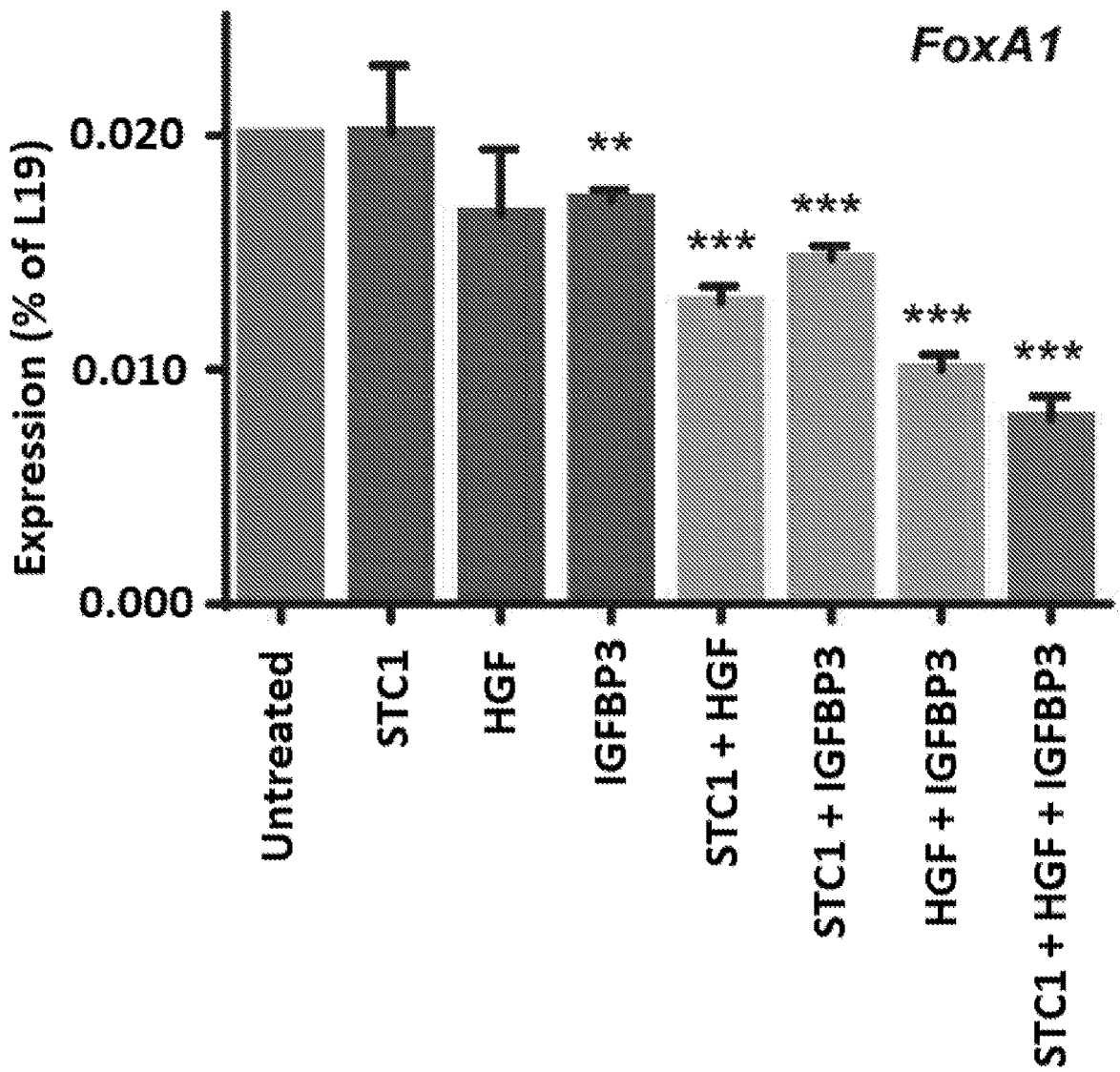
Fig. 5 cont'

D
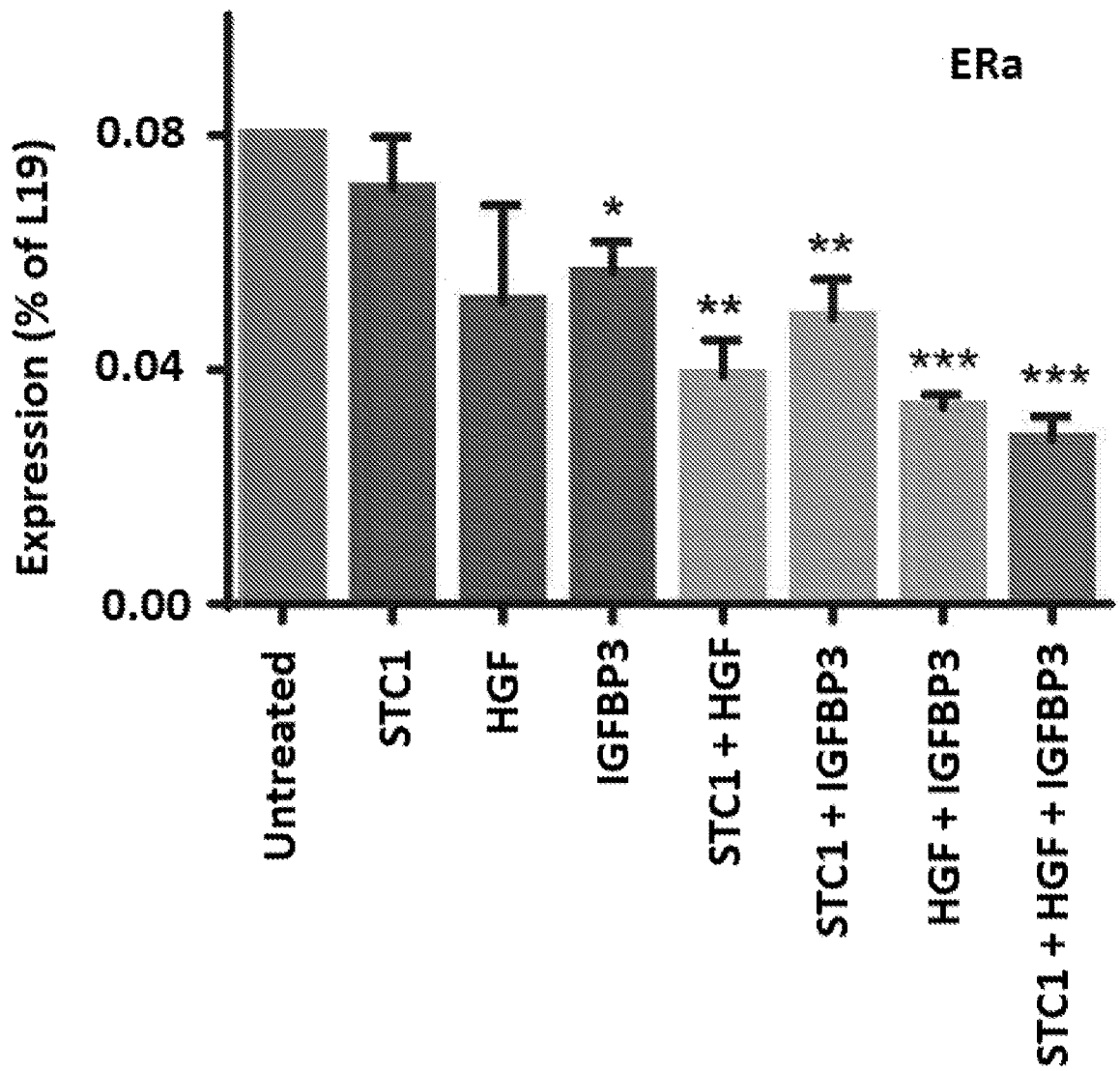
Fig. 5 cont'

E
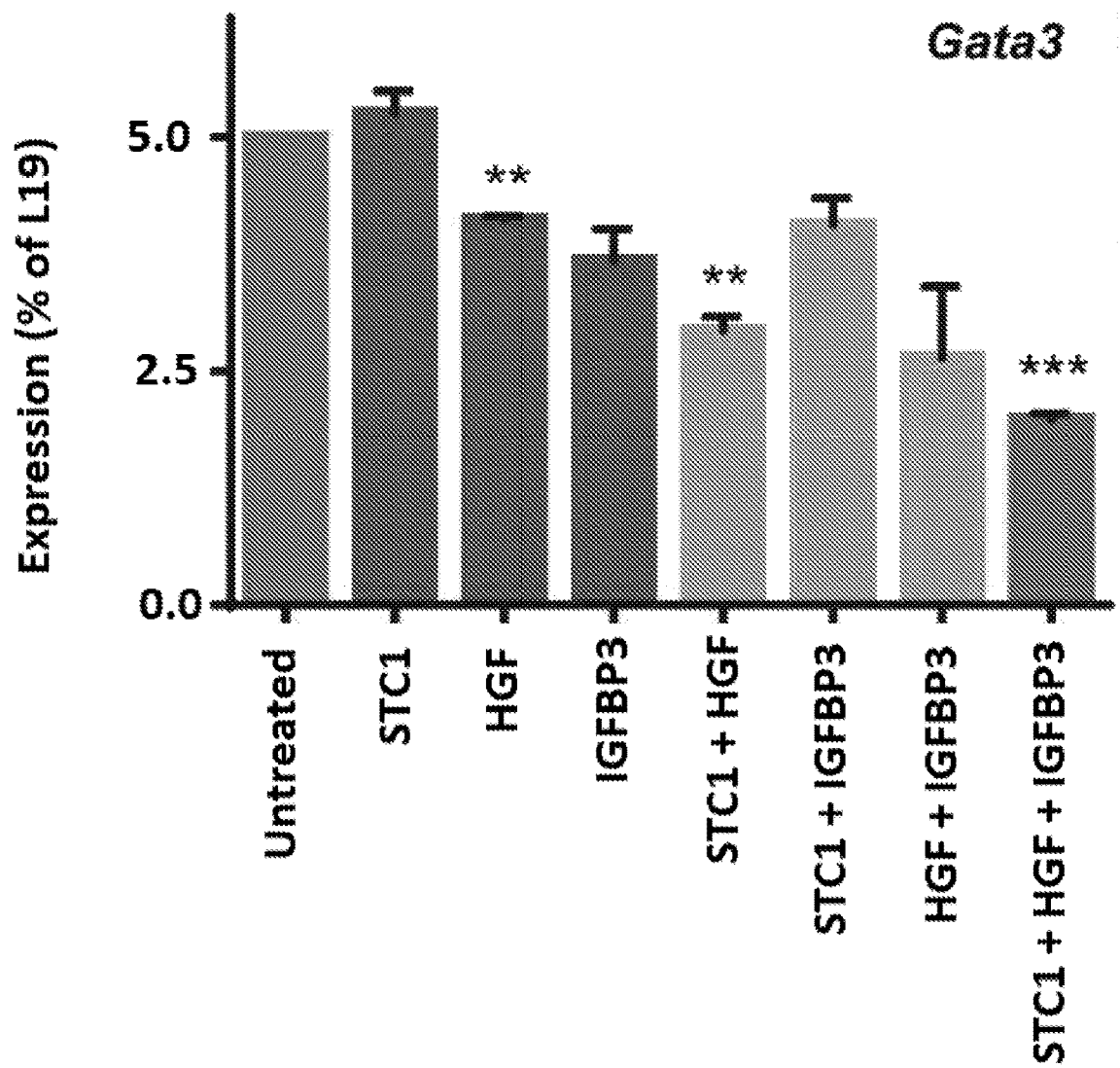
Fig. 5 cont'

F
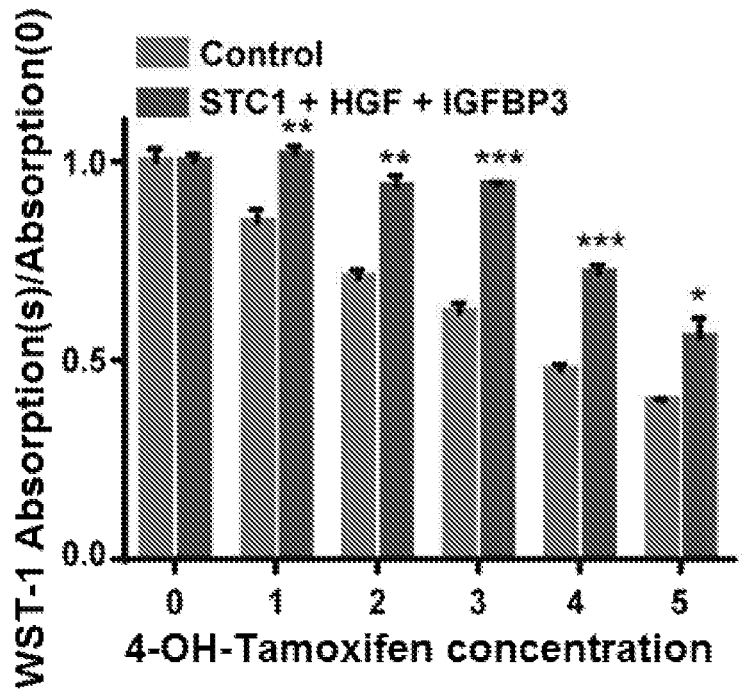
G
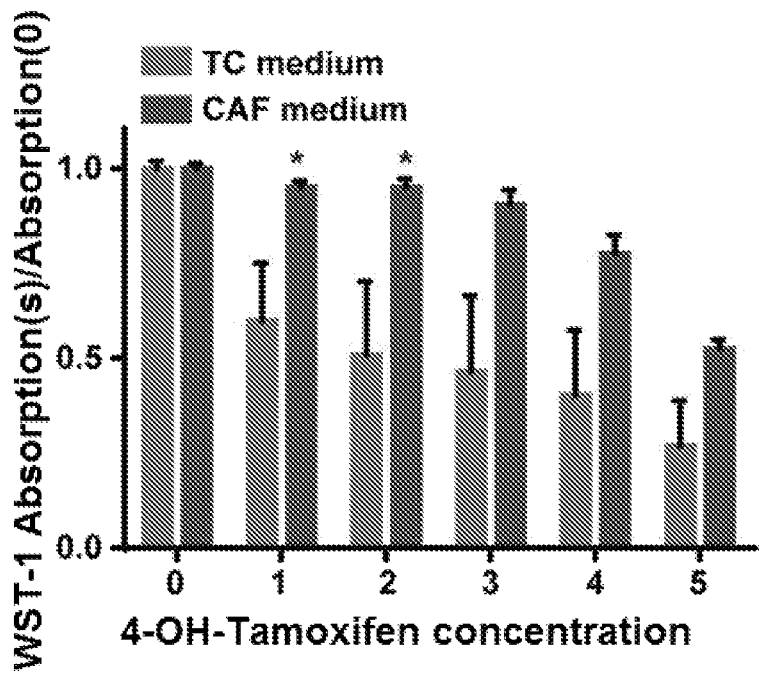
Fig. 5 cont'

H
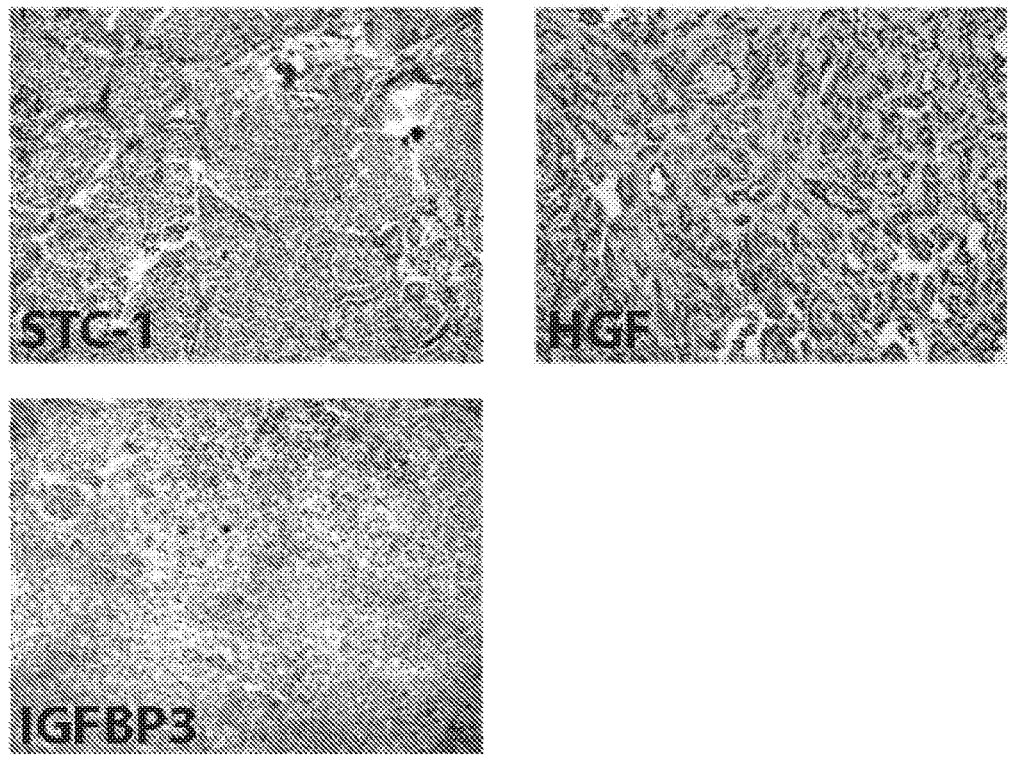
Fig. 5 cont'

C
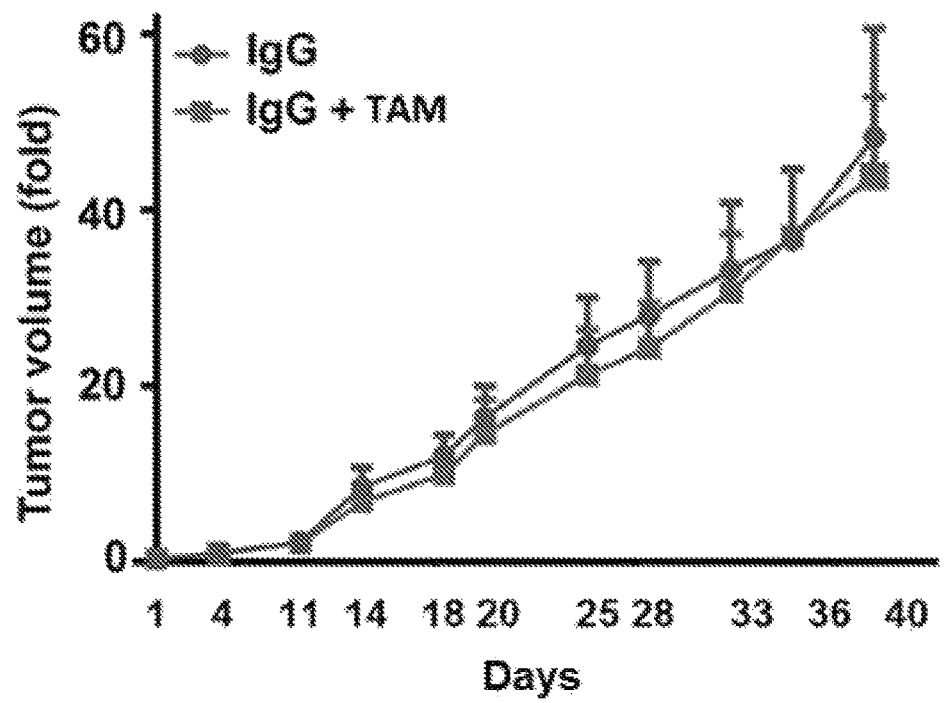
D
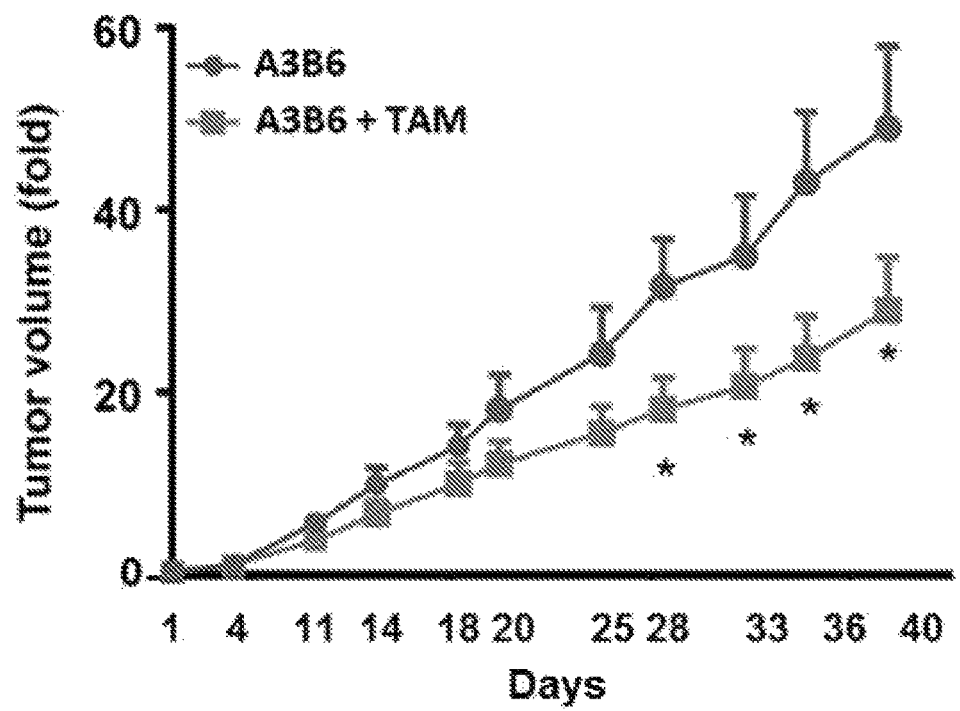
Fig. 6 cont'

E
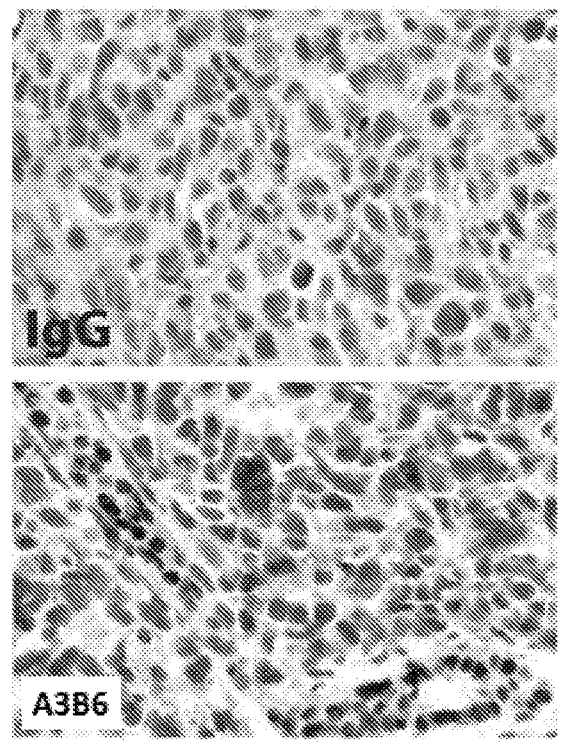
F
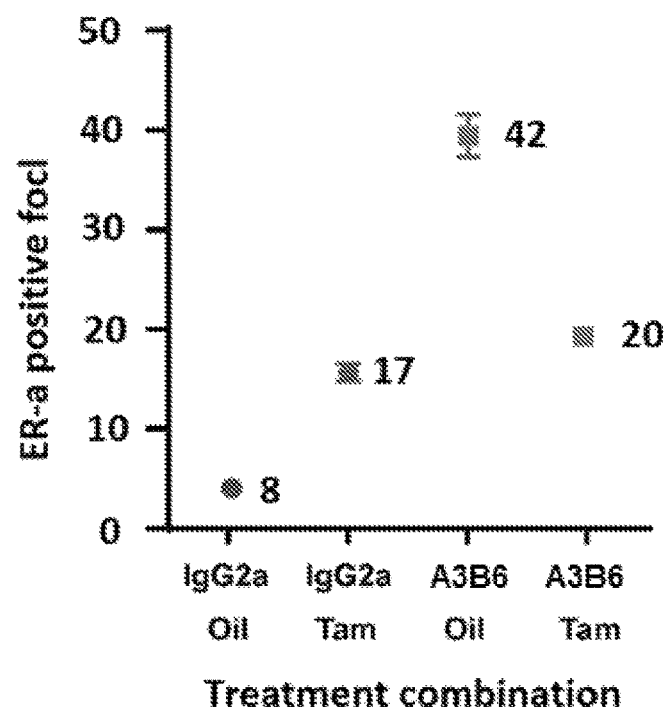
Fig. 6 cont'

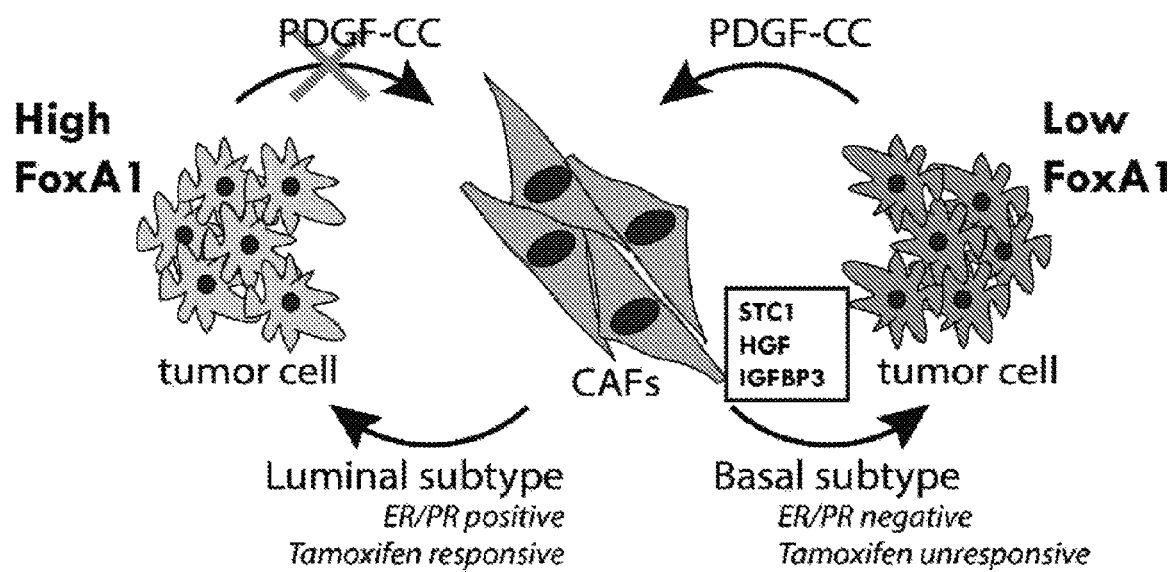
Fig. 6 cont'

TREATMENT OF ER-NEGATIVE BREAST CANCER WITH AN PDGF-CC INHIBITOR AND ANTI-ESTROGEN

CROSS REFERENCE TO RELATED APPLICATIONS

This application is a U.S. National Stage of PCT/EP2016/077295 filed Nov. 10, 2016, which depends from and claims priority to Swedish Application No: 1551455-7 filed Nov. 10, 2015 and Swedish Application No: 1650974-7 filed Jul. 4, 2016, the entire contents of each of which are incorporated herein by reference.

Sequence Listing

This application incorporate by reference a Sequence Listing as an ASCII text file entitled "Sequence_listing_corrected_ST25.txt" created on Jun. 30, 2020 having a size of 23,401 bytes.

FIELD OF INVENTION

The present invention relates to the field of treatment of cancer, and in particular to the field of treatment of ER-negative breast cancer.

BACKGROUND OF INVENTION

In the year 2012, the global incidence of breast cancer alone was 1.7 million new cases. Breast cancer can be subdivided into 5 clinically relevant subtypes: normal-like, luminal A, luminal B, HER2 and basal-like breast cancer.

The molecular subtype of breast cancer impacts on the recurrence rate and median time to recurrence. Out of all breast cancer patients, women carrying basal-like tumors have the highest recurrence rate (34% vs 20% for all other subtypes) and the shortest median time to recurrence (2.6 years vs 5 years for all other subtypes). Thus, the prognosis for women carrying basal-like breast cancers is the worst among all subtypes and the only therapeutic option offered today is high-dose chemotherapy; a treatment regimen that is accompanied by severe side effects. Endocrine therapy which is associated with mild side effects compared to high-dose chemotherapy is not effective against basal-like tumors.

Women diagnosed with breast cancers characterized by the absence of expression of the estrogen receptor (ER-negative breast cancer) are not treated with anti-hormonal agents, because such therapies have proven not effective for ER-negative breast cancers. For example a meta-analysis conducted by Early Breast Cancer Trialists' Collaborative Group (EBCTCG) published in the Lancet 2011 (doi: 10.1093/annonc/mds194) concludes that in ER-negative disease, tamoxifen had little or no effect on breast cancer recurrence or mortality. Similarly, several other studies have shown that adjuvant treatment with anti-estrogens is not effective in treatment of triple-negative breast cancer (see e.g. Foulkes et al. (doi: 10.1056/NEJMra1001389); Joensuu et al. (doi: 10.1093/annonc/mds194); Baselga et al. (doi: 10.1200/JCO.2012.46.2408); Clifford et al. (doi: 10.1634/theoncologist.2011-S1-01); Liedtke et al., (doi: 10.1200/JCO.2007.14.4147)).

SUMMARY OF INVENTION

Accordingly, there is a great need for improved treatment of ER-negative breast cancer.

Interestingly, the present invention discloses that ER-negative breast cancers can be converted into ER-positive breast cancers, such as to a breast cancer of luminal-like phenotype by treatment with anti-PDGF-CC antibodies. ER-positive breast cancers, including luminal-like breast cancers can be treated with anti-estrogen treatment. On this basis the invention discloses that surprisingly, ER-negative breast cancers can be treated with anti-estrogen treatment, if the treatment is combined with treatment with anti-PDGF-CC antibodies. Said treatment may for example be an adjuvant treatment, for example a treatment aiming at reducing the risk of relapse of a breast cancer after removal of the primary tumor by surgery.

Accordingly, the present invention provides kits-of-parts comprising an anti-PDGF-CC antibody and an anti-estrogen for the treatment of ER-negative breast cancer in an individual in need thereof.

The invention also provides kit-of-parts comprising an inhibitor of PDGF-R and an anti-estrogen for the treatment of ER-negative breast cancer in an individual in need thereof.

The invention also provides methods for treatment of ER-negative breast cancer in an individual in need thereof, said method comprising administering an anti-PDGF-CC antibody and an anti-estrogen to said individual either simultaneously or sequentially in any order, thereby treating the ER-negative breast cancer.

The invention also provides methods for treatment of ER-negative breast cancer in an individual in need thereof, said method comprising administering an inhibitor of PDGF-R and an anti-estrogen to said individual either simultaneously or sequentially in any order, thereby treating the ER-negative breast cancer.

The invention also provides methods for sensitizing a ER-negative breast cancer to anti-estrogen treatment, said method comprising administering an anti-PDGF-CC to an individual suffering from ER-negative breast, thereby sensitizing said ER-negative breast cancer to anti-estrogen treatment.

The invention also provides methods for sensitizing an ER-negative breast cancer to anti-estrogen treatment, said method comprising administering an inhibitor of PDGF-R to an individual suffering from ER-negative breast, thereby sensitizing said ER-negative breast cancer to anti-estrogen treatment.

The invention also provides methods of converting a ER-negative breast cancer to an ER-positive breast cancer, said method comprising administering an anti-PDGF-CC to an individual suffering from ER-negative breast, thereby converting said ER-negative breast cancer to an ER-positive breast cancer.

The invention also provides methods of reducing the risk of relapse of an ER-negative breast cancer in an individual having suffered from ER-negative breast cancer, wherein said breast cancer in said individual has been treated by surgery, said method comprising
  a. Sensitizing the ER-negative breast cancer to treatment with anti-estrogen by administering an anti-PDGF-CC antibody to an individual suffering from ER-negative breast cancer;
  b. administering an anti-estrogen to said individual The invention also provides methods of reducing the risk of relapse of an ER-negative breast cancer in an individual having suffered from ER-negative breast cancer, wherein said breast cancer in said individual has been treated by surgery, said method comprising
  a. sensitizing the ER-negative breast cancer to treatment with anti-estrogen by administering an inhibitor of PDGF-R to an individual suffering from ER-negative breast cancer;
  b. administering an anti-estrogen to said individual thereby reducing the risk of relapse of said ER-negative breast cancer.

The invention also provides kits-of-parts comprising an anti-PDGF-CC antibody and an anti-estrogen for use in above-mentioned methods.

DETAILED DESCRIPTION OF THE INVENTION

Definitions

Figure 1:
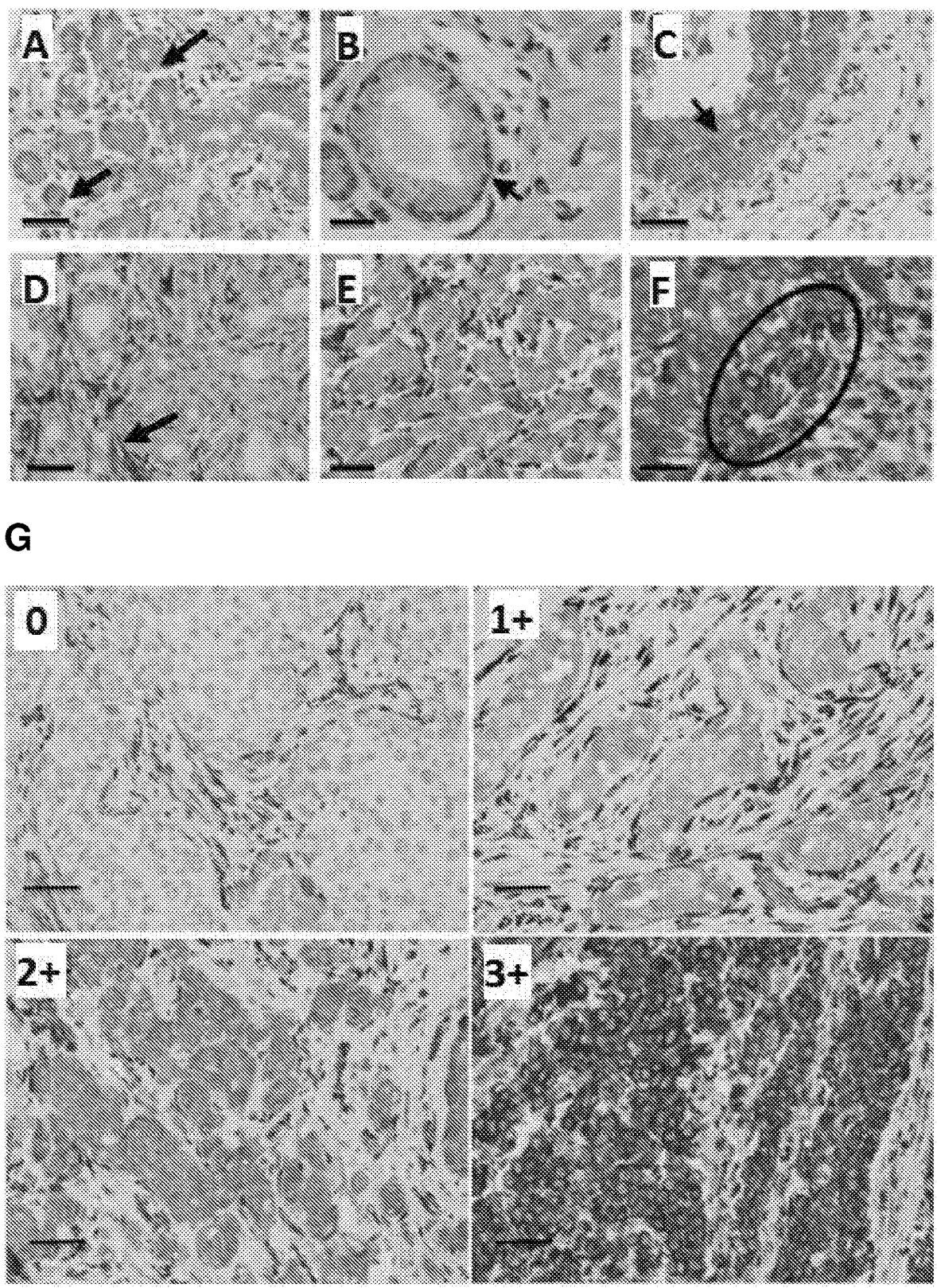
FIG. 1 shows expression of PDGF-CC. Panel A and B shows expression in normal breast tissue. Panels C to F shows expression in breast tumors. Panel G shows expression correlated to clinicopathological parameters. Panel H shows months survival in patients having moderate to high expression of PDGF-C compared to PDGF-C negative patients. Panel I shows expression of PDGFR.

The term "antibody" as used herein is a polypeptide or protein capable of recognizing and binding an antigen comprising at least one antigen binding site. Said antigen binding site preferably comprises at least one CDR. The antibody may be a naturally occurring antibody, a fragment of a naturally occurring antibody or a synthetic antibody.

The term "antigen" as used herein refers to a molecule comprising at least one epitope. The antigen may for example be a polypeptide, polysaccharide, protein, lipoprotein or glycoprotein.

The term "Basal-like breast cancer" as used herein refers to a breast cancer of a triple-negative phenotype, i.e. said cancer does not express estrogen receptor (ER), progesterone receptor (PR) and human epidermal growth factor receptor (HER)-2 at detectable levels. Furthermore, basal-type breast cancer typically does not express FoxA1. Basal-like breast cancer is associated with high grade, poor prognosis, and younger patient age.

The term "epitope" as used herein refers to a determinant capable of specific binding to an antibody. Within the present invention the epitope may be comprised within PDGF-C or PDGF-CC. Epitopes usually consist of chemically active surface groupings of molecules such as amino acids and usually have specific three dimensional structural characteristics, as well as specific charge characteristics. Epitopes may be conformational or nonconformational, wherein binding to the former but not the latter is lost in the presence of denaturing solvents. Epitopes may be continuous or discontinuous, wherein a discontinous epitope is a conformational epitope on a protein antigen which is formed from at least two separate regions in the primary sequence of the protein.

The term "ER-negative breast cancer" refers to a breast cancer lacking expression of the estrogen receptor. A breast cancer is considered an ER-negative breast cancer, when=<10% of the tumor cells of said breast cancer express estrogen receptor at levels detectable by immunohistochemistry. Preferably, an ER-negative breast cancer is a breast cancer, where <1% of the tumor cells of said breast cancer express estrogen receptor at levels detectable by immunohistochemistry.

The term "ER-positive breast cancer" refers to a breast cancer expressing the estrogen receptor. A breast cancer is considered an ER-positive breast cancer, when >10% of the tumor cells of said breast cancer express estrogen receptor at levels detectable by immunohistochemistry.

The term "luminal-like breast cancer" refers to a breast cancer which is responsive to anti-estrogen therapy. In particular, a "luminal-like breast cancer" expresses the estrogen receptor (ER). A "lumical-like breast cancer" according to the present invention may be true luminal breast cancer, such as a luminal A or luminal B breast cancer.

The term "naturally occurring antibody as used herein refers to heterotetrameric glycoproteins capable of recognizing and binding an antigen and comprising two identical heavy (H) chains and two identical light (L) chains interconnected by disulfide bonds. Each heavy chain comprises a heavy chain variable region (abbreviated herein as $V_H$) and a heavy chain constant region (abbreviated herein as $C_H$). Each light chain comprises a light chain variable region (abbreviated herein as $V_L$) and a light chain constant region (abbreviated herein as $C_L$). The $V_H$ and $V_L$ regions can be further subdivided into regions of hypervariability, termed complementarity determining regions (CDRs), interspersed with regions that are more conserved, termed framework regions (FRs). Antibodies may comprise several identical heterotetramers.

The term "treatment" as used herein may refer to any kind of treatment. The treatment may be a curative treatment, it may also be an ameliorating treatment and/or a treatment reducing the effects of the cancer. The treatment may also be a treatment which delays progression of the cancer, for example the treatment may reduce the growth of cancer, reduce metastasis or in other ways delay cancer progression. The treatment may also be a treatment to reduce the risk of relapse.

Method of Treatment

The present invention provides methods for treatment of ER-negative breast cancers in an individual in need thereof. The methods of the invention comprise administering an anti-PDGF-CC antibody and an anti-estrogen to an individual suffering from ER-negative breast cancer either simultaneously or sequentially in any order, thereby treating the ER-negative breast cancer.

The present disclosure also provides methods for treatment of ER-negative breast cancers in an individual in need thereof, the methods comprising administering an inhibitor of PDGF-R and an anti-estrogen to an individual suffering from ER-negative breast cancer either simultaneously or sequentially in any order, thereby treating the ER-negative breast cancer.

The method of treatment according to the invention may be combined with one or more conventional methods for treatment of ER-negative breast cancer. Thus, the methods of the invention may comprise a combination of treatment with an anti-PDGF-CC antibody and an anti-estrogen combined with one or more additional methods. The methods of the invention may also comprise a combination of treatment with an inhibitor of PDGF-R and an anti-estrogen combined with one or more additional methods. For example, said ER-negative breast cancer may be treated by a method selected from the group consisting of surgery, irradiation and chemotherapy. In particular the individual to be treated with the methods of the invention may be an individual suffering from ER-negative breast cancer, wherein said individual has already been subjected to treatment of said breast cancer by surgery. Thus, the individual to be treated may be an individual who has suffered from ER-negative breast cancer, wherein the primary tumor has been removed by surgery. In such cases, the treatment of the present invention can frequently be considered an adjuvant therapy, which reduces the risk of relapse. In particular, the treatment may be a treatment to reduce the risk of relapse within 5 years from onset of the treatment. For example, the treatment may be treatment to prevent relapse within 5 years from the onset of treatment. Preferably, the treatment with anti-PDGF-CC antibodies and anti-estrogen is initiated at the latest 1 months after surgery, for example at the latest one week after surgery. Treatment may be initiated earlier, for example even prior to surgery. Similarly, the treatment with inhibitors of PDGF-R and anti-estrogen is initiated at the latest 1 month after surgery, for example at the latest one week after surgery. Treatment may be initiated earlier, for example even prior to surgery.

It is also comprised within the present invention that the individual to be treated with anti-PDGF-CC antibodies and anti-estrogen, or the individual to be treated with inhibitors of PDGF-R and anti-estrogen have not been subjected to surgery. This may be because the particular breast cancer is an inoperable breast cancer, a breast cancer less suitable for removal by surgery or because the individual has not yet undergone surgery. Such treatment may for example be a neoadjuvant treatment.

The anti-PDGF-CC antibody may be any antibody capable of binding PDGF-CC, for example any of the antibodies described herein below in the section "anti-PDGF-CC antibody". The anti-estrogen may be any compound having an anti-estrogen effect, for example any of the compounds described herein below in the section anti-estrogen.

The invention also provides methods for sensitizing an ER-negative breast cancer to anti-estrogen treatment. ER-negative breast cancers are not responsive to anti-estrogen treatment (see e.g. Early Breast Cancer Trialists' Collaborative Group (EBCTCG) doi: 10.1016/S0140-6736(11)60993-8), but the invention interestingly discloses that ER-negative breast cancer can be sensitized to treatment with anti-estrogen by treatment with anti-PDGF-CC antibodies.

Thus, the invention provides methods for sensitizing an ER-negative breast cancer to anti-estrogen treatment, said methods comprising administering an anti-PDGF-CC to an individual suffering from ER-negative breast cancer, thereby sensitizing said ER-negative breast cancer to anti-estrogen treatment.

The disclosure also provides methods for sensitizing an ER-negative breast cancer to anti-estrogen treatment, said methods comprising administering an inhibitor of PDGF-R to an individual suffering from ER-negative breast cancer, thereby sensitizing said ER-negative breast cancer to anti-estrogen treatment.

In particular, the invention may provide methods for sensitizing an ER-negative breast cancer to anti-estrogen treatment in an individual, wherein said individual has suffered from ER-negative breast cancer, and wherein said breast cancer in said individual has been treated by surgery, wherein following anti-estrogen treatment in said individual, no relapse is observed or the risk of relapse is significantly reduced.

A breast cancer sensitized to anti-estrogen treatment may thus be treated with anti-estrogen. The methods may thus comprise a step of administering an anti-estrogen to the individual suffering from ER-negative breast cancer, wherein said anti-PDGF-CC antibody and said anti-estrogen may be administered simultaneously or sequentially in any order.

Thus, the invention also provides methods of treatment of ER-negative breast cancer in an individual in need thereof, said method comprising a. Sensitizing an ER-negative breast cancer to treatment with anti-estrogen by administering an anti-PDGF-CC antibody to an individual suffering from ER-negative breast cancer;
b. administering an anti-estrogen to said individual thereby treating said ER-negative breast cancer.

The disclosure also provides methods of treatment of ER-negative breast cancer in an individual in need thereof, said method comprising
a. Sensitizing an ER-negative breast cancer to treatment with anti-estrogen by administering an inhibitor of PDGF-R to an individual suffering from ER-negative breast cancer;
b. administering an anti-estrogen to said individual thereby treating said ER-negative breast cancer.

The invention also provides methods of treatment of ER-negative breast cancer in an individual, wherein said individual has suffered from ER-negative breast cancer, and wherein said breast cancer in said individual has been treated by surgery, said method comprising
a. Sensitizing the ER-negative breast cancer to treatment with anti-estrogen by administering an anti-PDGF-CC antibody to an individual suffering from ER-negative breast cancer;
b. administering an anti-estrogen to said individual thereby reducing the risk of relapse of said ER-negative breast cancer.

The invention also provides methods of treatment of ER-negative breast cancer in an individual, wherein said individual has suffered from ER-negative breast cancer, and wherein said breast cancer in said individual has been treated by surgery, said method comprising
a. Sensitizing the ER-negative breast cancer to treatment with anti-estrogen by administering an inhibitor of PDGF-R to an individual suffering from ER-negative breast cancer;
b. administering an anti-estrogen to said individual thereby reducing the risk of relapse of said ER-negative breast cancer.

The invention also provides methods of treatment of ER-negative breast cancer in an individual in need thereof, said method comprising
a. Sensitizing the ER-negative breast cancer to treatment with anti-estrogen by administering an anti-PDGF-CC antibody to an individual suffering from ER-negative breast cancer;
b. Treatment of said ER-negative breast cancer by surgery
c. Sensitizing remaining ER-negative breast cancer to treatment with anti-estrogen by administering an anti-PDGF-CC antibody to an individual suffering from ER-negative breast cancer
d. administering an anti-estrogen to said individual
thereby reducing the risk of relapse of said ER-negative breast cancer.

The invention also provides methods of treatment of ER-negative breast cancer in an individual in need thereof, said method comprising
a. Sensitizing the ER-negative breast cancer to treatment with anti-estrogen by administering an inhibitor of PDGF-R to an individual suffering from ER-negative breast cancer;
b. Treatment of said ER-negative breast cancer by surgery
c. Sensitizing remaining ER-negative breast cancer to treatment with anti-estrogen by administering an inhibitor of PDGF-R to an individual suffering from ER-negative breast cancer
d. administering an anti-estrogen to said individual
thereby reducing the risk of relapse of said ER-negative breast cancer.

The invention also provides methods of converting an ER-negative breast cancer to a ER-positive breast cancer. Such methods comprise administering an anti-PDGF-CC to an individual suffering from ER-negative breast cancer, thereby converting said ER-negative breast cancer to an ER-positive breast cancer.

The invention also provides methods of converting an ER-negative breast cancer to a luminal-like breast cancer. Such methods comprise administering an anti-PDGF-CC to an individual suffering from ER-negative breast cancer, thereby converting said ER-negative breast cancer to a luminal-like breast cancer.

A breast cancer is considered to be a luminal-like breast cancer, when said cancer is expressing the estrogen receptor (ER) at detectable levels. It is preferred that at least 1%, such as at least 10% of the breast cancer cells of said breast cancer are expressing ER at detectable levels.

In some embodiments the method may comprise an additional step of testing whether the breast cancer has been converted to a luminal-like breast cancer and/or to an ER-positive breast cancer. Said test may be performed subsequent to administration of said anti-PDGF-CC antibody and may in general comprise the steps of:
a) obtaining a sample from said breast cancer
b) testing expression of estrogen receptor (ER) in said sample
c) wherein detectable expression of ER in said sample is indicative of that said breast cancer has been converted to a luminal-like breast cancer or an ER-positive breast cancer.

Said test may be any test useful for determining whether a breast cancer expresses ER. In one embodiment the test is an immunohistochemical test, for example a test, wherein step b) involves staining the sample obtained in step a) with the aid of antibodies recognizing ER, and followed by detection of ER expression e.g. by microscopy. If a larger percentage of cells express ER than in the initial ER-negative tumor (e.g. if more than 1% of the tumor cells express ER) then ER may be considered expressed. Preferably, if at least 10% of tumor cells of said sample expressed ER, then the breast cancer is considered ER-positive.

Thus, the invention provides methods of treatment of ER-negative breast cancer in an individual in need thereof, said method comprising
a. converting a ER-negative breast cancer to a luminal-like breast cancer by administering an anti-PDGF-CC antibody to an individual suffering from ER-negative breast cancer;
b. administering an anti-estrogen to said individual thereby treating said ER-negative breast cancer.

The methods of the invention may comprise the steps of administering an anti-PDGF-CC antibody and an anti-estrogen. Said anti-PDGF-CC antibody and said anti-estrogen may be administered simultaneously or sequentially in any order.

The methods of the invention may in alternative comprise the steps of administering an inhibitor of PDGF-R and an anti-estrogen. Said inhibitor of PDGF-R and said anti-estrogen may be administered simultaneously or sequentially in any order.

The invention also provides kits-of-parts comprising
a) an anti-PDGF-CC antibody and an anti-estrogen, or
b) an inhibitor of PDGF-R and an anti-estrogen for treatment of ER-negative breast cancer in an individual, wherein said individual has suffered from ER-negative breast cancer, and wherein said breast cancer in said individual has been treated by surgery, and wherein said treatment reduces the risk of relapse.

In some embodiments of the invention said anti-PDGF-CC antibody or said inhibitor of PDGF-R is administered to said individual simultaneously with administration of said anti-estrogen.

In some embodiments it may however be preferred that the anti-PDGF-CC antibody or the inhibitor of PDGF-R is administered to said individual prior to administration of said anti-estrogen. Such an order of administration may ensure that the ER-negative breast cancer is sensitized to anti-estrogen prior to administration of said anti-estrogen.

In some embodiments of the invention the anti-PDGF-CC antibody or the inhibitor of PDGF-R is administered more than once, for example it may be administered at least twice, such as at least 3 times, for example in the range of 1 to 20 times, such as in the range of 2 to 10 times.

In one embodiment, the anti-PDGF-CC antibody or the inhibitor of PDGF-R is administered at least twice to an individual suffering from ER-negative breast cancer, wherein one or more administrations are prior to treatment by surgery, and one or more additional administrations are administered post treatment by surgery. The administration(s) after surgery may be simultaneous with anti-estrogen treatment.

Similarly, anti-estrogen may be administered more than once. Many anti-estrogens are administered over an extended period of time, for example once daily, twice daily or even more frequently for an extended period of time. Anti-estrogens may also be administered less frequently, e.g. in the range of 1 to 6 times per week, or for example in the range of 1 to 4 times per months. Thus, administration of an anti-estrogen may be very frequent over an extended period of time, for example for at least 1 month, such as for at least 6 months, for example for at least 1 year, such as for several years. For example the anti-estrogen treatment may be once daily for at least 1 year, for example of in the range 1 to 10 years, such as in the range of 4 to 6 years, such as for 5 years. In such embodiments, the first administration of anti-estrogen may be simultaneous with at least one administration of anti-PDGF-CC antibodies or inhibitors of PDGF-R, whereas subsequent administrations may be performed individually. It is also possible that each administration of anti-PDGF-CC antibody or inhibitors of PDGF-R is performed simultaneously with an administration of anti-estrogen, but that anti-estrogens in addition are administered separately.

In one embodiment of the invention the anti-PDGF-CC antibody or the inhibitor of PDGF-R is administered at least once prior to the first administration of anti-estrogen. Thus, the first dosage of said anti-estrogen may be administered in the range of 1 hours to several weeks after the first administration of said anti-PDGF-CC antibody or of said inhibitor of PDGF-R.

Typically, the anti-estrogen is administered for a longer time than the anti-PDGF-CC antibody or the inhibitor of PDGF-R. Thus, the anti-PDGF-CC antibody or the inhibitor of PDGF-R may for example be administered at the onset of treatment, whereas the anti-estrogen typically may be administered continuously for a longer time period. Thus, as described above, the anti-PDGF-CC antibody or the inhibitor of PDGF-R may for example be administered in the range of 1 to 5 times, whereas the anti-estrogen typically may be administered continuously for in the range of 1 to 10 years, such as in the range of 4 to 6 years, such as for 5 years.

The last administration of anti-estrogen is preferably given later than the last administration of anti-PDGF-CC antibody or inhibitor of PDGF-R.

The route of administration may be chosen according to the particular anti-PDGF-CC antibody, inhibitor of PDGF-R and the anti-estrogen. Frequently, the anti-PDGF-CC antibody or the inhibitor of PDGF-R is administered parenterally. Inhibitors of PDGF-R can be administered parenterally, for example as intravenous formulation, and also enetrally, for example orally in the form of tablets. Methods and useful formulations for parenteral administration are described below in the section "Pharmaceutical formulation". The anti-estrogen may be administered by any useful route, which may be chosen according to the particular anti-estrogen used. Frequently, the anti-estrogen is administered orally. Methods and useful formulations for oral administration are described below in the section "Pharmaceutical formulation".

The individual to be treated may be any individual suffering from ER-negative breast cancer. Frequently, the individual will be a human being, for example a male or a female human being. Preferably, the individual is a female human being.

In some embodiments the methods of the present disclosure comprise administration of an anti-PDGF-CC antibody and an anti-estrogen, wherein the anti-estrogen is an estrogen antagonist as described in the section below "Anti-estrogen".

In some embodiments the methods of the present disclosure comprise administration of an anti-PDGF-CC antibody and an anti-estrogen, wherein the anti-estrogen is an estrogen antagonist selected from the group consisting of tamoxifen, raloxifene, 4-hydroxytramoxifen, trioxifene, keoxifene, afimoxifene, LY117018, fulvestrant and toremifene.

In some embodiments the methods of the present disclosure comprise administration of an anti-PDGF-CC antibody and an estrogen antagonist, wherein the estrogen antagonist is tamoxifen.

In some embodiments the methods of the present disclosure comprise administration of an anti-PDGF-CC antibody and an anti-estrogen, wherein the anti-estrogen is an aromatase inhibitor as described in the section below "Anti-estrogen".

In some embodiments the methods of the present disclosure comprise administration of an anti-PDGF-CC antibody and an anti-estrogen, wherein the anti-estrogen is an aromatase inhibitor selected from the group consisting of exemestane, formestane, aminoglutethimide, vorozole, fadrozole, anastrozole and letrozole.

In some embodiments the methods of the present disclosure comprise administration of an anti-PDGF-CC antibody and an anti-estrogen, wherein the anti-estrogen is letrozole.

In some embodiments the methods of the present disclosure comprise administration of an inhibitor of PDGF-R and an anti-estrogen, wherein the anti-estrogen is an estrogen antagonist as described in the section below "Anti-estrogen".

In some embodiments the methods of the present disclosure comprise administration of an inhibitor of PDGF-R and an anti-estrogen, wherein the anti-estrogen is an estrogen antagonist selected from the group consisting of tamoxifen, raloxifene, 4-hydroxytramoxifen, trioxifene, keoxifene, afimoxifene, LY117018, fulvestrant and toremifene.

In some embodiments the methods of the present disclosure comprise administration of an inhibitor of PDGF-R and an anti-estrogen, wherein the anti-estrogen is tamoxifen.

Kit-of-Parts

The invention provides a kit-of-parts comprising an anti-PDGF-CC antibody and an anti-estrogen. The invention also provides a kit-of-parts comprising an inhibitor of PDGF-R and an anti-estrogen. The kit-of-part may in particular be for the treatment of ER-negative breast cancer in an individual in need thereof. Thus, the kit-of-parts may be prepared for use in any of the methods of treatment, described herein above in the section "Method of treatment".

The kit-of-parts may be provided as separate units, i.e. one or more units comprising an anti-PDGF-CC antibody and one or more units comprising an anti-estrogen, wherein the units are separately provided. Alternatively, the kit-of-parts may comprise one or more units comprising an inhibitor of PDGF-R and one or more units comprising an anti-estrogen, wherein the units are separately provided.

Thus, the kit-of-parts may be prepared for sequential administration, wherein each part of the kit-of-part are provided and administered separately. Thus, the anti-PDGF-CC antibody and the anti-estrogen may be prepared for sequential administration. Also, the inhibitor of PDGF-R and the anti-estrogen may be prepared for sequential administration. It is comprised within the invention that said kit-of-part is prepared for administration according to any of the methods described above in the section "Method of treatment". In particular, the kit-of-parts may be prepared for treatment of ER-negative breast cancer, wherein said treatment comprises the steps of a. administration of the anti-PDGF-CC antibody to an individual in need thereof;
b. subsequent administration of the anti-estrogen.

Alternatively, the kit-of-parts may be prepared for treatment of ER-negative breast cancer, wherein said treatment comprises the steps of a. administration of the inhibitor of PDGF-R to an individual in need thereof;
b. subsequent administration of the anti-estrogen.

Frequently, the anti-PDGF-CC antibody or the inhibitor of PDGF-R is prepared for parenteral administration for a limited number of times. E.g. the anti-PDGF-CC antibody or the inhibitor of PDGF-R may be prepared for parenteral administration as described herein above in the section "Method of treatment". The inhibitor of PDGF-R is also frequently prepared for oral administration, for example in the form of tablets. In contrast the anti-estrogen may be prepared by administration by any means. Thus, for example the anti-estrogen may be prepared for frequent oral administration as described herein above in the section "Method of treatment".

In some embodiments the kit-of-parts of the present disclosure comprises an anti-PDGF-CC antibody and an anti-estrogen, wherein the anti-estrogen is an estrogen antagonist as described in the section below "Anti-estrogen".

In some embodiments the kit-of-parts of the present disclosure comprises an anti-PDGF-CC antibody and an anti-estrogen, wherein the anti-estrogen is an estrogen antagonist selected from the group consisting of tamoxifen, raloxifene, 4-hydroxytramoxifen, trioxifene, keoxifene, afimoxifene, LY117018, fulvestrant and toremifene.

In some embodiments the kit-of-parts of the present disclosure comprises an anti-PDGF-CC antibody and an anti-estrogen, wherein the anti-estrogen is tamoxifen.

In some embodiments the kit-of-parts of the present disclosure comprises an anti-PDGF-CC antibody and an anti-estrogen, wherein the anti-estrogen is an aromatase inhibitor as described in the section below "Anti-estrogen".

In some embodiments the kit-of-parts of the present disclosure comprises an anti-PDGF-CC antibody and an anti-estrogen, wherein the anti-estrogen is an aromatase inhibitor selected from the group consisting of exemestane, formestane, aminoglutethimide, vorozole, fadrozole, anastrozole and letrozole.

In some embodiments the kit-of-parts of the present disclosure comprises an anti-PDGF-CC antibody and an anti-estrogen, wherein the anti-estrogen is letrozole In some embodiments the kit-of-parts of the present disclosure comprises an inhibitor of PDGF-R and an anti-estrogen, wherein the anti-estrogen is an estrogen antagonist as described in the section below "Anti-estrogen".

In some embodiments the kit-of-parts of the present disclosure comprises an inhibitor of PDGF-R and an anti-estrogen, wherein the anti-estrogen is an estrogen antagonist selected from the group consisting of tamoxifen, raloxifene, 4-hydroxytramoxifen, trioxifene, keoxifene, afimoxifene, LY117018, fulvestrant and toremifene.

In some embodiments the kit-of-parts of the present disclosure comprises an inhibitor of PDGF-R and an anti-estrogen, wherein the anti-estrogen is tamoxifen.

Anti-PDGF-CC Antibody

The present invention relates to a kit-of-part comprising an anti-PDGF-CC antibody as well as to methods of treatment employing an anti-PDGF-CC antibody. Said anti-PDGF-CC antibody may be any antibody capable of binding PDGF-CC, in particular it may be an antibody specifically binding PDGF-CC. PDGF-CC is described in detail in the section "PDGF-CC" herein below. Since PDGF-CC is a dimer of PDGF-C, and accordingly, the anti-PDGF-CC antibody may specifically bind both PDGF-CC and PDGF-C.

The present invention relates also to a kit-of-part comprising an inhibitor of PDGF-R as well as to methods of treatment employing an inhibitor of PDGF-R. However, use of an anti-PDGF-CC antibody is preferred as the antibody targets with great specificity PDGF-CC, but not other members of the PDGF family and therefore side effects are minimal. Inhibitors of PDGF-R are also effective in blocking the PDGF-R signaling pathways, but they act non-specifically on all the PDGF-R and may so result in undesired effects. However, such undesired effects are minimized when the inhibitor of PDGF-R is an antibody against PDGF-R.

The anti-PDGF-CC antibodies may bind to any PDGF-CC. However, in general it is preferred that the anti-PDGF-CC antibodies to be used are capable of binding PDGF-CC of the individual to be treated. Accordingly, in embodiments of the invention where the individual is a human being, then it is preferred that the anti-PDGF-CC antibodies are capable of binding human PDGF-CC. The sequence of human PDGF-C is provided as SEQ ID NO:1 herein.

The anti-PDGF-CC antibody according to the present invention may be any polypeptide or protein capable of recognizing and binding PDGF-CC. By the term "specifically binding" is meant binding with at least 10 times higher affinity to PDGF-CC than to a non-specific antigen (e.g. BSA). Typically, the antibody binds with an affinity corresponding to a $K_D$ of about $10^{-7}$ M or less, such as about $10^{-8}$ M or less, such as about $10^{-9}$ M or less, for example about $10^{-10}$ M or less, when measured as apparent affinities based on $IC_{50}$ values.

In one embodiment the anti-PDGF-CC antibody specifically binds PDGF-CC and optionally also PDGF-C, but not any other PDGF.

In one embodiment said anti-PDGF-CC antibody is a naturally occurring antibody or a functional homologue thereof. A naturally occurring antibody is a heterotetrameric glycoproteins capable of recognizing and binding an antigen comprising two identical heavy (H) chains and two identical light (L) chains inter-connected by disulfide bonds. Each heavy chain comprises or preferably consists of a heavy chain variable region (abbreviated herein as $V_H$) and a heavy chain constant region (abbreviated herein as $C_H$). Each light chain comprises or preferably consists a light chain variable region (abbreviated herein as $V_L$) and a light chain constant region (abbreviated herein as $C_L$). The $V_H$ and $V_L$ regions can be further subdivided into regions of hypervariability, termed complementarity determining regions (CDRs), interspersed with regions that are more conserved, termed framework regions (FRs). Each $V_H$ and $V_L$ comprises and preferably consists of three CDRs and four FRs, arranged from amino-terminus to carboxy-terminus in the following order: FR1, CDR1, FR2, CDR2, FR3, CDR3, FR4.

Naturally occurring antibodies according to the invention may consist of one heterotetramer or they may comprise several identical heterotetramers. Thus, the naturally occurring antibody according to the invention may for example be selected from the group consisting of IgG, IgM, IgA, IgD and IgE. The subunit structures and three-dimensional configurations of these different classes of immunoglobulins are well known. In a preferred embodiment of the invention the antibody is IgG, e.g. IgG-1, IgG-2, IgG-3 and IgG-4.

Naturally occurring antibodies according to the invention may be antibodies of a particular species, for example the antibody may be a murine, a rat, a rabbit, a goat, a sheep, a chicken, a donkey, a camelid or a human antibody. The antibody according to the invention may however also be a hybrid between antibodies from several species, for example the antibody may be a chimeric antibody, such as a humanized antibody.

It is not always desirable to use non-human antibodies for human therapy, accordingly the anti-PDGF-CC antibody according to the invention may be a human antibody or a humanized antibody, e.g. a naturally occurring human antibody.

The anti-PDGF-CC antibody according to the invention may be a human immunoglobulin or a humanized immunoglobulin, e.g. a naturally occurring human immunoglobulin.

A human antibody as used herein is an antibody, which is obtained from a system using human immunoglobulin sequences. Human antibodies may for example be antibodies isolated from an animal (e.g., a mouse) that is transgenic or transchromosomal for human immunoglobulin genes or a hybridoma prepared therefrom. Human antibodies may also be isolated from a host cell transformed to express the antibody, e.g., from a transfectoma. Human antibodies may also be isolated from a recombinant, combinatorial human antibody library.

Human antibodies have variable and constant regions derived from human germline immunoglobulin sequences. In certain embodiments, however, such recombinant human antibodies can be subjected to in vitro mutagenesis or in vivo somatic mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A human antibody is preferably at least 90%, more preferably at least 95%, even more preferably at least 96%, 97%, 98%, or 99% identical in amino acid sequence to the amino acid sequence encoded by a wild type human immunoglobulin gene.

Said transgenic of transchromosomal animal may contain a human immunoglobulin gene miniloci that encodes unrearranged human heavy (μ and/or γ) and K light chain immunoglobulin sequences. Furthermore, the animal may contain one or more mutations that inactivate the endogenous heavy and light chain loci. Examples of such animals are described in Lonberg, N. et al. (1994) Nature 368 (6474):856-859 and WO 02/43478.

The anti-PDGF-CC antibody according to the invention may be a chimeric antibody, i.e. an antibody comprising regions derived from different species. The chimeric antibody may for example comprise variable regions from one species of animal and constant regions from another species of animal. For example, a chimeric antibody can be an antibody having variable regions which derive from a mouse monoclonal antibody and constant regions which are human. Such antibodies may also be referred to as humanized antibodies.

Thus, the anti-PDGF-CC antibody according to the invention may also be a humanized antibody, which is encoded partly by sequences obtained from human germline immunoglobulin sequences and partly from other sequences. Said other sequences are preferably germline immunoglobulines from other species, more preferably from other mammalian species. In particular a humanized antibody may be an antibody in which the antigen binding site is derived from an immunoglobulin from a non-human species, preferably from a non-human mammal, e.g. from a mouse or a rat, whereas some or all of the remaining immunoglobulin-derived parts of the molecule are derived from a human immunoglobulin. The antigen binding site from said non-human species may for example consist of a complete $V_L$ or $V_H$ or both or one or more CDRs grafted onto appropriate human framework regions in $V_L$ or $V_H$ or both. Thus, in a humanized antibody, the CDRs can be from a mouse or rat monoclonal antibody and the other regions of the antibody are of human origin.

The anti-PDGF-CC antibody according to the invention may be a monoclonal antibody, such as a naturally occurring monoclonal antibody or it may be polyclonal antibodies, such as naturally occurring polyclonal antibodies.

The anti-PDGF-CC antibody may be any protein or polypeptide containing an antigen binding site, such as a single polypeptide, a protein or a glycoprotein. Preferably, the antigen binding site comprises at least one CDR, or more preferably a variable region.

Thus the antigen binding site may comprise a $V_H$ and/or $V_L$. In an antibody, the $V_H$ and $V_L$ together may contain the antigen binding site, however, either one of the $V_H$ or the $V_L$ may comprise an antigen binding site.

The anti-PDGF-CC antibody may for example be an antigen binding fragment of antibody, preferably an antigen binding fragment of a naturally occurring antibody, a heterospecific antibody, a single chain antibody or a recombinant antibody.

An anti-PDGF-CC antibody according to the invention may comprise one or more antigen binding sites. Naturally occurring heterotetrameric antibodies comprises two antigen binding sites.

As mentioned herein above, the anti-PDGF-CC antibodies to be used with the invention are capable of recognizing and binding PDGF-CC. Thus, in general the anti-PDGF-CC antibodies specifically bind one or more epitopes on PDGF- CC. In embodiments of the invention wherein the antibody is a monoclonal antibody, then the antibody generally binds one epitope on PDGF-CC.

Said epitope(s) may be positioned in any useful part of PDGF-CC. However, in a preferred embodiment of the invention, the antibodies are inhibitory antibodies, i.e. the antibodies are capable of inhibiting PDGF-CC activity. In particular it may be preferred that the antibodies are capable of inhibiting binding of PDGF-CC to the PDGFRα homodimer and/or to the PDGFRα/β heterodimer. The anti-PDGF-CC antibodies may also be capable of inhibiting activation of the PDGFRα homodimer and/or of the PDGFRα/β heterodimer. Activation of PDGFRα homodimer and/or the PDGFRα/β heterodimer may for example be determined by determining the kinase activity of PDGFRα homodimer and/or to the PDGFRα/β heterodimer.

In one embodiment it is preferred that the anti-PDGF-CC antibody is capable of inhibiting proteolytic processing of PDGF-CC.

In one embodiment of the invention said anti-PDGF-CC antibody may be any of the antibodies described in U.S. patent application No. 62/357,536. Thus, the anti-PDGF-CC may include the entire antibody, a fragment or substantially homologous fragment of the monoclonal antibodies (mAbs) A3B6, 11F5, 19C7 and 12F5, of the chimeric antibody chA3B6 or of the humanized antibody huA3B6 described in U.S. application 62/357,536. Fragments may include one or a portion of the variable light and heavy chain sequences or CDR regions of A3B6, chA3B6, huA3B6, 1011F5, 12F5 and 19C7 as described in U.S. application 62/357,536. The anti-PDGF-CC antibody may in a preferred embodiment be a humanized antibody, in particular the antibody huA3B6 described in U.S. application 62/357,536.

In one embodiment, the anti-PDGF-CC antibody may bind one or more epitopes within the PDGF-CC core active domain, which is provided at residues 230-345 of the full-length sequence, which is provided as SEQ ID NO.: 1.

Thus, in one embodiment of the invention it is preferred that the anti-PDGF-CC antibody binds an epitope positioned in the region of PDGF-CC, which includes the cleavage site. In human PDGF-C the cleavage site is positioned at amino acids 231 to 234 of SEQ ID NO:1. Accordingly, it is preferred that the anti-PDGF-CC antibody is capable of binding an epitope comprising at least part of an amino acid selected from the group consisting of amino acids 231, 232, 233 and 234 of SEQ ID NO:1. In particular, the anti-PDGF-CC antibody may be capable of binding an epitope comprising at least one of amino acids 231, 232, 233 and 234 of SEQ ID NO:1. In other embodiments the anti-PDGF-CC antibody may be capable of binding an epitope immediately adjacent to the cleavage site thereby inhibiting proteolytic processing of PDGF-C. Thus, in one embodiment the anti-PDGF-CC antibody is capable of binding an epitope positioned within amino acids 230 to 250 of SEQ ID NO:1.

In one embodiment of the invention the anti-PDGF-CC antibody binds a PDGF-C epitope described in WO2005/087812. For example the anti-PDGF-CC antibody may bind an epitope comprised of amino acids 231 to 274 of SEQ ID NO:1.

In one embodiment of the invention the anti-PDGF-CC antibody binds a PDGF-C epitope described in WO2007/124308. For example the anti-PDGF-CC antibody may bind an epitope positioned within, comprising or consisting of amino acids 228 to 238 of SEQ ID NO:1.

In one embodiment of the invention the anti-PDGF-CC antibody binds a PDGF-C epitope described in WO2013/160359. For example the anti-PDGF-CC antibody may bind an epitope positioned within, comprising or consisting of amino acids 308 to 322 of SEQ ID NO:1.

In one embodiment of the invention the anti-PDGF-CC antibody may bind an epitope positioned within, comprising or consisting of amino acids 242 to 254 of SEQ ID NO:1.

In one embodiment of the invention the anti-PDGF-CC antibody may bind an epitope positioned within, comprising or consisting of amino acids 288 to 308 of SEQ ID NO:1.

In one embodiment of the invention the anti-PDGF-CC antibody may bind an epitope positioned within, comprising or consisting of amino acids 325 to 345 of SEQ ID NO:1.

In one embodiment of the invention the anti-PDGF-CC antibody may bind an epitope positioned within, comprising or consisting of amino acids 256 to 274 of SEQ ID NO:1.

In one embodiment of the invention the anti-PDGF-CC antibody may bind an epitope positioned within, comprising or consisting of amino acids 256 to 264 of SEQ ID NO:1.

In one embodiment of the invention the anti-PDGF-CC antibody may bind an epitope positioned within, comprising or consisting of amino acids 256 to 260 of SEQ ID NO:1.

PDGF-CC

Platelet-derived growth factors (PDGFs) are growth factors important for normal tissue growth and maintenance. PDGF-C is secreted from cells as a latent dimer, PDGF-CC. PDGF-CC signals through the PDGFR-α, in particular through the PDGFRα homodimer and/or to the PDGFRα/s heterodimer. Tissue plasminogen activator (tPA) is a secreted serine protease with highly restricted substrate specificity, and tPA cleaves and activates latent dimeric PDGF-CC.

In preferred embodiments of the invention PDGF-CC is human PDGF-CC. The sequence of human PDGF-C is provided herein as SEQ ID NO:1 and human PDGF-CC is a dimer of two polypeptides of SEQ ID NO:1.

PDGF-CC may however also be a functional homologue of human PDGF-C, for example a dimer of polypeptides, which each share at least 70%, such as at least 80%, for example at least 85%, such as at least 90%, for example at least 95% sequence identity with SEQ ID NO:1.

PDGF-CC may thus also be PDGF-CC of other mammals.

Inhibitors of PDGF-R

The present disclosure relates to a kit-of-part comprising an inhibitor of platelet-derived growth factor receptor (PDGF-R) as well as methods of treatment employing an inhibitor of PDGF-R. The inventors have found that inhibition of the PDGF receptor results in sensitization of ER-negative breast tumor to the action of endocrine therapy.

PDGF-Rs are cell surface tyrosine kinase receptors for members of the platelet-derived growth factor (PDGF) family. There are two forms of the PDGF-R, alpha (UniProt accession number P16234; SEQ ID NO:8) and beta (UniProt accession number P09619; SEQ ID NO:9) each encoded by a different gene. Depending on which growth factor is bound, PDGF-R may homo- or heterodimerize. The extracellular region of the receptor consists of five immunoglobulin-like domains while the intracellular part is a tyrosine kinase domain. The PDGFs bind the tyrosine kinase domain of PDGF-R alpha or beta and so cause the receptor to dimerize. The different PDGFs interact with different receptor dimers. Dimerization is a prerequisite for the activation of the kinase, which will phosphorylate some critical residues of the receptor itself as well as of the receptor substrates. The phosphorylated residue of the receptor is located in proximity to usually three specific binding sites for signal transduction molecules, in the extracellular region. The signal transduction molecules may be equipped with different enzymatic activities, or may act as adaptor molecules, which in some but not all cases are found in complexes with subunits that carry a catalytic activity. Upon interaction with the activated receptor, the catalytic activities become up-regulated. The main downstream mediators of the PDGF-R signaling appear to be Ras/mitogen-activated protein kinase (MAPK), PI-3 kinase and phospholipase-γ (PLCγ) pathways. In addition, reactive oxygen species (ROS)-dependent STAT3 activation has been established to be a key downstream mediator of PDGF-R signaling in vascular smooth muscle cells.

Expression of both receptors and each of the four PDGFs is under independent control, which gives the PDGF/PDGF-R system a high flexibility. Different cell types vary greatly in the ratio of PDGF isoforms and PDGF-Rs expressed.

The inventors have found that by using inhibitors of PDGF-R, a result similar to that obtained by using anti-PDGF-CC antibodies is obtained, however the mechanism behind the treatment is different.

The inhibitor of PDGF-R, or a variant thereof, according to the present disclosure may be any compound capable of interacting with the PDGF-R and blocking its tyrosine kinase activity. For example, the inhibitor of PDGF-R may bind and specifically occupy the tyrosine kinase site of PDGF-R.

Throughout the present disclosure, the term "PDGF-R" refers to both PDGF-R alpha (PDGF-Rα) and PDGF-R beta (PDGF-Rβ) as well as variants thereof, for example the naturally occurring isoforms of PDGF-Rα and PDGF-Rβ.

In some embodiments, the inhibitor of PDGF-R is capable of inhibiting the tyrosine kinase activity of PDGF-Rα and PDGF-Rβ.

In some embodiments, the inhibitor of PDGF-R is capable of inhibiting the tyrosine kinase activity of PDGF-Rα.

In some embodiments, the inhibitor of PDGF-R is capable of inhibiting the tyrosine kinase activity of PDGF-Rβ.

In some embodiments, the inhibitor of PDGF-R is a tyrosine-kinase inhibitor.

Several inhibitors of PDGF-R are known, for example imatinib, nilotinib, axitinib sunitinib, dasitinib, sorafenib, SU6668, pazopanib, lenvatinib, cabozantinib and nintedanib.

Preferably, in some embodiments of the present disclosure the inhibitor of PDGF-R is imatinib.

In other embodiments of the present disclosure, the inhibitor of PDGF-R is an antibody against PDGF-R. Some antibodies are in fact capable of interacting with PDGF-Rs and block or neutralize their activity; in particular they can block or neutralize signaling departing from the PDGF-Rs.

The anti-PDGF-R antibodies may bind to any PDGF-R. However, in general it is preferred that the anti-PDGF-R antibodies to be used are capable of binding PDGF-R of the individual to be treated. Accordingly, in embodiments of the invention where the individual is a human being, then it is preferred that the anti-PDGF-R antibodies are capable of binding human PDGF-R, for example human PDGF-Rα and/or human PDGF-Rβ.

The anti-PDGF-R antibody according to the present invention may be any polypeptide or protein capable of recognizing and binding PDGF-R. By the term "specifically binding" is meant binding with at least 10 times higher affinity to PDGF-R, PDGF-Rα and/or PDGF-Rβ, than to a non-specific antigen (e.g. BSA). Typically, the antibody binds with an affinity corresponding to a $K_D$ of about $10^{-7}$ M or less, such as about $10^{-8}$ M or less, such as about $10^{-9}$ M or less, for example about $10^{-10}$ M or less, when measured as apparent affinities based on $IC_{50}$ values. Naturally occurring antibodies according to the invention may consist of one heterotetramer or they may comprise several identical heterotetramers. Thus, the naturally occurring antibody according to the invention may for example be selected from the group consisting of IgG, IgM, IgA, IgD and IgE. The subunit structures and three-dimensional configurations of these different classes of immunoglobulins are well known.

In one embodiment said anti-PDGF-R antibody is a naturally occurring antibody or a functional homologue thereof, as defined in the section "Anti-PDGF-CC antibody".

As described in the above section "Anti-PDGF-CC antibody", naturally occurring antibodies according to the invention may be antibodies of a particular species.

However the antibodies may also be a hybrid between antibodies from several species, for example the antibody may be a chimeric antibody, such as a humanized antibody.

It is not always desirable to use non-human antibodies for human therapy, accordingly the anti-PDGF-R antibody according to the invention may be a human antibody or a humanized antibody, e.g. a naturally occurring human antibody, as described in the above section "Anti-PDGF-CC antibody".

The anti-PDGF-R antibody according to the invention may be a human immunoglobulin or a humanized immunoglobulin, e.g. a naturally occurring human immunoglobulin.

The anti-PDGF-R antibody according to the invention may be a monoclonal antibody, such as a naturally occurring monoclonal antibody or it may be polyclonal antibodies, such as naturally occurring polyclonal antibodies, as described in the above section "Anti-PDGF-CC antibody".

The anti-PDGF-R antibody may be any protein or polypeptide containing an antigen binding site, such as a single polypeptide, a protein or a glycoprotein. Preferably, the antigen binding site comprises at least one CDR, or more preferably a variable region.

As mentioned herein above, the anti-PDGF-R antibodies to be used with the invention are capable of recognizing and binding PDGF-Rα and/or PDGF-Rβ. Thus, in general the anti-PDGF-R antibodies specifically bind one or more epitopes on PDGF-Rα and/or PDGF-Rβ. In embodiments of the invention wherein the antibody is a monoclonal antibody, then the antibody generally binds one epitope on PDGF-Rα and/or PDGF-Rβ.

Polyclonal antibodies that bind one or more epitope on PDGF-Rα and/or PDGF-Rβ can also be used.

In some embodiments, the inhibitor of PDGF-R is an antibody that targets both PDGF-Rα and PDGF-Rβ. The antibody may also be specific for PDGF-Rα. Alternatively, the antibody may be specific for PDGF-Rβ.

Anti-Estrogen

The present invention relates to a kit-of-part comprising an anti-estrogen as well as to methods of treatment employing an anti-estrogen. Said anti-estrogen may be any compound capable of reducing the production or utilization of estrogen.

In general anti-estrogens can be divided into two different subclasses, namely compounds capable of reducing or inhibiting production of estrogens and compounds capable of reducing and/or inhibiting the activity of estrogen. The latter group includes compounds capable of preventing or reducing signaling mediated by estrogen receptors.

Thus, in one embodiment of the invention the anti-estrogen is an aromatase inhibitor. Aromatase inhibitors work by blocking or reducing the synthesis of estrogen in a mammal and thereby lowering the level of estrogen. Examples of aromatase inhibitors include but are not limited to exemestane, anastrozole, letrozole, aminoglutethimide, testolactone, vorozole, formestane and fadrozole.

In another embodiment the anti-estrogen is an estrogen antagonist. Examples of estrogen antagonists include but are not limited to tamoxifen, raloxifene, 4-hydroxytramoxifen, trioxifene, keoxifene, afimoxifene, LY117018, fulvestrant, arzoxifene, lasofozone and toremifene.

The estrogen antagonist may be a compound which both is an antagonist, but also a partial agonist of estrogen. An example of such an anti-estrogen is tamoxifen.

The estrogen antagonist may also be a full antagonist of estrogen. An example of such an anti-estrogen is fulvestrant.

A preferred anti-estrogen to be used with the present invention is tamoxifen. Tamoxifen is a triphenylalkylene derivative that binds to the estrogen receptor (ER). The therapeutic mechanisms of tamoxifen are complex, but the primary effect of tamoxifen is exerted via estrogen receptors. In addition to tamoxifen its active metabolites N-desmethyltamoxifen and endoxifen (4-hydroxy-N-desmethyl-tamoxifen) may be used as anti-estrogens with the invention.

The anti-estrogen to be used with the present invention may thus be a triphenylalkylene derivative, such as tamoxifen or structurally similar compounds including clomiphene, 4-hydroxylated, the N-dealkylated and the 4-hydroxy-N-dealkylated analogs of clomiphene, tamoxifen, pyrrolidinotamoxifen, toremifene, fixed ring tamoxifen, fispemifene, as well as all other molecules with substantially similar structures. Also both cis and trans isomer of the aforementioned may be employed.

The anti-estrogen may also be a selective estrogen receptor modulator (SERM). SERMs of the invention include, without limitation, triphenylalkylenes, which include: 2-[4-(1,2-diphenylbut-1-enyl)phenoxy]-N,N-dimethyl-ethanamine (tamoxifen) and other compounds described in U.S. Pat. No. 4,536,516, incorporated herein by reference; 4'-hydroxy-2-[4-(1,2-diphenylbut-1-enyl)phenoxy]-N,N-dimethyl-ethanamine (4'-hydroxytamoxifen) and other compounds described in U.S. Pat. No. 4,623,660, incorporated herein by reference, as well as the dealkylated variant 4'-hydroxy-2-[4-(1,2-diphenylbut-1-enyl)phenoxy]-N-monomethyl-ethanamine (N-desmethyl-4'-hydroxytamoxifen also known as endoxifen); fixed ring tamoxifen and its 4'-hydroxyl, N-desmethyl, N-desethyl, 4'-hydroxy-N-desmethyl and 4'-hydroxy-N-desethyl fonns; 1-[4'-(dimethylaminoethoxy)phenyl]-1-(3'-hydroxyphenyl)-2-phenylbut-1-ene (droloxifene) and other compounds described in U.S. Pat. No. 5,047,431 as well as their 4'-hydroxy, N-desethyl and 4'-hydroxy-N-desethyl fonns; 2-[p-[4-chloro-1,2-diphenyl-1-butenyl]phenoxy]-N,N-dimethylethylamine (toremifene) and other compounds described in U.S. Pat. Nos. 4,696,949, 5,491,173 and 4,996,225, each of which is incorporated herein by reference, as well as 4'-hydroxytoremifene, N-dcsmethyl-toremifene and N-desmethyl-4'-hydroxytoremifene; 1-(2-(4-(1-(4-iodo-phenyl)-2-phenyl-but-1-enyl)-phenoxy)-ethyl)-pyrrolidinone (idoxifene) and other compounds described in U.S. Pat. No. 4,839,155, incorporated herein by reference; as well as 4-hydroxypyrrolidinotamoxifen; 2-(2-{4-[(1Z)-4-chloro-1,2-diphenylbut-1-en-1-yl]phenoxyl ethoxy)ethan-I-ol (fispemifene) and other compounds described in U.S. Pat. No. 7,504,530, each of which is incorporated herein by reference, as well as 4'-hydroxyfispemifene; clomiphene and both its isomers; and compounds described in U.S. Pat. Nos. 4,696,949 and 5,491,173 and 6,576,645, each of which is incorporated herein by reference, as well as (E) 4'-hydroxyclomiphene, (E) N-desethyl-clomiphene and (E) N-desethyl-4'-hydroxyclomiphene.

SERMS to be used with the invention also include, without limitation, benzothiphene derivatives such as: [6-hydroxy-2-(4-hydroxyphenyl)-benzothiophen-3-yl]-[4-[2-(1-piperidinyl)ethoxy)phenyl]-methanone (raloxifene) and other compounds described in U.S. Pat. Nos. 4,418,068 and 5,393,763, both of which are incorporated herein by reference; LY353381; and LY335563 and other compounds described in VO 98/45286, WO 98/45287 and WO 98/45288; benzopyran derivatives such as: (+)-7-pivaloyloxy-3-(4'pivaloyloxyphenyl)-4-methyl-2-(4"-(2"piperidinoethoxy)phenyl)-2H-benzopyran (EM 800/SCH 57050) and other compounds described in WO 96/26201; (2S)-3-(4-hydroxyphenyl)-4-methyl-2-[4-[2-(1-piperidypethoxy] phenyl]-2H-chromen-7-ol (EM 652); naphthalene derivatives such as: Cis-6-phenyl-5-[4-(2-pyrrolidin-1-yl-ethoxy)-phenyl]-5,6,7,8-tetrahydronaphthalen-2-ol (lasofoxifene/CP 336,156) and other compounds described in U.S. Pat. No. 5,552,412; 3,4-dihydro-2-(p-methoxyphenyl)-1-naphthyl-p-[2-(1-pyrrolidinyl)ethoxy]phenyl ketone (trioxifene/ LY133314) and other compounds described in U.S. Pat. No. 4,230,862, incorporated herein by reference; and 1-(4-Substituted alkoxy)benzyl)naphthalene compounds such as those described in U.S. Pat. No. 6,509,356, incorporated herein by reference; chromans such as 3,4-trans-2,2-dimethyl-3-phenyl-4-[4-(2-(2-(pyrrolidin-1-ypethoxy)phenyl]-7-methoxychroman (levormeloxifene) and other compounds described in WO 97/25034, VO 97/25035, WO 97/25037 and WO 97/25038; and 1-(2-((4-(-methoxy-2,2, dimethyl-3-phenyl-chroman-4-yl)-phenoxy)-ethyl)-pyrrolidine (centchroman) and other compounds described in U.S. Pat. No. 3,822,287, incorporated herein by reference.

Other SERMs of the invention include, without limitation, the compounds described in U.S. Pat. Nos. 6,387,920, 6,743,815, 6,750,213, 6,869,969, 6,927,224, 7,045,540, 7,138,426, 7,151,196, and 7,157,604, each of which is incorporated herein by reference.

Further non-limiting anti-estrogens to be used with the invention include: 6a-chloro-16a-methyl-pregn-4-ene-3,20-dione (clometherone); 6-chloro-17-hydroxypregna-1,4,6-triene-3,20-dione (delmadinone); 1-[2-[4-[1-(4-methoxyphenyl)-2-nitro-2-phenylethenyl]phenoxy]ethyl]-pyrrolidine (nitromifene/CN-55,945-27); and 1-[2-[p-(3,4-Dihydro-6-methoxy-2-phenyl-1-naphthyl)phenoxy]ethyl] pyrrolidine (nafoxidene). Further non-limiting anti-estrogens to be used with the invention include indoles such as those disclosed in J. Med. Chem., 33:2635-2640 (1990), J. Med. Chem., 30:131-136 (1987), CA 02889770 2015-04-24 WO 2014/070523 PCT/US2013/066141 WO 93/10741, WO 95/17383, WO 93/23374 and U.S. Pat. Nos. 6,503,938 and 6,069,153, both of which are incorporated herein by reference.

Further non-limiting anti-estrogens to be used with the invention include 2-[3-(1-cyano-1-methyl-ethyl)-5-(1H-1,2,4-triazol-1-ylmethyl)phenyl]-2-methyl-propanenitrile (anastrozole) and other compounds described in EP 0296749; 6-Methylenandrosta-1,4-diene-3,17-dione (exemestane) and other compounds described in U.S. Pat. No. 4,808,616, incorporated herein by reference; 4-[(4-cyanophenyl)-(1,2,4-triazol-1-y1)methylThenzonitrile (letrozole) and other compounds described in U.S. Pat. No. 5,473,078, incorporated herein by reference; 1-[4'-dimethylaminoethoxy)phenyl]-1-(3'-hydroxyphenyl)-2-phenylbut-1-ene (droloxifene) and other compounds described in U.S. Pat. No. 5,047,431, incorporated herein by reference; 2a,3a-Epithio-5a-androstan-1713-01 (epitiostanol); 2a,3a-Epitio- 5a-androstane-1713-yl-I-methoxycyclopentyloxy (mepitiostane); 4-[(2Z,4Z)-4-(4-hydroxyphenyl)hexa-2,4-dien-3-yl]phenol (cycladiene) and other compounds described in U.S. Pat. Nos. 2,464,203 and 2,465,505, both of which are incorporated herein by reference; CI-680 described in Unlisted Drugs, 28(10): 169(0) (1976); CI-628 described in Unlisted Drugs, 26(7): 106(1) (1974); 13-ethyl-17a-ethyn1-1713-hydroxygona-4,9,1-trien-3-one (R2323); diphenol hydrochrysene and erythyro-MEA both described in Geynet, et al., Gynecol. Invest. 3(1):2-29 (1972); 1-[1-chloro-2,2-bis(4-methoxyphenyl)ethenyl]-4-methoxy-benzene (chlorotrianisene) described in Merck Index, 10th ed., #2149; 144-(2-Diethylaminoethoxy)phenyl]-1-phenyl-2-(p-anisyl) ethanol (ethamoxytriphetol) described in Merck Index, 10th ed., #3668; and 2-p-Chlorophenyl-14p-(2-diethylaminoethoxy)phenyl]-1-p-tolylethanol (triparanol) and other compounds described in U.S. Pat. No. 2,914,562, incorporated herein by reference. [0057] Still other antiestrogens of the invention include, without limitation: (2e)-3-(4-((1e)-1,2-diphenylbut-1-enyl)phenyl)acrylic acid (GW5638), GW7604 and other compounds described in Wilson et al., Endocrinology, 138(9):3901-3911 (1997) and WO 95/10513; 144-(2-diethylaminoethoxy)phenyl]-2-(4-methoxyphenyl)-1-phenyl-ethanol (MER-25), N,N-diethyl-244-(5-methoxy-2-phenyl-3H-inden-1-yl)phenoxylethanamine hydrochloride (U-11,555A), 1-[2-[4-(6-methoxy-2-phenyl-3,4-dihydronaphthalen-1-yl)phenoxy] ethyllpyrrolidine hydrochloride (U-11,100A), ICI-46,669, 2-[4-[(Z)-1,2-diphenylbut-1-enyl]phenoxy]-N,N-dimethylethanamine; 2-CA 02889770 2015-04-24 WO 2014/070523 PCT/US2013/066141 hydroxypropane-1,2,3-tricarboxylic acid (ICI-46,474) and other compounds described in Terenius et al., Gynec. Invest., 3:96-107 (1972); 2-Hydroxy-6-naphthalenepropionic acid (allenolic acid); [4-[(4-acetyloxyphenyl)-cyclohexylidene-methyl]phenyliacetate (cyclofenyl/ICI-48213); [6-hydroxy-2-(4-hydroxyphenyl) benzothiophen-3-yl]-[4-[2-(1-piperidypethoxy]phenylimethanone (keoxifene); 4-[(Z)-1-[4-(2-dimethylaminoethoxy)phenyl]-2-(4-propan-2-ylphenyl)but-1-enyl]phenol (DP-TAT-59/miproxifene); (1RS,2RS)-4,4'-diacetoxy-5,5'-difluoro-(1-ethyl-2-methylene)di-m-phenylenediacetate (acefluranol); 6-hydroxy-2-(p-hydroxyphenyl)-benzo(b) thien-3-yl[2-(1-pyrrolidiny1)-ethoxyphenyl]ketone (LY-117018); and [6-hydroxy-2-(4-hydroxy-phenyl)benzo(b) thien-3-yl]-[4-(2-(1-piperidiny1)-ethoxy)phenyl]methanone (LY-156758). [0058] Still other antiestrogens of the invention include, without limitation: non-steroidal estrogen receptor ligands such as those described in U.S. Pat. Nos. 5,681,835, 5,877,219, 6,207,716, 6,340,774 and 6,599,921, each of which is incorporated herein by reference; steroid derivatives such as those described in U.S. Pat. No. 4,659, 516, incorporated herein by reference; 7a-11-aminoalkylestratrienes such as those described in WO 98/07740; 11-f3-halogen-7a-substituted estratrienes such as those described in WO 99/33855; 17a-alkyl-173-oxy-estratrienes such as those described in U.S. patent application Ser. No. 10/305, 418, incorporated herein by reference; 2-phenyl-144-(2-aminoethoxy)-benzyl]-indoles such as those described in U.S. Pat. No. 7,132,417, incorporated herein by reference; 4-fluoroalkyl-2h-benzopryans such as those described in U.S. Pat. No. 6,844,336, incorporated herein by reference; (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone and other benzothiophenes described in WO 95/10513 and U.S. Pat. No. 4,133,814, incorporated herein by reference; 2-pheny1-1-[4-(2-aminoethoxy)-benzyl]-indoles such as those described in U.S. Pat. No. 5,998,402, incorporated herein by reference; 3-[4-(2-Phenyl-Indole-I-ylmethyl) Phenyl]-Acrylamides and other compounds described in U.S. Pat. No. 5,985,910, incorporated herein by reference; 2-phenyl-I-[4-(amino-1-yl-alk-1-yny1)-benzyl]-1H-indol-5-ols and other compounds described in U.S. Pat. Nos. 5,780,497 and 5,880,137, both of which are incorporated herein by reference; steroids such as those described in U.S. Pat. Nos. 6,455,517, 6,548,491, 6,747,018 and 7,041, 839, each of which is incorporated herein by reference; Di-(3'-hydroxyphenyl)-alkane compounds CA 02889770 2015-04-24 WO 2014/070523 PCT/US2013/066141 such as those described in U.S. Pat. No. 4,094,994, incorporated herein by reference; phenol derivatives such as those described in U.S. Pat. No. 4,751,240, incorporated herein by reference; 2,3-diaryl-2H-1-benzopyran analogs such as those described in Saeed et al., J. Med. Chem., 33:3210-3216 (1990) and Sharma et al., J. Med. Chem. 33:3216-3229 (1990); and benzofuran and triaryfuran analogs such as those described in Durani et al., J. Med. Chem., 32:1700-1707 (1989).

The anti-estrogen to be used with the invention may also be a pharmaceutically acceptable salt, ester, or prodrug of any of the aforementioned anti-estrogens. Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The anti-estrogens of the invention may be administered in the form of an alkali metal or earth alkali metal salt thereof, concurrently, simultaneously, or together with a pharmaceutically acceptable carrier or diluent in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

ER-Negative Breast Cancer

The anti-PDGF-CC antibody, the kit-of-parts and the methods of the invention are useful for treatment of ER-negative breast cancer.

The ER-negative breast cancer may be any breast cancer characterized by lack of expression of the estrogen receptor (ER). As used herein a breast cancer is considered an ER-negative breast cancer, when=<10% of the tumor cells of said breast cancer express estrogen receptor at levels detectable by immunohistochemistry. In some embodiments of the invention, the ER-negative breast cancer is a breast cancer, where <1% of the tumor cells of said breast cancer express estrogen receptor at levels detectable by immunohistochemistry Immunohistochemistry may preferably be a test involving staining of a sample from a breast cancer with the aid of antibodies recognizing ER, and followed by detection of ER expression in the cells of said sample, e.g. by microscopy.

In one embodiment of the invention the ER-negative breast cancer is a breast cancer wherein <1% tumor nuclei are positive for ER expression as recommended by American Society of Clinical Oncology as described by Hammond et al., 2010.

According to the present invention, ER expression may be determined by any useful means, preferably by any useful immunohistochemical method. Preferably, ER expression may be determined as described by Hammond et al., 2010.

In one embodiment of the invention the ER-negative breast cancer also is a Progesterone receptor negative (PR-negative) breast cancer. Thus, the breast cancer be to treated may in particular be an ER-negative and PR-negative breast cancer. Said PR-negative breast cancer may be a breast cancer where=<10% of the tumor cells of said breast cancer express the progesterone receptor (PR) at levels detectable by immunohistochemistry. In some embodiments of the invention, the PR-negative breast cancer is a breast cancer, where <2% of the tumor cells of said breast cancer express PR at levels detectable by immunohistochemistry. In some embodiments of the invention, the PR-negative breast cancer is a breast cancer, where <1% of the tumor cells of said breast cancer express PR at levels detectable by immunohistochemistry.

PR expression may be determined by any useful means, preferably by any useful immunohistochemical method. Preferably, PR expression may be determined as described by Hammond et al., 2010.

The ER-negative breast cancer may in some embodiments express the human epidermal growth factor receptor 2 (HER-2).

In another embodiment of the invention the ER-negative breast cancer is a triple-negative breast cancer, i.e. said cancer is ER-negative, PR-negative and human epidermal growth factor receptor (HER)-2 negative. The terms ER-negative and PR-negative are explained above. A HER-2 negative breast cancer may be a breast cancer which expresses no detectable HER-2. The test for HER-2 expression may be performed by any useful method, for example by an immunohistochemical method or by FISH. Preferably, a HER-2 negative breast cancer is HER-2 negative when determined as recommended in Wolff et al., 2013.

In one embodiment of the invention the ER-negative breast cancer is a basal-like breast cancer. In one embodiment said basal-like breast cancer may be a triple-negative breast cancer.

A basal-like breast cancer may also be an ER-negative breast cancer, which expresses one or more high-molecular weight/basal cytokeratins, for example selected from the group consisting of CK5/6, CK14 and CK17.

The basal-like breast cancer may also be an ER-negative and HER-2 negative breast cancer, which expresses CK5/& and/or epidermal growth factor receptor.

The basal-like breast cancer may also be a triple-negative breast cancer expressing CK5/6 and/or EGFR.

Furthermore, basal-type breast cancer typically does not express FoxA1. Basal-like breast cancer is associated with high grade, poor prognosis, and younger patient age.

In particular, the ER-negative breast cancer may be a breast cancer, which at the time of first diagnosis was an ER-negative breast cancer. Thus, the ER-negative breast cancer may be characterized as ER-negative from the onset, rather than as a breast cancer having lost ER expression as a result of treatment. It may be preferred that the ER-negative breast cancer is a breast cancer, wherein the primary tumor is ER-negative.

Pharmaceutical Formulation

Whilst it is possible for the anti-PDGF-CC antibodies and the anti-estrogens of the present invention to be administered as the raw compounds, it is preferred to present them in the form of a pharmaceutical formulation. The pharmaceutical formulations may be prepared by conventional techniques, e.g. as described in Remington: The Science and Practice of Pharmacy 2005, Uppincott, Williams & Wilkins.

The compounds to be used with the present invention may be formulated for parenteral administration and may be presented in any suitable form, for example in unit dose form in ampoules, pre-filled syringes, small volume infusion or in multi-dose containers, optionally with an added preservative. In particular it is foreseen that the anti-PDGF-CC antibodies are formulated for parenteral administration, however, also anti-estrogens may be formulated for parenteral administration.

For parenteral administration the formulations may take such forms as suspensions, solutions, or emulsions in oily or aqueous vehicles, for example solutions in aqueous polyethylene glycol. Alternatively, the active ingredient may be in powder form, obtained by aseptic isolation of sterile solid or by lyophilisation from solution for constitution before use with a suitable vehicle, e.g., sterile, pyrogen-free water. The formulations can for example be presented in unit-dose or multi-dose sealed containers, such as ampoules, vials, pre-filled syringes, infusion bags, or can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Examples of oily or non-aqueous carriers, diluents, solvents or vehicles include propylene glycol, polyethylene glycol, vegetable oils, and injectable organic esters, and may contain formulatory agents such as preserving, wetting, emulsifying or suspending, stabilizing and/or dispersing agents.

The formulations for injection will typically contain from about 0.5 to about 25% by weight of the active ingredient in solution for example of the anti-PDGF-CC antibody. For example, the dosage may be in the range of 1 to 100 mg anti-PDGF-CC antibody per kg body weight, such as in the range of 1 to 20 mg of anti-PDGF-CC antibody per kg body weight, for example in the range of 5 to 15 mg of anti-PDGF-CC antibody per kg body weight.

The compounds of the present invention may also be formulated in a wide variety of formulations for oral administration. This may in particular be the case for the anti-estrogens. Solid form preparations may include powders, tablets, drops, capsules, cachets, lozenges, and dispersible granules. Other forms suitable for oral administration may include liquid form preparations including emulsions, syrups, elixirs, aqueous solutions, aqueous suspensions, toothpaste, gel dentrifice, chewing gum, or solid form preparations which are intended to be converted shortly before use to liquid form preparations, such as solutions, suspensions, and emulsions.

In powders, the carrier is a finely divided solid which is a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. Suitable solvents for the preparation of an oily solution include glycerol, diluted alcohol and propylene glycol.

Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well-known suspending agents.

Any dosage of anti-estrogen used as required for efficacy, as recommended by the manufacturer, can be used. Appropriate dosages for anti-estrogens are known in the art. Thus, conventional dosages used for treatment of luminal-like breast cancers can be used for treatment of the basal-like breast cancers according to the invention. For example, anti-estrogens may be prepared form administration in a dosage range between 0.01 to 10 mg/kg of body weight per day (preferably 0.05 to 1.0 mg/kg), with 20 to 40 mg per day being preferred for a person of average body weight when orally administered, or in a dosage range between 0.003 to 3.0 mg/kg of body weight per day (preferably 0.015 to 0.3 mg/m), with 1.5 mg per day, especially 3.0 mg per day, in two equally divided doses being preferred for a person of average body weight when parentally administered.

Sequence Listing

| | |
|---|---|
| SEQ ID NO: 1 | Amino acid sequence of PDGF-CC from Homo sapiens |
| SEQ ID NO: 2 | MMTV-PyMT primer |
| SEQ ID NO: 3 | MMTV-PyMT primer |
| SEQ ID NO: 4 | PDGF-C wild-type primer |
| SEQ ID NO: 5 | PDGF-C wild-type primer |
| SEQ ID NO: 6 | PDGF-C mutant primer |
| SEQ ID NO: 7 | PDGF-C mutant primer |
| SEQ ID NO: 8 | PDGF-R alpha |
| SEQ ID NO: 9 | PDGF-R beta |

SEQ ID NO: 1
platelet-derived growth factor C precursor
Homo sapiens
MSLFGLLLLTSALAGQRQGTQAESNLSSKFQFSSNKEQNGVQDPQ

HERIITVSTNGSIHSPRFPHTYPRNTVLVWRLVAVEENVWIQLTF

DERFGLEDPEDDICKYDFVEVEEPSDGTILGRWCGSGTVPGKQIS

KGNQIRIRFVSDEYFPSEPGFCIHYNIVMPQFTEAVSPSVLPPSA

LPLDLLNNAITAFSTLEDLIRYLEPERWQLDLEDLYRPTWQLLGK

AFVFGRKSRVVDLNLLTEEVRLYSCTPRNFSVSIREELKRTDTIF

WPGCLLVKRCGGNCACCLHNCNECQCVPSKVTKKYHEVLQLRPKT

GVRGLHKSLTDVALEHHEECDCVCRGSTGG

Items

The invention may further be defined by the following items:

1. A kit-of-parts comprising an anti-PDGF-CC antibody and an anti-estrogen for the treatment of ER-negative breast cancer in an individual in need thereof.
2. A kit-of-parts comprising an inhibitor of PDGF-R and an anti-estrogen for the treatment of ER-negative breast cancer in an individual in need thereof.
3. The kit-of-parts according to item 1, wherein said anti-PDGF-CC antibody and said anti-estrogen are prepared for sequential administration.
4. The kit-of-parts according to any one of items 1 and 3 for use in the treatment of ER-negative breast cancer, wherein said treatment comprises the steps of
   a. administration of the anti-PDGF-CC antibody to an individual in need thereof;
   b. subsequent administration of the anti-estrogen.
5. The kit-of-parts according to item 2, wherein said inhibitor of PDGF-R and said anti-estrogen are prepared for sequential administration.
6. The kit-of-parts according to any one of items 2 and 5 for use in the treatment of ER-negative breast cancer, wherein said treatment comprises the steps of
   a. administration of the inhibitor of PDGF-R to an individual in need thereof;
   b. subsequent administration of the anti-estrogen.
7. The-kit-of-parts according to any one of the preceding items, wherein the individual has suffered from ER-negative breast cancer, and wherein said breast cancer in said individual has been treated by surgery, and wherein said treatment reduces the risk of relapse.
8. A method for treatment of ER-negative breast cancer in an individual in need thereof, said method comprising administering an anti-PDGF-CC antibody and an anti-estrogen to said individual either simultaneously or sequentially in any order, thereby treating the ER-negative breast cancer.
9. A method for treatment of ER-negative breast cancer in an individual in need thereof, said method comprising administering an inhibitor of PDGF-R and an anti-estrogen to said individual either simultaneously or sequentially in any order, thereby treating the ER-negative breast cancer.
10. A method for sensitizing an ER-negative breast cancer to anti-estrogen treatment, said method comprising administering an anti-PDGF-CC to an individual suffering from ER-negative breast, thereby sensitizing said ER-negative breast cancer to anti-estrogen treatment.
11. A method for sensitizing an ER-negative breast cancer to anti-estrogen treatment, said method comprising administering an inhibitor of PDGF-R to an individual suffering from ER-negative breast, thereby sensitizing said ER-negative breast cancer to anti-estrogen treatment.
12. A method of converting an ER-negative breast cancer to an ER-positive breast cancer, said method comprising administering an anti-PDGF-CC to an individual suffering from ER-negative breast, thereby converting said ER-negative breast cancer to an ER-positive breast cancer.
13. The method according to item 12, wherein the ER-positive breast cancer is a luminal like breast cancer.
14. A method of treatment of ER-negative breast cancer in an individual in need thereof, said method comprising
   a. performing the method according to any one of items 8 to 11
   b. administering an anti-estrogen to said individual thereby treating said ER-negative breast cancer.
15. A method of reducing the risk of relapse of an ER-negative breast cancer in an individual having suffered from ER-negative breast cancer, wherein said breast cancer in said individual has been treated by surgery, said method comprising a. sensitizing the ER-negative breast cancer to treatment with anti-estrogen by administering an anti-PDGF-CC antibody to an individual suffering from ER-negative breast cancer;
b. administering an anti-estrogen to said individual thereby reducing the risk of relapse of said ER-negative breast cancer.

16. A method of reducing the risk of relapse of an ER-negative breast cancer in an individual having suffered from ER-negative breast cancer, wherein said breast cancer in said individual has been treated by surgery, said method comprising
a. sensitizing the ER-negative breast cancer to treatment with anti-estrogen by administering an inhibitor of PDGF-R to an individual suffering from ER-negative breast cancer;
b. administering an anti-estrogen to said individual thereby reducing the risk of relapse of said ER-negative breast cancer.

17. The kit-of-parts or the method according to any one of items 4, 7 and 8 14 and 15, wherein the first administration of anti-PDGF-CC antibody to said individual is prior to the first administration of said anti-estrogen.

18. The kit-of-parts or the method according to any one of items 6 and 7, 9, 14 and 16, wherein the first administration of the inhibitor of PDGF-R to said individual is prior to the first administration of said anti-estrogen.

19. The kit-of-parts or the method according to any one of items 4, 7 and 8 14, 15 and 17, wherein the last administration of said anti-estrogen is later than the last of said anti-PDGF-CC antibody.

20. The kit-of-parts or the method according to any one of items 6 and 7, 9, 14, 16 and 18, wherein the last administration of said anti-estrogen is later than the last of said inhibitor of PDGF-R.

21. The kit-of-parts or the method according to any one of items 4, 7, 8, 14, 15, 17 and 19, wherein the anti-PDGF-CC antibody is administered at least twice to an individual suffering from ER-negative breast cancer.

22. The kit-of-parts or the method according to any one of items 4, 7, 8, 14, 15, 17, 19 and 21, wherein the anti-PDGF-CC antibody is administered at least twice to an individual suffering from ER-negative breast cancer wherein one or more administrations are prior to treatment by surgery, and one or more additional administrations are administered post treatment by surgery.

23. The kit-of-parts or the method according to any one of items 6, 7, 9, 14, 16, 18 and 20, wherein the inhibitor of PDGF-R is administered at least twice to an individual suffering from ER-negative breast cancer.

24. The kit-of-parts or the method according to any one of items 6, 7, 9, 14, 16, 18, 20 and 23, wherein the inhibitor of PDGF-R is administered at least twice to an individual suffering from ER-negative breast cancer wherein one or more administrations are prior to treatment by surgery, and one or more additional administrations are administered post treatment by surgery.

25. The kit-of-parts or the method according to any one of items 4, 7, 8, 14, 15, 17, 19, 21 and 22, wherein the anti-PDGF-CC antibody is administered in the range of 1 to 5 times, whereas the anti-estrogen is administered continuously for in the range of 1 to 10 years, such as in the range of 4 to 6 years, such as for 5 years.

26. The kit-of-parts or the method according to any one of items 6, 7, 9, 14, 16, 18, 20, 23 and 24, wherein the inhibitor of PDGF-R is administered in the range of 1 to 5 times, whereas the anti-estrogen is administered continuously for in the range of 1 to 10 years, such as in the range of 4 to 6 years, such as for 5 years.

27. The kit-of-parts or the method according to any one of items 1, 3, 4, 7, 8, 10, 12 to 15, 17, 19, 21, 22 and 25, wherein the anti-PDGF-CC antibody is a monoclonal antibody specifically binding PDGF-CC.

28. The kit-of-parts or the method according to any one of items 1, 3, 4, 7, 8, 10, 12 to 15, 17, 19, 21, 22, 25 and 27, wherein the anti-PDGF-CC antibody is a human monoclonal antibody specifically binding PDGF-CC.

29. The kit-of-parts or the method according to any one of items 1, 3, 4, 7, 8, 10, 12 to 15, 17, 19, 21, 22, 25, 27 and 28 wherein the anti-PDGF-CC antibody is a humanized antibody.

30. The kit-of-parts or the method according to any one of items 1, 3, 4, 7, 8, 10, 12 to 15, 17, 19, 21, 22, 25, 27 to 29, wherein the anti-PDGF-CC antibody is a neutralizing PDGF-CC antibody.

31. The kit-of-parts or the method according to any one of items 1, 3, 4, 7, 8, 10, 12 to 15, 17, 19, 21, 22, 25, 27 to 30, wherein the anti-PDGF-CC antibody is capable of inhibiting proteolytic cleavage of PDGF-CC upon binding to PDGF-CC.

32. The kit-of-parts or the method according to any one of items 1, 3, 4, 7, 8, 10, 12 to 15, 17, 19, 21, 22, 25, 27 to 31, wherein the anti-PDGF-CC antibody is capable of binding human PDGF-CC.

33. The kit-of-parts or the method according to any one of items 1, 3, 4, 7, 8, 10, 12 to 15, 17, 19, 21, 22, 25, 27 to 32, wherein the anti-PDGF-CC antibody is capable of inhibiting PDGF-CC activity.

34. The kit-of-parts or the method according to any one of items 1, 3, 4, 7, 8, 10, 12 to 15, 17, 19, 21, 22, 25, 27 to 33, wherein the anti-PDGF-CC antibody is capable of inhibiting binding of PDGF-CC to the PDGFRα homodimer and/or to the PDGFRα/s heterodimer.

35. The kit-of-parts or the method according to any one of items 1, 3, 4, 7, 8, 10, 12 to 15, 17, 19, 21, 22, 25, 27 to 34, wherein the anti-PDGF-CC antibody is capable of inhibiting activation of the PDGFRα homodimer and/or of the PDGFRα/s heterodimer.

36. The kit-of-parts or the method according to any one of items 1, 3, 4, 7, 8, 10, 12 to 15, 17, 19, 21, 22, 25, 27 to 35, wherein the anti-PDGF-CC antibody is capable of inhibiting proteolytic processing of PDGF-CC.

37. The kit-of-parts or the method according to any one of items 1, 3, 4, 7, 8, 10, 12 to 15, 17, 19, 21, 22, 25, 27 to 36, wherein the anti-PDGF-CC antibody is capable of binding an epitope positioned in, comprising or consisting of:
a. aa 230 to 250 of SEQ ID NO:1;
b. aa 228 to 238 of SEQ ID NO:1;
c. aa 308 to 322 of SEQ ID NO:1;
d. aa 242 to 254 of SEQ ID NO:1;
e. aa 288 to 308 of SEQ ID NO:1;
f. aa 325 to 345 of SEQ ID NO:1;
g. aa 256 to 274 of SEQ ID NO:1;
h. aa 256 to 264 of SEQ ID NO:1; and/or
i. aa 256 to 260 of SEQ ID NO:1

38. The kit-of-parts or the method according to any one of items 1, 3, 4, 7, 8, 10, 12 to 15, 17, 19, 21, 22, 25, 27 to 37, wherein the anti-PDGF-CC antibody is capable of binding a epitope positioned within amino acids 230 to 250 of SEQ ID NO:1.

39. The kit-of-parts or the method according to any one of items 2, 5 to 7, 9, 11, 14, 16, 18, 20, 23, 24, 26, wherein the inhibitor of PDGF-R is a tyrosine-kinase inhibitor.

40. The kit-of-parts or the method according to item 39, wherein the inhibitor of PDGF-R is capable of blocking the tyrosine kinase activity of PDGF-R.

41. The kit-of-parts or the method according to any one of items 39 and 40, wherein the inhibitor of PDGF-R is imatinib.

42. The kit-of-parts or the method according to any one of items 2, 5 to 7, 9, 11, 14, 16, 18, 20, 23, 24, 26, wherein the inhibitor of PDGF-R is an antibody capable of binding PDGF-Rα and/or PDGF-Rβ.

43. The kit-of-parts or the method according to any one of items 2, 5 to 7, 9, 11, 14, 16, 18, 20, 23, 24, 26, 42, wherein the inhibitor of PDGF-R is an antibody capable of inhibiting PDGF-Rα and/or PDGF-Rβ.

44. The kit-of-parts or the method according to any one of items 2, 5 to 7, 9, 11, 14, 16, 18, 20, 23, 24, 26, 42 and 43, wherein the inhibitor of PDGF-R is a neutralizing PDGF-Rα and/or PDGF-Rβ antibody.

45. The kit-of-parts or the method according to any one of the preceding items, wherein the anti-estrogen is an estrogen antagonist.

46. The kit-of-parts or the method according to item 45, wherein the estrogen antagonist is selected from the group consisting of tamoxifen, raloxifene, 4-hydroxytramoxifen, trioxifene, keoxifene, afimoxifene, LY117018, fulvestrant and toremifene 47. The kit-of-parts or the method according to any one of items 1 to 46, wherein the anti-estrogen is compound inhibiting production of estrogen.

48. The kit-of-parts or the method according to any one of items 1 to 44, wherein the anti-estrogen is an aromatase inhibitor.

49. The kit-of-parts or the method according to item 48, wherein the anti-estrogen is selected from the group consisting of exemestane, formestane, aminoglutethimide, vorozole, fadrozole, anastrozole and letrozole.

50. The kit-of-parts or the method according to any one of the preceding items, wherein the individual is a human being.

51. The kit-of-parts or the method according to any one of the preceding items, wherein the individual is a human being, wherein the primary breast cancer tumor has been removed by surgery.

52. The kit-of-parts or the method according to any one of the preceding items, wherein the ER-negative breast cancer is a triple negative breast cancer.

53. The kit-of-parts or the method according to any one of the preceding items, wherein the ER-negative breast cancer is a basal-like breast cancer.

54. The kit-of-parts or the method according to any one of the preceding items, wherein the ER-negative breast cancer is a breast cancer wherein the primary tumor was ER-negative.

EXAMPLES

The invention is further illustrated by the following examples, which should not be construed as being limiting for the invention.

Example 1. Anti-PDGF-CC Antibody Sensitizes Tumor to Estrogen Therapy

Patent Cohort and the Definition of Breast Tumor Subtypes

Tissues from 890 patients with primary invasive breast cancer, diagnosed at the Institute of Surgical Pathology, USZ, between 1965 and 2004 (median July 1999), were analyzed. All patients enrolled voluntarily under Institutional Review Board-approved protocols and sample donors gave written informed consent. The ethics committee SPUK surgical-anesthetic-pathology at university hospital of Zrich, Switzerland, approved this study with reference number-StV 12-2005. For all these patients follow up data from the cantonal cancer registry were available; patients without follow up information were not considered (Theurillat et al, Int J Cancer, 2007). Additionally, 69 normal tissues and 152 in situ lesions (DCIS, LN) were analyzed. Molecular cancer subtypes were defined from detected ER, HER2 and CK5/6 by IHC. Luminal type: ER-positive cases, that were HER2-negative; HER2-type: Her2-positive cases; Basal like: CK56-positive, ER-negative and HER2-negative. Cases negative for all markers were designated NIL-type.

Tissue Microarray Construction

Formalin fixed paraffin embedded material of a representative variety of normal and malignant human tissues and tumor cell lines were compiled and assembled on a single block, as described (Kristiansen et al, Br J Cancer 2008).

Immunohistochemistry on Human Tumor Tissue Array

To assess PDGF-CC expression in various tumor types, we used a rabbit polyclonal antibody against PDGF-CC, 615, on a commercially available tumor tissue array (Chemicon) according to the instruction of the manufacturer. For the breast tumor cohort and to confirm the results gained from the polyclonal antibody 615, the mab anti-PDGF-CC antibody, A3B6 (2 µg/ml) was used on an automated Ventana platform (protocol CC1m for pre-treatment, UView HRP detection system). The epitope of the A3B6 antibody is amino acids 256 to 260 of SEQ ID NO:1 within the sequence of amino acids 256 to 274 of SEQ ID NO:1. Specific immuno-reactivity was fully blocked by an excess of active PDGF-CC. The basal cell marker cytokeratin CK56 (clone cocktail D5/16B4, 1:25, Dako, Denmark), HER2 (clone 10A7, 1:50, Novocastra, UK), EGFR (clone 3C6, prediluted, Ventana, Tucson, USA) and Ki-67 (clone Mib-1, 1:20, Dako, Denmark) were processed in parallel.

Mouse Tissue Preparation, Histology and Immunostaining

Upon completion of the treatment, mice were anesthetized with 2.5% Avertin (12.5 mg/kg body weight; Sigma-Aldrich) and 300 µL of blood were collected by heart puncture and immediately mixed with RNAlater solution (Life Technologies) and stored at −20° C. Mice were heart-perfused with PBS followed by 4% paraformaldehyde (for transplanted FVB/N mice only).

For paraffin embedding, organs were post-fixed in 4% paraformaldehyde for 2 h before proceeding to embedding. Paraffin-embedded sections were deparaffinized and re-hydrated followed by antigen retrieval in high pH buffer (pH 6; DAKO) in a pressure cooker (ERα) or in 95° C. water-bath for 20 minutes (PR, STC1, IGFBP3 and HGF). Peroxidase activity was quenched with 3% $H_2O_2$ in methanol for 10 minutes at room temperature, followed by washes with 0.1% BSA in PBS.

ERα staining required subsequent steps in M.O.M. blocking (Mouse on Mouse basic kit, Vectoriabs), CAS-block (Life Technologies) and M.O.M. diluent. The primary antibody against estrogen receptor ERα (1:200, clone 1D5; DAKO) was incubated in M.O.M. diluent.

CAS-block was used for the blocking and incubation of primary antibodies against STC1 (1:200; SC-30183, Santa Cruz), IGFBP3 (1:200; SC-9028, Santa Cruz) and HGF (1:200; ab83760, Abcam). Primary incubation was performed overnight at 4° C. in a humidified chamber.

After washing, appropriate secondary biotinlylated antibodies and the ABC peroxidase system were used (ABC Elite standard kit, Vector Laboratories) with DAB as the colorimetric substrate (Vector Laboratories).

For cryopreservation, primary tumor, lungs, liver and brain were kept in 30% sucrose at 4° C. overnight, followed by embedding in Optimal Cutting Temperature (OCT) medium (HistoLab). Frozen sections were fixed in ice-cold acetone, followed by blocking using Serum Free Protein Block (DAKO) for >90 minutes at room temperature. Primary antibodies directed against PDGFRα (PE-conjugated, 1:200; 12-1401, eBioscience) and PDGFRs (1:200; 3169S, Cell Signaling) were incubated overnight at 4° C. in a humidified chamber. Appropriate Alexa488-flourochrome-conjugated secondary antibody (Life Technologies) was used and sections were finally mounted using 4',6-diamidino-2-phenylindole (DAPI)-containing mounting media (Vector Laboratories).

For RNA isolation and preparation, primary tumor, liver, lungs and brain were snap-frozen in liquid $N_2$ and stored at −80° C.

Mice

All animal experiments were approved by the Ethical Committee for Animal Experiments (Stockholm Norra djurförsöketiska nämnd, application N96/11, and Lund, application M142/13). FVB/N-Tg(MMTV-PyVT)$^{634zMul/J}$ transgenic mice have been described previously (Guy et al Molecular and Cellular Biology 1992) and were purchased from The Jackson Laboratory. The presence of the MMTV-PyMT transgene and the generation of heterozygous and homozygous knock-out PDGF-C offspring were verified by genotyping. DNA was prepared from either ear or tail biopsies according to a common tissue lysis, nucleic acid extraction and purification protocol. PCR products were run on a 1.5% agarose gel. MMTV-PyMT primer pair (5' to 3'):

```
                                            [SEQ ID NO: 2]
        GGAAGCAAGTACTTC ACAAGGG
```
and
```
                                            [SEQ ID NO: 3]
        GGAAAGTCACTAGGAGCAGGG.
```

PDGF-C wild-type pair:

```
                                            [SEQ ID NO: 4]
        AGCTGACAT TTGATGAGAGAT
```
and
```
                                            [SEQ ID NO: 5]
        AGTAGGTGAAATAAGAGGTGAACA.
```

PDGF-C mutant pair: CTC

```
                                            [SEQ ID NO: 6]
        ATGTTCTCGTGACTCTGA
and
                                            [SEQ ID NO: 7]
        TAGCTAGTCGATACCGTCGA.
```

Tumor size of the ten different glands were measured at 12 weeks of age using a caliper. Tumor volume was calculated as length×width2×π/6. Mice of different ages where anesthetized with Avertin (Sigma Aldrich, St Louis, Mo.) and then euthanized by heart perfusion with Hank's balanced salt solution (HBSS) followed by 4% Paraformaldehyde (PFA). The left cervical and thoracic mammary glands where excised and subjected to overnight fixation in 4% PFA before embedding in paraffin. For frozen sectioning the tumor tissue was subjected to 30% sucrose before embedding in OCT.

Tumor Piece Transplantation into Mammary Fat Pad 3 weeks old FVB/N (common background strain for both MMTV-PyMT and PDGF-C mice) female mice were anesthetized and maintained under Isolfluorane during the surgical procedure. A 4 mm incision under the nipple of the right abdominal mammary gland created a pocket where a 2×2 mm tumor piece (kept on ice, either from MMTV-PyMT or MMTV-PyMT; PDGF-C tumors) was inserted. Suturing was performed with 6-O Ethilon polyamide filament (Ethicon). Pain-killer and anti-inflammatory Rimadyl (5 mg/kg body weight; Orion Pharma Animal Health) was injected i.p. at the end of the surgical procedure and for the following two days. For the therapeutic trial, Tamoxifen (2 mg/mL) was diluted in corn oil (vehicle) and administered via oral gavage daily.

Mouse mammary cell lines MMTV . . . MMTV/PDGF-C−/− . . . (established in our laboratory) were orthotopically injected into the 4$^{th}$ inguinal mammary gland on FVB/N mice. Furthermore, small tumor pieces (2 mm$^3$) of MMTV-PyMT and MMTV-PDGF-CC−/− tumors were directly orthotopically transplanted under anesthesia. The mice were subjected to Rimadyl immediately after the surgery and the following two days for analgetics. The tumors were measured twice a week and mice were euthanized as described above.

Xenograft Establishment

2×10$^6$ Human MDA-MB-231 cells were inoculated subcutaneously in immunodeficient mice. Tumor growth was monitored and measured once a week with a caliper in live sedated animals. Anti-PDGF-CC (A3B6) antibody or IgG2a control were delivered via i.p. injection twice a week (300 mg/kg per week) starting from the day of tumor establishment. When tumors were palpable (longest diameter >3 mm), mice were randomized and treated with Tamoxifen (3 mg/kg) or vehicle (corn oil) via oral gavage daily.

Statistics

All statistics were calculated using SPSS V17 (SPSS, Chicago, USA). Spearman rank correlation was used to determine the associations of PDGF-CC expression with clinico-pathological parameters. Kaplan Meier analysis (with log rank test) and the Cox regression model were used for univariate or multivariate analyses. The statistics of the mouse experiments was evaluated using two-tailed independent student t-test with P≤0.05 considered significant.

Cell Culture

Murine MMTV-PyMT or MMTV-PyMT; PDGF-C$^{−/−}$ cells and human MDA-MB-231 cells were maintained in culture in DMEM Glutamax (Invitrogen), supplemented with 1% Penicillin/Streptomycin, 10% Fetal Bovine Serum (FBS) and glutamate.

In Vitro Stimulation 3×10$^6$ MMTV-PyMT; PDGF-C$^{−/−}$ cells were seeded in culture medium. After 24 hours, the cells were starved for 24 hours in DMEM Glutamax (Invitrogen), supplemented with 1% bovine serum albumin (BSA; Sigma Aldrich). The cells were stimulated with rmSTC1 (400 ng/mL; BioVendor), rmHGF (30 ng/mL;), rhIGFBP3 (250 ng/mL; R&D) or combinations of these factors in starvation medium for 48 hours. The cell line CAF2 (Kojima et al, PNAS, 2010) was used to produce CAF-conditioned medium. A monolayer of CAF2 cells was incubated for 48 hours in starvation medium. This conditioned medium was spun down (1500×g) to remove cells and used for downstream experiments.

Quantitative Reverse-Transcription PCR

In vitro-grown cells were washed twice with ice-cold PBS. RNA was isolated using RNAeasy MiniKit (Qiagen). cDNA was prepared using iScript cDNA Synthesis Kit (Bio Rad). KAPA SYBR FAST qPCR Kit Master Mix (KAPA Biosystems) was used for quantitative real-time PCR. The mRNA expression was normalized to the housekeeping gene L19. For FOXA1, EGFR and ESR1 QuantiTect Primer assay (Qiagen) primers were used. L19 primer pair (5' to 3'):

```
TTCAGCTTGTGGATGTGCTC
```
and
```
GGTGACCTGGATGAGAAGGA
```

GATA3 primer pair (5' to 3'):

```
CAATGCCTGCGGACTCTACC
```
and
```
GGTGGTGGTCTCGACAGTTCG
```

Western Blot

In vitro-grown cells were washed twice with ice-cold PBS and lysed 30 minutes on ice with 50 µl lysis buffer (20 mM Tris-HCl pH 7.5, 150 mM NaCl, 5 mM EDTA, 0.5% sodium deoxycholate, 0.5% Triton X). The lysate was spun down at 12000×g and the pellet discarded. The protein concentration was determined by absorption spectroscopy. The protein suspension was mixed with 5× loading buffer, denatured at 96° C. for 2 minutes and separated by SDS-PAGE on a 10% acrylamide gel. The proteins were transferred to an ethanol-activated PDCV membrane. The membrane was blocked 1 hour with 5% milk powder in PBST (0.05% Tween-20 in PBS) and incubated O/N at 4° C. with anti-Estrogen Receptor alpha antibody (ERα 1:200; SC-542, Santa Cruz) in blocking buffer. After washing, anti-Rabbit-HSP was applied 1:5000 in blocking buffer and incubated for 2 hours at RT. The membrane was washed and developed with SuperSignalR West Pico Chemoluminescent Substrate (Thermo Scientific). Luminescence signal was measured with an CCD camera (FluorChem E, Cell Biosciences).

In Vitro 4-Hydroxytamoxifen Treatment 15000 cells (either MMTV-PyMT or MMTV-PyMT; PDGF-C$^{-/-}$) were seeded in 96-well plates. After 24 hours incubation in growth medium followed by 24 hours starvation, the cells were stimulated either with CAF-conditioned medium or recombinant factors, as described before.

The cells were treated with increasing concentration of 4-hydroxytamoxifen (0-5 µM; Sigma Aldrich) in the respective stimulation medium at day 4 and 6 post-seeding. The cell proliferation reagent WST-1 (Roche) was used for the viability assay at day 7.

Tumor Grade Assessment

Tumor tissue from MMTV-PyMT, MMTV-PyMT; PDGF-C$^{+/-}$ and MMTV-PyMT; PDGF-C$^{-/-}$ mice (n=5 mice/genotype) was classified into different degrees of progression by quantifying the area of transformed glands occupied by each stage. Progression follows from normal fat tissue to a "precancerous stage" characterized by premalignant hyperplasia and adenoma (with the retention of some normal ductal and acinar mammary gland morphology), to a more epithelial cell-dense "early carcinoma" with stromal invasion, and finally to an invasive, very dense, high-mitotic index "late-stage carcinoma". Tumors were evaluated for the proportion of mammary fat tissue, hyperplastic tissue, adenoma, early carcinoma and late carcinoma. PDGF-C specific necrosis was described by a pathologist and scored blindly in the samples.

ERα Assessment

MDA-MB-231 human xenograft tumor tissue was immunostained and nuclear ERα positivity was evaluated at the end of the therapeutic trials. The region of interested was restricted to the tumor mass, without including the surrounding fat tissue. Both single-cell and foci quantification (n>3 cells/focus) was performed.

Quantification of Metastases

The left lung lobes of MMTV-PyMT were embedded in paraffin upon tissue fixation. The metastatic burden was assessed by serial sectioning of the entire lung/liver lobe. Following hematoxylin and eosin staining on every 25th section, the number of metastatic foci (>8 cells in diameter) was determined in >15 sections per mouse and >5 mice per group.

Results

PDGF-CC is an independent prognostic factor for poor survival in breast cancer In order to investigate the expression pattern of PDGF-CC in human breast, we performed immunostaining of a tissue microarray containing 890 tumor specimens, as well as normal breast tissue. The expression of PDGF-CC in normal breast tissue was limited to myoepitheliabasal cells and endothelial cells in capillaries, whereas most luminal cells were found to be negative for PDGF-CC expression (FIG. 1a-b). In breast tumors, PDGF-CC was expressed by malignant cells, intra-tumoral capillaries and stromal fibroblasts (FIG. 1b-e). Notably, PDGF-CC immunoreactivity was most conspicuous in the stroma directly adjacent to the malignant epithelium (FIG. 1f). Next, the staining intensity for PDGF-CC was graded independently for the epithelial and stromal compartment and correlated to clinico-pathological parameters (FIG. 1g). Stromal immunoreactivity for PDGF-CC was not correlated to patient outcome. In sharp contrast, moderate to high expression of PDGF-CC (score of 2+ and 3+) was found to be a highly significant prognostic factor for poor survival in univariate Cox regression and Kaplan-Meier analysis (RR 1.52, 95% Cl 1.16-1.99, p=0.003; FIG. 1h). Importantly, multivariate analysis adjusting for established clinical risk factors, such as age at diagnosis, stage, grade and lymph node status, among others, demonstrated that epithelial expression of PDGF-CC served as an independent prognostic factor for poor survival (RR 1.48, 95% CI 1.04-2.13, p=0.03). Interestingly, the two receptors of the PDGF family, i.e. PDGFRα and PDGFRs, were both exclusively expressed by stromal fibroblasts, indicating that malignant cells engage in paracrine communication with mesenchymal cells of the tumor microenvironment (FIG. 1i).

Figure 2:
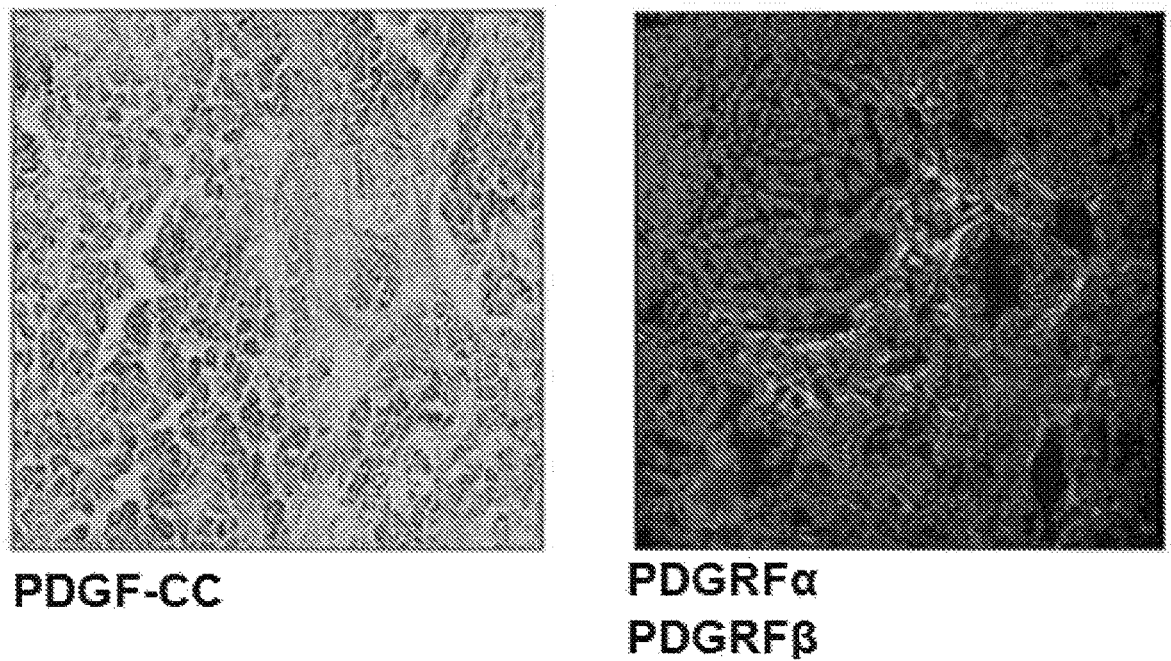
FIG. 2. Panel A shows PDGF-CC, PDGFRα and PDGFRβ expression in tumors of MMTV-PyMT mice. Panel B shows tumor volume of mammary tumors of MMTV-PyMT mice. Panel C-D shows tumor latency and survival. Panel E-F shows tumor stage and necrosis. Panel G shows pulmonary metastases. Panel H shows tumor volume after transplantation. Panel I shows tumor volume after injection.
Figure 2:
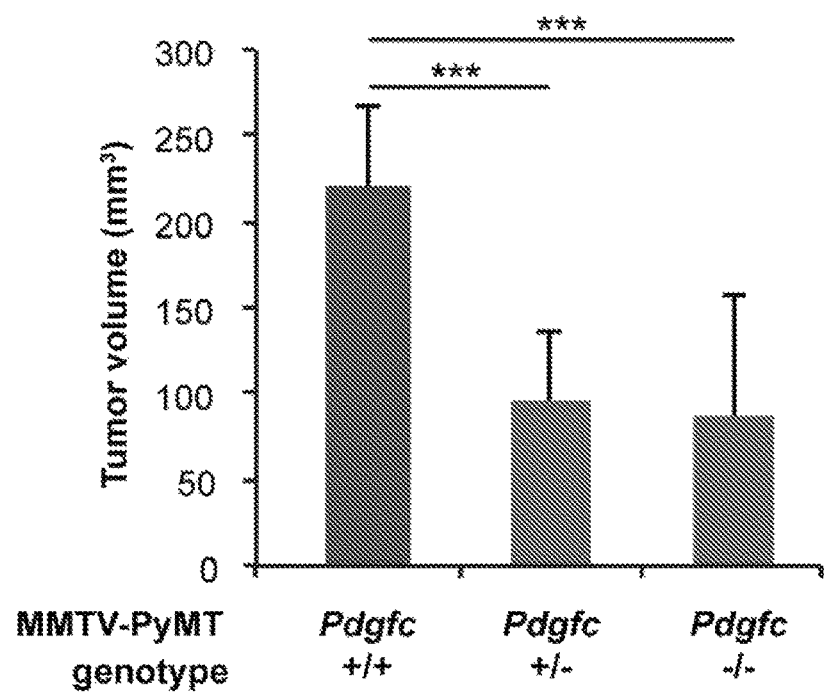

PDGF-CC is functionally important for the growth of experimental breast cancer Next, in order to investigate the functional aspects of PDGF-CC expression in the context of mammary gland tumorigenesis, we generated a genetically engineered mouse model of breast cancer based on the widely studied and clinically relevant MMTV-PyMT mouse intercrossed with mice deficient for Pdgfc (Pdgfc$^{lacz/lacz}$). Visualization of PDGF-CC, PDGFRα and PDGFRs expression in tumors of MMTV-PyMT mice demonstrated faithful recapitulation of the expression pattern in human breast cancers and established the existence of a paracrine circuitry between malignant cells and stromal fibroblasts (FIG. 2a). Strikingly, genetic deficiency for Pdgfc severely impacted on the growth of mammary tumors of MMTV-PyMT mice (FIG. 2b). Whereas control mice presented with tumors of an average size of 220±xx mm³, deficiency for a single, or both, copies of the gene encoding Pdgc reduced the average tumor size to 98±xx mm³ and 95±xx mm³, respectively (FIG. 2b). In addition to reducing the overall tumor burden, genetic deficiency for Pdgc was associated with a significantly longer tumor latency, as well as prolonged survival of MMTV-PyMT mice (FIG. 2c-d). Furthermore, tumors from age-matched mice lacking the gene encoding PDGFC were of lower stage, compared to tumors from control mice, and incorporated substantial areas of necrosis (FIG. 2e-f). Accordingly, 14-weeks old tumor-bearing mice presented with 26.3% fewer pulmonary metastases in the absence of signaling by PDGF-CC (FIG. 2g). However, this was most likely due to the delayed onset of disease, as a cohort of 12-weeks old wt mice displayed a similar metastatic burden as the 2 weeks older mice lacking Pdgfc (FIG. 2g).

To ascertain that the delayed tumor development in Pdgc-deficient mice was not due to developmental defects, we transplanted fragments of tumors from MMTV-PyMT; Pdgfc$^{+/+}$ and MMTV-PyMT; Pdgfl$^{lacz/lacz}$ mice orthotopically into the mammary fat pad of young wt mice. Consistent with our findings in the transgenic setting, transplanted Pdgc-deficient tumors displayed a dramatically hampered growth, compared to Pdgc-proficient tumors (FIG. 2h). Furthermore, whereas cell lines isolated from wt MMTV-PyMT mice readily gave rise to exponentially growing tumors following orthotopic transplantation into the mammary fat pad of wt or Pdgfc-deficient mice, two independently isolated cell lines from tumors of MMTV-PyMT; Pdgfc$^{lacz/lacz}$ mice were unable to establish as palpable tumors (FIG. 2i and data not shown).

Figure 3:
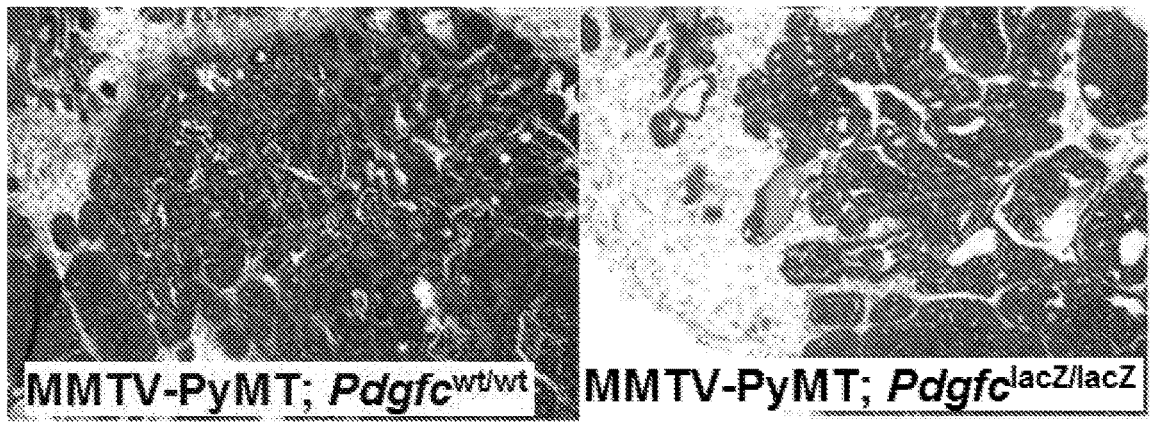
FIG. 3. Panel A shows Masson tri-chrome staining of tumor sections. Panel B shows that MMTV-PyMT; Pdgfc$^{lacz/lacz}$ mice were severely hemorrhagic. Panel C shows immunostaining for HIF-1α. Panel D shows expression of VEGF-A as determined by quantitative PCR analysis. Panels E-F show tumor volume and blood vessel density in SCID mice bearing orthotopically implanted MDA-MB-231 tumors and treated with A3B6 antibody or with control antibody.
Figure 3:
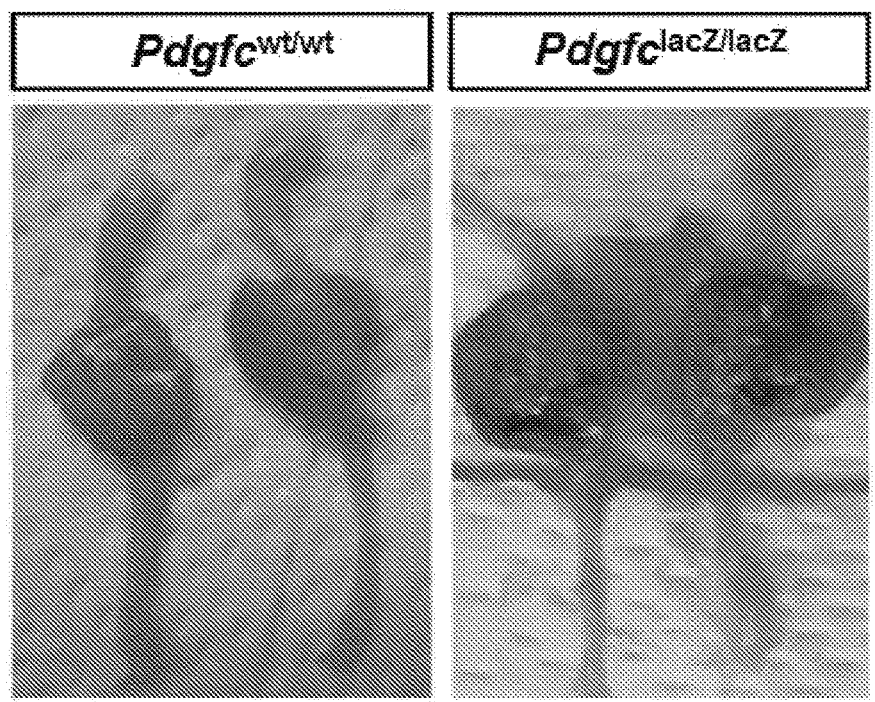

Deficiency for Pdgc Results in a Blunted Fibrotic and Angiogenic Response in the Tumor Microenvironment Histological analysis revealed considerable differences in the architecture of tumors from MMTV-PyMT; Pdgfc$^{+/+}$ and MMTV-PyMT; Pdgfc$^{lacz/lacz}$ mice. Masson tri-chrome staining of tumor sections demonstrated a severely reduced deposition of intratumoral collagen in the matrix of Pdgfc-deficient tumors, consistent with the notion that PDGF-CC acts to recruit and/or activate stromal fibroblasts in the breast tumor microenvironment (FIG. 3a). In addition, MMTV-PyMT; Pdgfc$^{lacz/lacz}$ mice were severely hemorrhagic (FIG. 3b) and exhibited significantly more hypoxia, as evidenced by immunostaining for HIF-1α (FIG. 3c). Accordingly, quantitative PCR analysis revealed a 65% lower expression of VEGF-A in the absence of PDGF-CC (FIG. 3d). In order to investigate whether pharmacological targeting of PDGF-CC as a mono-therapy impacted on breast tumor growth or angiogenesis, we treated SCID mice bearing orthotopically implanted MDA-MB-231 tumors (basal-like subtype) twice-weekly with the PDGF-CC antibody, A3B6 or with control antibody. Pharmacological blockade of PDGF-CC signaling marginally, albeit statistically significantly, impaired tumor growth and angiogenesis following 4 weeks of treatment (FIG. 3e-f). Taken together, we have demonstrated that deficiency for Pdgfc results in a blunted fibrotic and angiogenic response in the tumor microenvironment.

Expression of PDGF-CC in Breast Tumors is Associated with the Basal-Like Molecular Subtype.

Figure 4:
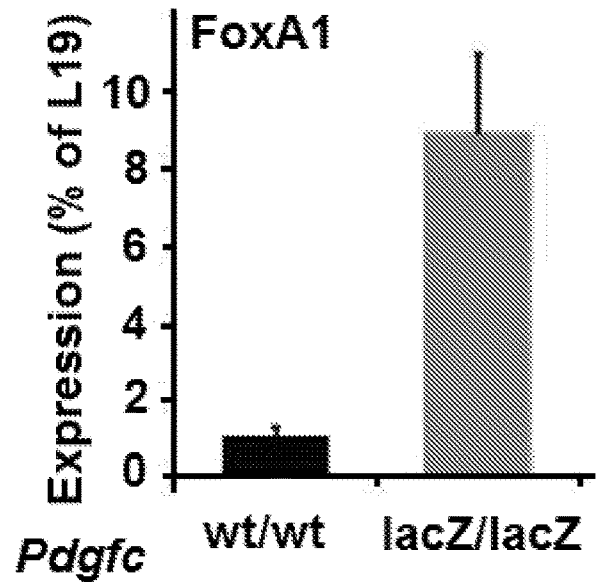
FIG. 4. Panel A and B show expression of Foxa1; lacZ/acZ is equivalent of PDGFC-/-. Panel C shows that expression of Foxa1 is highly correlated with a non-basal-like molecular subtype based on transcriptional profiles of breast tumors collected within The Cancer Genome Atlas project. Panel D shows expression of Foxa1 as a specific feature of tumors of the luminal subtype. Panel E shows immunostaining of a cohort of human breast tumor specimens for Foxa1. Panel F shows expression of PDGF-CC in breast tumor cell lines. Panel G shows that expression of Foxa1 is inversely correlated to expression of PDGF-CC.
Figure 4:
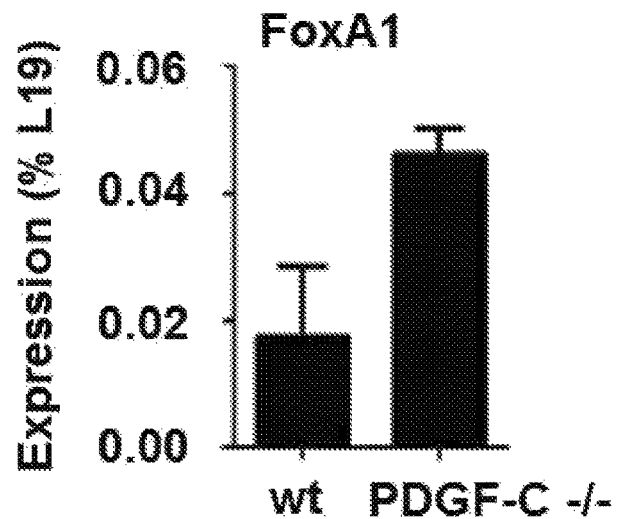

In order to elucidate the molecular significance of Pdgfc-deficiency, we performed transcriptional analysis on tumors derived from MMTV-PyMT; Pdgfc$^{+/+}$ and MMTV-PyMT; Pdgfc$^{lacz/lacz}$ mice using a quantitative PCR array designed to analyze the expression of genes of importance for breast tumor development and progression. The analysis revealed that the most differentially regulated gene was Foxa1, which was found to be expressed on average 8.9-fold higher in whole tumor lysates from Pdgc-deficient mice compared to wt mice (FIG. 4a). The expression of Foxa1 was also found to be dramatically elevated in tumor cell lines isolated from MMTV-PyMT; Pdgfc$^{lacz/lacz}$ mice (FIG. 4b). Human breast cancers may be classified into different molecular subtypes, including ER-positive breast cancers, such as normal-like, luminal A, luminal B, HER2$^+$ and ER-negative breast cancers, for example basal-like tumors. Analysis of transcriptional profiles of breast tumors collected within The Cancer Genome Atlas project revealed that expression of Foxa1 is highly correlated with a non-basal-like molecular subtype (FIG. 4c), confirming previous studies (ref). Indeed, mining of transcriptional data from a panel of 50 breast tumor cell lines revealed expression of Foxa1 as a specific feature of tumors of the luminal subtype (FIG. 4d). Immunostaining of a cohort of human breast tumor specimens confirmed the association between Foxa1 and the luminal subtype, as identified using hormone receptor (estrogen receptor-α (ER) and progesterone receptor (PR)) expression as a proxy (FIG. 4e). Given the fact that Foxa1 was found to be upregulated in tumor lysates in the absence of PDGF-CC, we investigated the correlation between Foxa1 and PDGF-CC in breast cancer. Firstly, expression of PDGF-CC was exclusively observed in breast tumor cell lines of basal-like subtype, but not in cells of luminal subtype origin (FIG. 4f). Secondly, in the panel of 50 breast tumor cell lines, Foxa1 and PDGF-CC expression were found to be inversely correlated (FIG. 4g). Thirdly, the association of PDGF-CC expression with the basal-like subtype of breast cancer was further established by analysis of expression of basal-like markers (cytokeratin 5/6) in a cohort of 890 human breast tumors by immunostaining. Strikingly, PDGF-CC was highly significantly associated with cytokeratin 5/6 expression, whereas low or absent expression of PDGF-CC denoted tumors of the luminal subtype expressing Foxa1, ER and PR.

A Paracrine Signaling Circuit in Stromal Fibroblasts Established by PDGF-CC Determines Molecular Subtype of Breast Tumor Cells.

Figure 5:
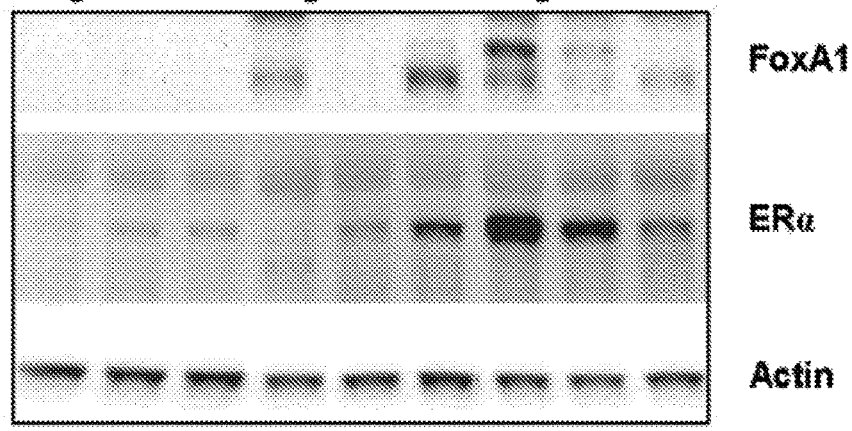
FIG. 5. Panel A shows expression of FoxA1 and ERα in tumor protein lysates. Panel B shows expression of stanniocalcin (STC)-1, hepatocyte growth factor (HGF) and insulin growth factor binding protein 3 (IGFBP3) as determined by quantitative PCR. Panels C to E shows expression of the luminal-like subtype markers FoxA1, ERα and GATA3, respectively after stimulation with STC-1, HGF and/or IGFBP3. Panel F shows sensitivity to tamoxifen-induced growth arrest. Panel G shows that conditioned medium from stromal fibroblasts can be substituted for the three paracrine PDGF-CC-induced factors. Panel H shows immunostaining of tumors from MMTV-PyMT mice for STC-1, HGF and IGFBP3.
Figure 5:
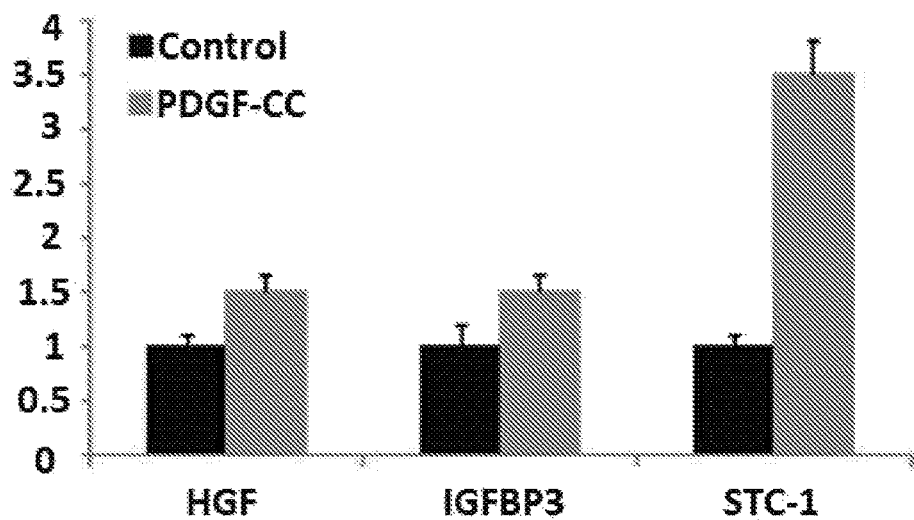

In accordance with the transcriptional analysis, the luminal subtype markers FoxA1 and ERα protein was found to be more abundant in tumor protein lysates from Pdgfc-deficient mice (FIG. 5a). In order to elucidate the mechanism whereby paracrine signaling by epithelium-derived PDGF-CC elicited specification of basal-like features of breast tumors, we stimulated the immortalized breast cancer-associated fibroblast cell line CAF2 with PDGF-CC. Following global gene expression analysis, we focused on genes encoding secreted proteins and validated 3 of these, stanniocalcin (STC)-1, hepatocyte growth factor (HGF) and insulin growth factor binding protein 3 (IGFBP3), by quantitative PCR to ensure induction by PDGF-CC (FIG. 5b). Next, we assessed whether stimulation of primary breast cancer cells isolated from tumors of MMTV-PyMT; Pdgfc$^{lacz/lacz}$ mice with STC-1, HGF and IGFBP3 rescued the basal-like phenotype of tumor cells from wt MMTV-PyMT mice using expression of the luminal-like subtype markers FoxA1, ERα and GATA3. Indeed, while each factor alone had varying effect, the concerted action of STC-1, HGF and IGFBP3 substantially suppressed the luminal-like features of Pdgfc-deficient mammary carcinoma cells (FIG. 5c-e). Importantly, the altered expression of ERα held functional significance, as pre-treatment of luminal breast cancer cells with STC-1, HGF and IGFBP3 reduced their sensitivity to tamoxifen-induced growth arrest (FIG. 5f). In addition, conditioned medium from stromal fibroblasts could be substituted for the three paracrine PDGF-CCinduced factors (FIG. 5g). The presence of STC-1, HGF and IGFBP3 in the tumor stroma of tumors from MMTV-PyMT mice was confirmed by immunostaining (FIG. 5h).

Genetic or Pharmacological Targeting of PDGF-CC Sensitizes Basal-Like Breast Tumors to Hormone Therapy.

Figure 6:
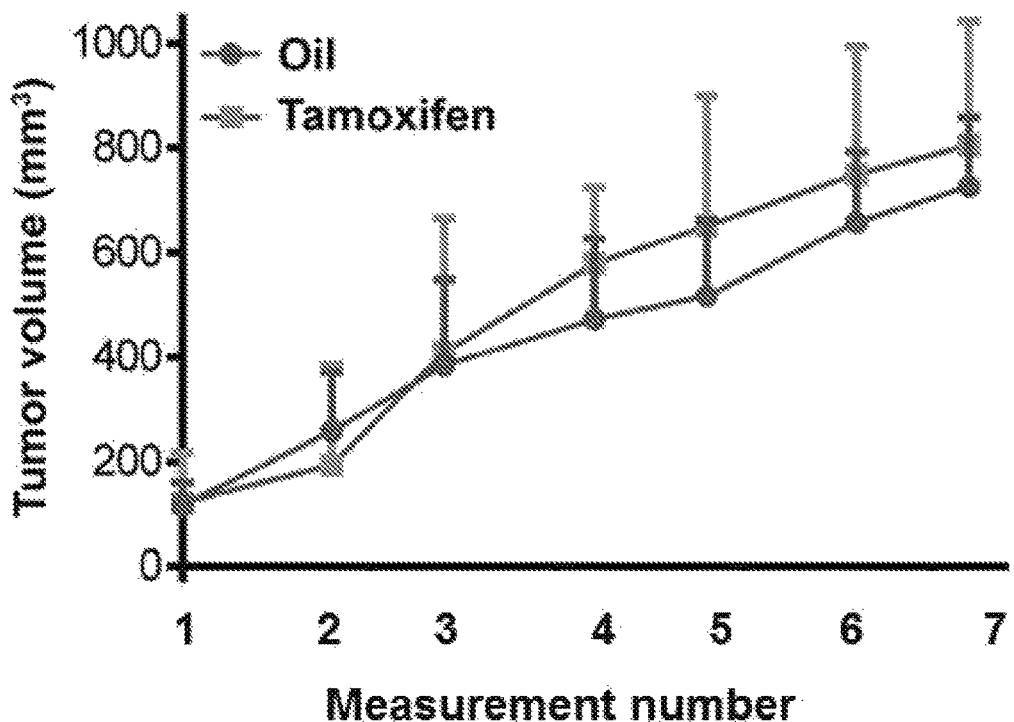
FIG. 6. Panel A shows tumor growth of wt tumors of tamoxifen-treated mice and untreated mice. Panel B shows tumor growth of tumors from Pdgc-deficient mice upon treatment with tamoxifen. Panel C shows tumor growth of fully established MDA-MB-231 tumors after treatment with tamoxifen. Panel D shows tumor growth of fully established MDA-MB-231 tumors after combined treatment with anti-PDGF-CC antibody A3B6 and tamoxifen. Panel E shows expression of ERα after treatment with monoclonal anti-PDGF-CC antibody A3B6. Panel F shows ERα expression in MDA-MB-231 tumors following blockade of signaling by PDGF-CC. Panel G shows a theoretical model of a paracrine signaling network in breast tumor microenvironment.
Figure 6:
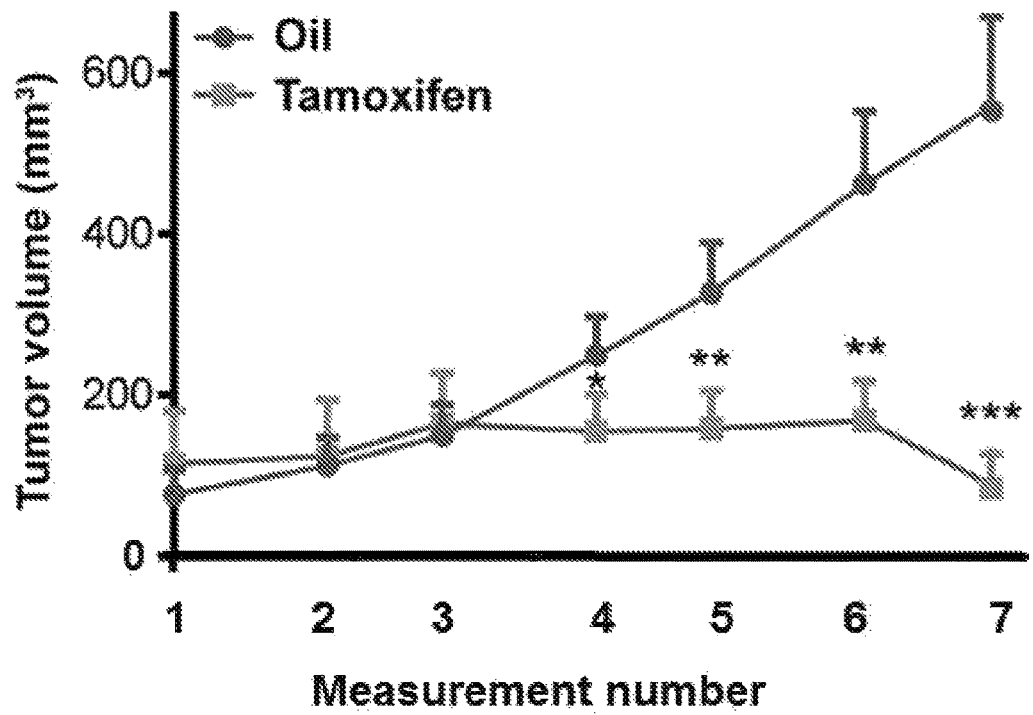

The clinically most important distinguishing feature of luminal subtype breast tumors is the expression of ERα, which confers sensitivity to hormone therapy, such as tamoxifen. We next set out to investigate whether targeting of PDGF-CC would convey sensitivity to hormone therapy to previously impervious ER-negative breast tumors of basal-like subtype. Non-transgenic mice bearing orthopically transplanted tumors from MMTV-PyMT; Pdgfc$^{+/+}$ or MMTV-PyMT; Pdgfc$^{lacz/lacz}$ mice were treated daily with tamoxifen starting from x weeks of age. As expected, the wt tumors of tamoxifen-treated mice continued to grow at a similar rate as tumors from untreated mice (FIG. 6a). In sharp contrast, and in agreement with them being ER-positive (FIG. 5a), tumors from Pdgfc-deficient mice were severely growth-retarded upon treatment with tamoxifen (FIG. 6b). At the end of the trial, tumors from tamoxifen-treated mice devoid of paracrine PDGF-CC signaling had a reduced volume, whereas untreated mice presented with tumors that had grown, evidently revealing functional sensitization of ERα-signaling within breast tumors by the Pdgfc-deficient tumor microenvironment. Histologically, tumors from tamoxifen-treated mice displayed. Finally, to conclusively demonstrate the therapeutic utility of agents targeting PDGF-CC to sensitize breast tumors of the basal-like subtype to the action of tamoxifen, we implanted MDA-MB-231 cells orthotopically into SCID mice. Treatment with tamoxifen together with a control antibody was unable to influence the growth of fully established MDA-MB-231 tumors (FIG. 6c). Strikingly, combined administration of tamoxifen and the PDGF-CC antibody A3B6 led to significant growth retardation of MDA-MB-231 tumors (FIG. 6d). Indeed, the basal-like subtype tumor that originally did not express meaningful levels of ERα, substantially upregulated expression of ERα upon treatment with monoclonal anti-PDGF-CC antibody A3B6, corroborating the role of paracrine signaling by PDGF-CC in establishing the absence of ERα in basal-like subtype breast tumors (FIG. 6e). Interestingly, the upregulation of ERα expression in MDA-MB-231 tumors following blockade of signaling by PDGF-CC was not uniform, but rather occurred in differentiated nests of malignant cells (FIG. 6f).

Without being bound by theory it is a paracrine signalling network is suggested manifested in the breast tumor microenvironment, in which epithelium-derived PDGF-CC orchestrates specification of the basal-like subtype through interactions with cancer-associated fibroblasts that express STC-1, HGF and IGFBP3 (FIG. 6g). Importantly, blockade of PDGF-CC, either by genetic or pharmacologic means, effected a sensitization of previously impervious basal-like subtype breast tumors to the action of hormone therapy by tamoxifen (FIG. 6g).

Example 2. Anti-PDGF-CC and Aromatase Inhibitor

For therapeutic studies, 2×106 Human MDA-MB-231 cells were inoculated orthotopically in the 4th mammary fat pad in SCID mice. Tumor growth was monitored and measured once a week with a caliper in live sedated animals. Mice had been randomly assigned before tumor inoculation to receive treatment with anti-PDGF-C (mouse monoclonal antibody clone A3B6) antibody or IgG2a isotype control antibody (Bio X Cell), which were delivered via i.p. injection twice a week (300 μg per week) starting from the day of tumor establishment. For therapeutic trials involving endocrine therapy, when a tumor was palpable (longest diameter >3 mm), mice were alternately assigned into the treatment groups in which mice were treated with letrozole (1 mg/dose via oral gavage daily, Sigma), dissolved in a vehicle of ethanol and corn oil (Sigma) by heating to 55° C., or with vehicle alone. All therapeutic administrations were open-label.

Figure 7:
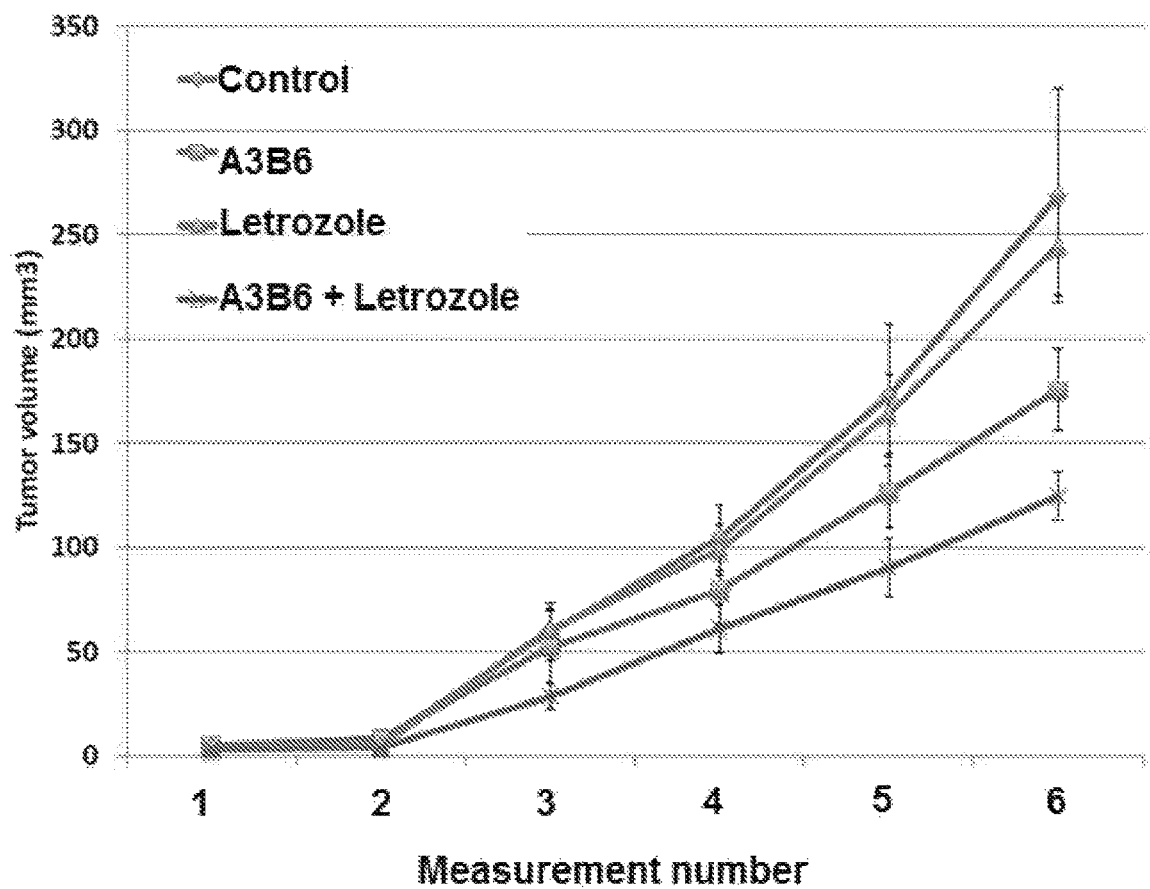
FIG. 7. Tumor growth in mice treated with anti-PDGF-CC antibody, Letrozole, a combination of anti-PDGF-CC antibody and Letrozole, and control.

The A3B6+letrozole group is statistically significantly smaller than all other groups (p<0.01 vs control, p<0.05 vs A3B6, p<0.001 vs letrozole, Student's unpaired, 2-sided t-test assuming equal variance); no other differences are statistically significant (FIG. 7).

Conclusion: neutralization of PDGF-CC sensitizes previously impervious basal-like/triple-negative breast tumors to the action of endocrine therapy in the form of aromatase inhibitors.

Example 3. PDGF-R Inhibitor and Estrogen Antagonist

For therapeutic studies, 2×106 Human MDA-MB-231 cells were inoculated orthotopically in the 4th mammary fat pad in SCID mice. Tumor growth was monitored and measured once a week with a caliper in live sedated animals. Mice had been randomly assigned before tumor inoculation to receive treatment with the PFGF-R inhibitor imatinib or to placebo, which were delivered via i.p. injection twice a week (300 μg per week) starting from the day of tumor establishment. For therapeutic trials involving endocrine therapy, when a tumor was palpable (longest diameter >3 mm), mice were alternately assigned into the treatment groups in which mice were treated with tamoxifen (1 mg/dose via oral gavage daily, Sigma), dissolved in a vehicle of ethanol and corn oil (Sigma) by heating to 55° C., or with vehicle alone. All therapeutic administrations were open-label.

Figure 8:
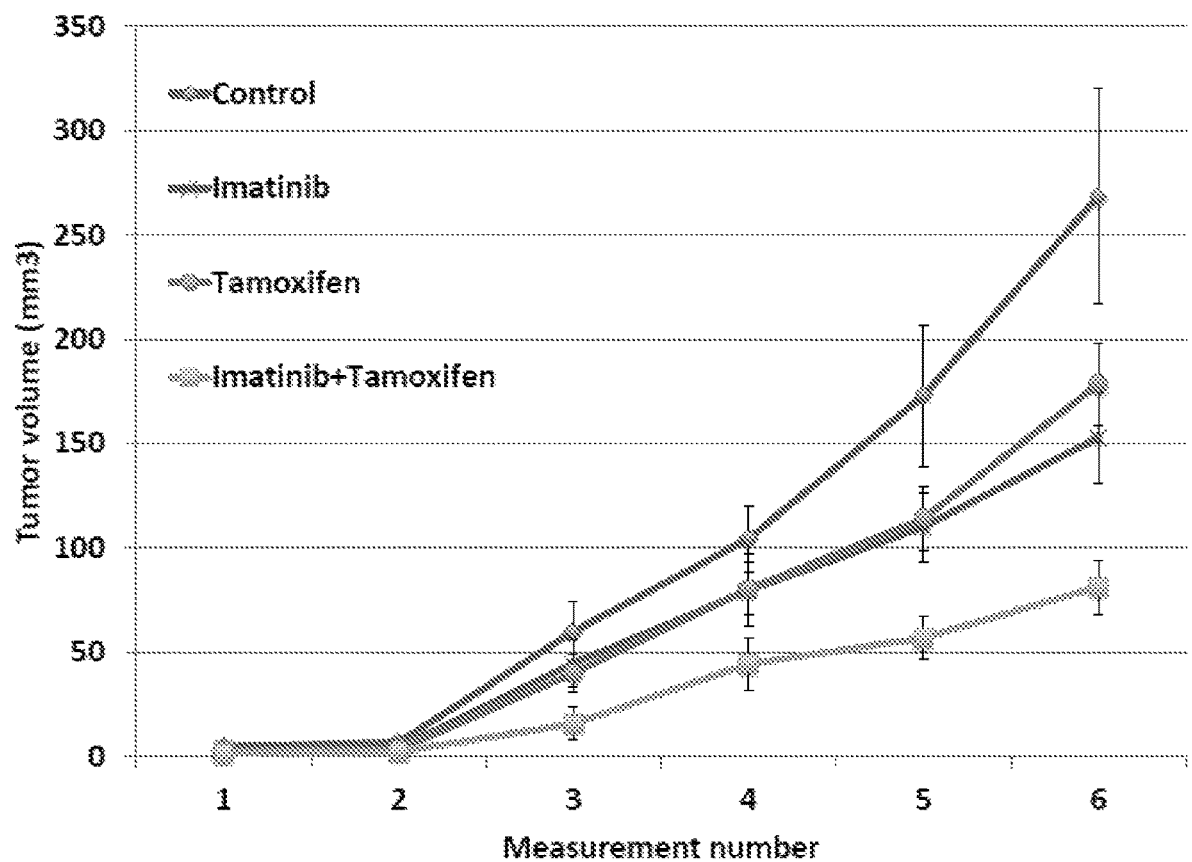
FIG. 8. Tumor growth in mice treated with Imatinib, Tamoxifen, a combination of Imatinib and Tamoxifen, control.

The imatinib+tamoxifen group is statistically significantly smaller than all other groups (p<0.01 vs control, p<0.05 vs A3B6, p<0.01 vs letrozole, Student's unpaired, 2-sided t-test assuming equal variance); no other differences are statistically significant (FIG. 8).

Conclusion: inhibition of the PDGFR tyrosine kinase sensitizes previously impervious basal-like/triple-negative breast tumors to the action of endocrine therapy in the form of tamoxifen.

REFERENCES

Relevance of breast cancer hormone receptors and other factors to the efficacy of adjuvant tamoxifen: patient-level meta-analysis of randomised trials
Early Breast Cancer Trialists' Collaborative Group (EBCTCG)
doi: 10.1016/S0140-6736(11)60993-8
Triple-Negative Breast Cancer
William D. Foulkes, M.B., B.S., Ph.D., Ian E. Smith, M.D., and Jorge S. Reis-Filho, M.D., Ph.D.
doil: 10.1056/NEJMra1001389)
Adjuvant treatments for triple-negative breast cancers by Joensuu and Gligorov Lancet 2011; 378:771-84
doi: 10.1093/annonc/mds194
Randomized Phase II Study of the Anti-Epidermal Growth Factor Receptor Monoclonal Antibody Cetuximab With Cisplatin Versus Cisplatin Alone in Patients With Metastatic Triple-Negative Breast Cancer José Baselga†, Patricia Gómez, Richard Greil, Sofia Braga, Miguel A. Climent, Andrew M. Wardley, Bella Kaufman, Salomon M. Stemmer, António Pêgo, Arlene Chan, Jean-Charles Goeminne, Marie-Pascale Graas, M. John Kennedy, Eva Maria Ciruelos Gil, Andreas Schneeweiss, Angela Zubel, Jutta Groos, Helena Melezínková and Ahmad Awada doi: 10.1200/JCO.2012.46.2408

Triple-Negative Breast Cancer: An Unmet Medical Need

Clifford A. Hudis and Luca Gianni doi: 10.1634/theoncologist2011-S1-01

Response to Neoadjuvant Therapy and Long-Term Survival in Patients With Triple-Negative Breast Cancer Cornelia Liedtke, Chafika Mazouni, Kenneth R. Hess, Fabrice André, Attila Tordai, Jaime A. Mejia, W. Fraser Symmans, Ana M. Gonzalez-Angulo, Bryan Hennessy, Marjorie Green, Massimo Cristofanilli, Gabriel N. Hortobagyi and Lajos Pusztai doi: 10.1200/JCO.2007.14.4147

American Society of Clinical Oncology/College of American Pathologists Guideline Recommendation for Immunohistochemical Testing of Estrogen and Progesterone Receptors in Breast Cancer.

Hammond et al., 2010, Journal of Clinical Oncology, vol. 28, no. 16, p. 2784-3543 Doi:10.1200/JCO.2009.25.6529

American Society of Clinical Oncology/College of American Pathologists Clinical Practice Guideline Update.

Hammond et al., 2013, Journal of Clinical Oncology, vol. 31 no. 31 3997-4013 doi: 10.1200/JCO.2013.50.9984.

J Clin Oncol. 2013 Nov. 1; 31(31):3997-4013. doi: 10.1200/JCO.2013.50.9984. Epub 2013 Oct. 7.

Recommendations for human epidermal growth factor receptor 2 testing in breast cancer American Society of Clinical Oncology/College of American Pathologists clinical practice guideline update.

Wolff A C, Hammond M E, Hicks D G, Dowsett M, McShane L M, Allison K H, Allred D C, Bartlett J M, Bilous M, Fitzgibbons P, Hanna W, Jenkins R B, Mangu P B, Paik S, Perez E A, Press M F, Spears P A, Vance G H, Viale G, Hayes D F; American Society of Clinical Oncology; College of American Pathologists.

---

The invention claimed is:

1. A method for treatment of triple negative breast cancer in an individual in need thereof, said method comprising administering a therapeutically effective amount of:

an anti-PDGF-CC antibody and tamoxifen to said individual either simultaneously or sequentially in any order,
wherein said triple negative breast cancer is characterized by absence of estrogen receptors, thereby treating the triple negative breast cancer, wherein the individual has suffered from triple negative breast cancer, and wherein said breast cancer in said individual has been treated by surgery, and wherein said treatment reduces the risk of relapse, wherein the individual is a human being.

2. The method according to claim 1, wherein said treatment comprises the steps of:
   a. administration of the anti-PDGF-CC antibody to said individual in need thereof; and
   b. subsequent administration of the tamoxifen.

3. The method according to claim 1, wherein the first administration of anti-PDGF-CC antibody to said individual is prior to the first administration of said tamoxifen.

4. The method according to claim 1, wherein the anti-PDGF-CC antibody is a monoclonal antibody specifically binding PDGF-CC.

5. The method according to claim 1, wherein the triple negative breast cancer is a basal-like breast cancer.

6. The method according to claim 1, wherein the triple negative breast cancer is a triple negative primary tumor.

* * * * *

SEQUENCE LISTING

```
<160> NUMBER OF SEQ ID NOS: 9

<210> SEQ ID NO 1
<211> LENGTH: 345
<212> TYPE: PRT
<213> ORGANISM: Homo sapiens

<400> SEQUENCE: 1

Met Ser Leu Phe Gly Leu Leu Leu Thr Ser Ala Leu Ala Gly Gln
1               5                   10                  15

Arg Gln Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220
```

-continued

```
Lys Ala Phe Val Phe Gly Arg Lys Ser Arg Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345

<210> SEQ ID NO 2
<211> LENGTH: 22
<212> TYPE: DNA
<213> ORGANISM: Artificial Sequence
<220> FEATURE:
<223> OTHER INFORMATION: Synthetic Construct

<400> SEQUENCE: 2
ggaagcaagt acttcacaag gg                                          22

<210> SEQ ID NO 3
<211> LENGTH: 21
<212> TYPE: DNA
<213> ORGANISM: Artificial Sequence
<220> FEATURE:
<223> OTHER INFORMATION: Synthetic Construct

<400> SEQUENCE: 3
ggaaagtcac taggagcagg g                                           21

<210> SEQ ID NO 4
<211> LENGTH: 21
<212> TYPE: DNA
<213> ORGANISM: Artificial sequence
<220> FEATURE:
<223> OTHER INFORMATION: Synthetic Construct

<400> SEQUENCE: 4
agctgacatt tgatgagaga t                                           21

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct

<400> SEQUENCE: 5
agtaggtgaa ataagaggtg aaca                                        24

<210> SEQ ID NO 6
<211> LENGTH: 21
<212> TYPE: DNA
<213> ORGANISM: Artificial sequence
<220> FEATURE:
<223> OTHER INFORMATION: Synthetic Construct
```

-continued

```
<400> SEQUENCE: 6
ctcatgttct cgtgactctg a                                              21

<210> SEQ ID NO 7
<211> LENGTH: 20
<212> TYPE: DNA
<213> ORGANISM: Artificial sequence
<220> FEATURE:
<223> OTHER INFORMATION: Synthetic Construct

<400> SEQUENCE: 7
tagctagtcg ataccgtcga                                                20

<210> SEQ ID NO 8
<211> LENGTH: 1089
<212> TYPE: PRT
<213> ORGANISM: Homo sapiens
<220> FEATURE:
<221> NAME/KEY: PEPTIDE
<222> LOCATION: (1)..(1089)
<223> OTHER INFORMATION: PDGF-R alpha isoform 1

<400> SEQUENCE: 8
```

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

```
Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Arg Ile Ser Trp Leu Lys Asn
                340                 345                 350

Asn Leu Thr Leu Ile Glu Asn Leu Thr Glu Ile Thr Thr Asp Val Glu
                355                 360                 365

Lys Ile Gln Glu Ile Arg Tyr Arg Ser Lys Leu Lys Leu Ile Arg Ala
370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp His His Gly Ser Thr Gly Gly Gln Thr
                420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
        450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
                500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
        530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
                580                 585                 590

Leu Val Leu Gly Arg Val Leu Gly Ser Gly Ala Phe Gly Lys Val Val
                595                 600                 605

Glu Gly Thr Ala Tyr Gly Leu Ser Arg Ser Gln Pro Val Met Lys Val
        610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
                660                 665                 670

Ile Thr Glu Tyr Cys Phe Tyr Gly Asp Leu Val Asn Tyr Leu His Lys
                675                 680                 685
```

```
Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu Lys Asp Trp Glu Gly Gly Leu Asp
        995                 1000                1005

Glu Gln Arg Leu Ser Ala Asp Ser Gly Tyr Ile Ile Pro Leu Pro
    1010                1015                1020

Asp Ile Asp Pro Val Pro Glu Glu Glu Asp Leu Gly Lys Arg Asn
    1025                1030                1035

Arg His Ser Ser Gln Thr Ser Glu Glu Ser Ala Ile Glu Thr Gly
    1040                1045                1050

Ser Ser Ser Ser Thr Phe Ile Lys Arg Glu Asp Glu Thr Ile Glu
    1055                1060                1065

Asp Ile Asp Met Met Asp Asp Ile Gly Ile Asp Ser Ser Asp Leu
    1070                1075                1080

Val Glu Asp Ser Phe Leu
    1085
```

-continued

```
<210> SEQ ID NO 9
<211> LENGTH: 1106
<212> TYPE: PRT
<213> ORGANISM: Homo sapiens
<220> FEATURE:
<221> NAME/KEY: PEPTIDE
<222> LOCATION: (1)..(1106)
<223> OTHER INFORMATION: PDGF-R beta Isoform 1

<400> SEQUENCE: 9
```

Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

-continued

```
Thr Arg Asn Val Ser Glu Thr Arg Tyr Val Ser Glu Leu Thr Leu Val
    370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
                405                 410                 415
Val Arg Val Leu Glu Leu Ser Glu Ser His Pro Asp Ser Gly Glu Gln
                420                 425                 430
Thr Val Arg Cys Arg Gly Arg Gly Met Pro Gln Pro Asn Ile Ile Trp
            435                 440                 445
Ser Ala Cys Arg Asp Leu Lys Arg Cys Pro Arg Glu Leu Pro Pro Thr
    450                 455                 460
Leu Leu Gly Asn Ser Ser Glu Glu Glu Ser Gln Leu Glu Thr Asn Val
465                 470                 475                 480
Thr Tyr Trp Glu Glu Glu Gln Glu Phe Glu Val Val Ser Thr Leu Arg
                485                 490                 495
Leu Gln His Val Asp Arg Pro Leu Ser Val Arg Cys Thr Leu Arg Asn
                500                 505                 510
Ala Val Gly Gln Asp Thr Gln Glu Val Ile Val Val Pro His Ser Leu
            515                 520                 525
Pro Phe Lys Val Val Ile Ser Ala Ile Leu Ala Leu Val Val Leu
    530                 535                 540
Thr Ile Ile Ser Leu Ile Ile Leu Ile Met Leu Trp Gln Lys Lys Pro
545                 550                 555                 560
Arg Tyr Glu Ile Arg Trp Lys Val Ile Glu Ser Val Ser Ser Asp Gly
                565                 570                 575
His Glu Tyr Ile Tyr Val Asp Pro Met Gln Leu Pro Tyr Asp Ser Thr
                580                 585                 590
Trp Glu Leu Pro Arg Asp Gln Leu Val Leu Gly Arg Thr Leu Gly Ser
            595                 600                 605
Gly Ala Phe Gly Gln Val Val Glu Ala Thr Ala His Gly Leu Ser His
    610                 615                 620
Ser Gln Ala Thr Met Lys Val Ala Val Lys Met Leu Lys Ser Thr Ala
625                 630                 635                 640
Arg Ser Ser Glu Lys Gln Ala Leu Met Ser Glu Leu Lys Ile Met Ser
                645                 650                 655
His Leu Gly Pro His Leu Asn Val Val Asn Leu Leu Gly Ala Cys Thr
                660                 665                 670
Lys Gly Gly Pro Ile Tyr Ile Ile Thr Glu Tyr Cys Arg Tyr Gly Asp
            675                 680                 685
Leu Val Asp Tyr Leu His Arg Asn Lys His Thr Phe Leu Gln His His
    690                 695                 700
Ser Asp Lys Arg Arg Pro Pro Ser Ala Glu Leu Tyr Ser Asn Ala Leu
705                 710                 715                 720
Pro Val Gly Leu Pro Leu Pro Ser His Val Ser Leu Thr Gly Glu Ser
                725                 730                 735
Asp Gly Gly Tyr Met Asp Met Ser Lys Asp Glu Ser Val Asp Tyr Val
            740                 745                 750
Pro Met Leu Asp Met Lys Gly Asp Val Lys Tyr Ala Asp Ile Glu Ser
    755                 760                 765
Ser Asn Tyr Met Ala Pro Tyr Asp Asn Tyr Val Pro Ser Ala Pro Glu
770                 775                 780
```

```
                                -continued

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
                820                 825                 830

Leu Ile Cys Glu Gly Lys Leu Val Lys Ile Cys Asp Phe Gly Leu Ala
            835                 840                 845

Arg Asp Ile Met Arg Asp Ser Asn Tyr Ile Ser Lys Gly Ser Thr Phe
    850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
                900                 905                 910

Phe Tyr Asn Ala Ile Lys Arg Gly Tyr Arg Met Ala Gln Pro Ala His
            915                 920                 925

Ala Ser Asp Glu Ile Tyr Glu Ile Met Gln Lys Cys Trp Glu Glu Lys
930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
                980                 985                 990

Pro Gly Phe His Gly Leu Arg Ser  Pro Leu Asp Thr Ser  Ser Val Leu
            995                 1000                1005

Tyr Thr  Ala Val Gln Pro Asn  Glu Gly Asp Asn Asp  Tyr Ile Ile
    1010                1015                1020

Pro Leu  Pro Asp Pro Lys Pro  Glu Val Ala Asp Glu  Gly Pro Leu
    1025                1030                1035

Glu Gly  Ser Pro Ser Leu Ala  Ser Ser Thr Leu Asn  Glu Val Asn
    1040                1045                1050

Thr Ser  Ser Thr Ile Ser Cys  Asp Ser Pro Leu Glu  Pro Gln Asp
    1055                1060                1065

Glu Pro  Glu Pro Glu Pro Gln  Leu Glu Leu Gln Val  Glu Pro Glu
    1070                1075                1080

Pro Glu  Leu Glu Gln Leu Pro  Asp Ser Gly Cys Pro  Ala Pro Arg
    1085                1090                1095

Ala Glu  Ala Glu Asp Ser Phe  Leu
    1100                1105
```